United States Patent
Felden

(10) Patent No.: US 7,888,029 B2
(45) Date of Patent: Feb. 15, 2011

(54) EUBACTERIAL TMRNA SEQUENCES AND USES THEREOF

(75) Inventor: Brice Felden, Le Lou du Lac (FR)

(73) Assignee: University of Utah Research Foundation, Salt Lake City, UT (US)

( * ) Notice: Subject to any disclaimer, the term of this patent is extended or adjusted under 35 U.S.C. 154(b) by 238 days.

(21) Appl. No.: 12/163,371

(22) Filed: Jun. 27, 2008

(65) Prior Publication Data

US 2009/0117570 A1    May 7, 2009

Related U.S. Application Data

(62) Division of application No. 11/329,230, filed on Jan. 11, 2006, now Pat. No. 7,611,843, which is a division of application No. 09/958,206, filed as application No. PCT/US00/08988 on Apr. 6, 2000, now Pat. No. 7,115,366.

(60) Provisional application No. 60/128,058, filed on Apr. 7, 1999.

(51) Int. Cl.
| | |
|---|---|
| C12Q 1/68 | (2006.01) |
| A01N 43/04 | (2006.01) |
| A61K 31/70 | (2006.01) |
| C07H 21/02 | (2006.01) |
| C07H 21/04 | (2006.01) |
| C12P 19/34 | (2006.01) |

(52) U.S. Cl. .................. 435/6; 435/91.1; 435/91.2; 514/44 R; 536/23.1; 536/23.7

(58) Field of Classification Search .................. None
See application file for complete search history.

(56) References Cited

U.S. PATENT DOCUMENTS 5,861,245 A * 1/1999 McClelland et al. .......... 435/6

OTHER PUBLICATIONS

Genbank Accession No. U68080, Williams et al. Feb. 26, 1997.*

B. Felden et al., "Eubacterial tmRNAs: everywhere except the alpha-Proteobacteria?"Biochimica et Biophysica Acta 1446:145-148, 1999.

N. Nameki et al., "Three of four pseudoknots in tmRNA are interchangeable and are substitutable with single-stranded RNAs," FEBS Lett 470(3):345-349, Mar. 31, 2000.

N. Nameki et al., "Functional and structural analysis of a pseudoknot upstream of the tag-encoded sequence in *E. coli* tmRNA," J. Mol. Biol 286(3):733-744, Feb. 26, 1999.

W. Schönhuber et al., "Utilization of tmRNA squences for bacterial identification," MBC Microbiology 2001, 1:20 (online, 8 pages).

K.P. Williams et al., "Phylogenetic analysis of tmRNA secondary structure," RNA 2:1306-1310, 1996.

C. Zwieb et al., "Survey and Summary, Comparative sequence analysis of tmRNA," Nucleic Acids Research 27(10):2063-2071, 1999.

Huang, C. et al., "Charged tmRNA but not tmRNA-mediated proteolysis is essential for *Neisseria gonorrhoeae* viability," The EMBO Journal, vol. 19, No. 5, pp. 1098-1107, 2000, copyright European Molecular Biology Organization.

Ley, B.E. et al., "Eubacterial approach to the diagnosis of bacterial infection," Archives of Disease in Childhood 1997;77:148-149.

* cited by examiner

*Primary Examiner*—Janet Epps-Smith
(74) *Attorney, Agent, or Firm*—Rothwell, Figg, Ernst & Manbeck pc

(57)    ABSTRACT

The present invention is directed to eubacterial tmDNA sequences and the corresponding tmRNA sequences. The present invention is further directed to alignments of eubacterial tmDNA sequences and the use of the sequences and sequence alignments for the development of antibacterial drugs. The present invention is also directed to the use of the sequences for the development of diagnostic assays.

6 Claims, 24 Drawing Sheets

```
                     ┌─CODING SEQUENCE                                    H4
                     │                                               ┌─────────┐
                     ▼                                               │  ┌───┐  │
Tab.saccha  AUAAAC gcaaacgauaau--------------uuagcuuacgcugcuUAA UA-CAAGCAGC---
C.acetobut  ******|************-------------************************|***********---
C.stercora  AUAAAC gcaaacaacgauaacuac--------gcuuuagcugcugcgUAA GUAACACGCAGCC--
C.perfrige  AUAAAC gcagaagauaau--------------uuugcauuagcagcuUAA UUUAGCGCUGCU---
C.lentocel  GUAAAC gcugaagauaau--------------uuagcaaucgcugccUAA UA-AGGC-GC----
Hlb.mobili  UUAAUU gccgaagauaac--------------uacgcuuuagcugcuUUA UUGCAGUCUAA---
Hsp.gestii  UUAAUU gccgaagauaac--------------uacgcuuuagcugcuUAA UUGCAGUCUAA---
Bb.brevis   UUAACU ggcaacaaacaa--------------cuuucucucgcugcuUAA UAACCAGUGAG---
B.subtilis  AUAACU ggcaaaacuaacaguuuuaaccaaaacguagcauuagcugccUAA UAAGCGCAGCGA--
B.badius    AUAACU ggcaaaaagau---------------uuagcuuuagcugccUAA UAUAGGUUCAGCU--
B.megateri  AUAACU ggcaaaucuaacaauaac--------uucgcuuuagcugcaUAA UAGUAGCUUAGC---
B.thermole  AUAACU ggcaaacaaaac--------------uacgcuuuagcugccUAA UUGCUGCAGCUA---
Eco.fecium  AUAACU gcuaaaaacgaaaacaacucu-----uacgcuuuagcugccUAA AAA-CAGUUAGCGUA
Eco.faecal  AUAACU gcuaaaaacgaaaacaauucu-----uucgcuuuagcugccUAA AAACCAGCUAGCGAA
Stc.pyogen  AUAACU gcaaaaaauacaaacucu--------uacgcuuuagcugccUAA AAACCAGCUAGCGU-
Stc.pneumo  AUAACU gcaaaaaauaacacuucu--------uacgcucuagcugccUAA AAACCAGCAGGCGU-
Stc.gordon  AUAACU gcaaaaaauaauacuucu--------uacgcuuuagcugccUAA AAACCAGCGGGCGU-
Stc.mutans  AUAACU gcaaaaaauacaaauucu--------uacgcaguagcugccUAA AAACCAGCCUGUGU-
Stp.epider  AUAACU gacaaaucaaacaauaau--------uucgcaguagcugcgUAA UAGCCACUGC-----
Stp.aureus  AUAACU ggcaaaucaaacaauaau--------uucgcaguagcugccUAA UCGCA-CU-CUGC--
L.acidophi  AUAACU gcaaauaacaaaaauucu--------uacgcauuagcugcuUAA UUUAGCGCAUGCGU- Tab.saccha  CGUUCAA-CCUU-UGAU-UCCCAC--AUCA-AAGGAUUGGGCGUCG--AUUUAGUGGGG
C.acetobut  *********-******--*AAUCUGGCGUCG----AGAGCGGGG
C.stercora  CGUCGG-C-CCCCGGGGUUCCUGC---GCCUCGGGAUACCGGCGUCA---UCAAGGCAGG
C.perfrige  CAUCCUU--CCU-CAAUUGCCCACG-GUUG-AGAGUAAGGGUGUCAUUUAAAAGUGGGG
C.lentocel  AGUCCU---CCU-AGGUCUUCCGCA-GCCU-AGAUC-AGGGCUUCG---ACUCGCGGAU
Hlb.mobili  CCUCUU-C-UCC-UC-UGUGCUCUCGGUGA-GGAUGUAAGGGGUCA-UUUAAGAGAGCU
Hsp.gestii  CCUCUU-C-UCC-UC-UGUGCUCUCGGUGA-GGAUGUAAGGGGUCA-UUUAAGAGAGCU
Bb.brevis   GCUCUC-CCACU-GCAUCGGCCGU-GUGC-CGUGGAUAGGGCUCAACUUUAACGGGCU
B.subtilis  GCUCUUC--CUG-ACAU-UGCCUAU-GUGU-CUGU-GAAGAGCACA-UCCAAGUAGGCU
B.badius    GCUCCU--CCCG-CUAU-CGUCCAU-GUAGUCGGGUAAGGGGUCCAAACUUAGUGGACU
B.megateri  GUUCCU--CCCU-CCAU-CGCCCAU-GUGGUAGGGUAAGGGACUCACUUUAAGUGGGCU
B.thermole  GCUCCUC--CCG-CCAU-CGCCCGC-GUGG-CGUUCGAGGGGCUCAUAUGGAGCGGGCU
Eco.fecium  GAUCCU--CUCG-GCAU-CGCCCAU-GUGCUCGAGUAAGGGUCUCAAAUUUAGUGGGAU
Eco.faecal  GAUCCU--CCCG-GCAU-CGCCCAU-GUGCUCGGGUCAGGGUCCUAAUCGAAGUGGGAU
Stc.pyogen  GACUUCU--ACA-AGAU-UGCUUGU-GUCC-UGUU-AGAAGUC-UCAAAAUAGCAAGCU
Stc.pneumo  GACCC--GAUUU-GGAU-UGCUCGU-GUUC-AAUGA-CAGGUCUUAUUAUUAGCGAGAU
Stc.gordon  GACCC--GAUUC-GGAU-UGCUUGU-GUCU-GAUGA-CAGGUCUUAUUAUUAGCAAGCU
Stc.mutans  GAUCAAU--AAC-AAAU-UGCUUGU-GUUU-GUUG-AUUGGUCUUAUUGUUAACAAGCU
Stp.epider  AUCGCC-UAACA-GCAU-CUCCUAC-GUGC-UGUUAACGCGAUUCAACCCUAGUAGGAU
Stp.aureus  AUCGCC-UAACA-GCAU-UUCCUAU-GUGC-UGUUAACGCGAUUCAACCUUAAUAGGAU
L.acidophi  UGCUCU-UUGUC-GGUU-UACUCGU-GGCU-GACAC-UGAGUAUCA-ACUUAGCGAGUU
                                                      └─────┘    └─────┘
                                                           PK2
```

FIG. 3B

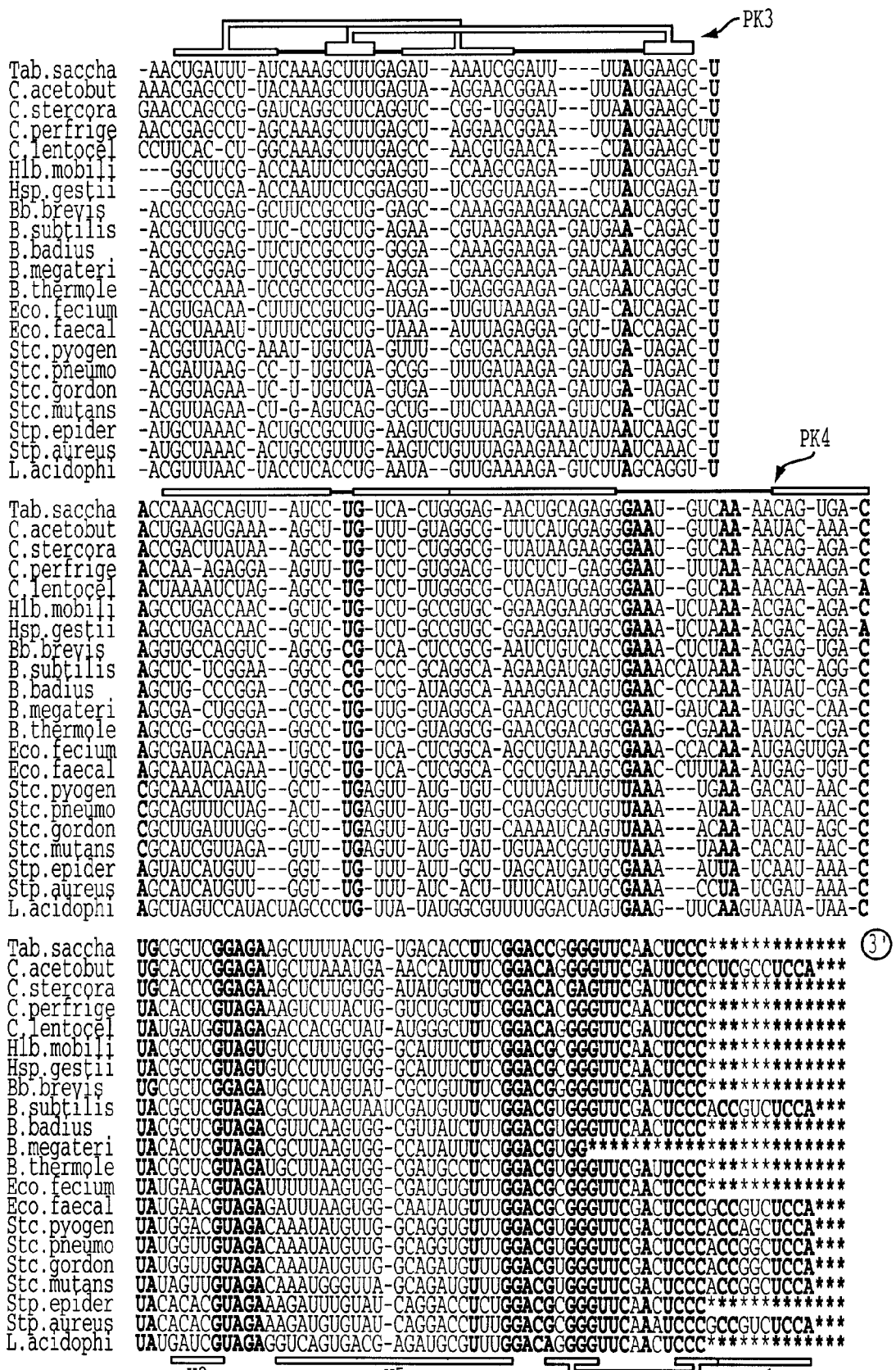
FIG. 3C  +RNA-LIKE DOMAIN H1-H6

```
Aqf.aeolic  CG-GGCUACUCGGU--CGCACGGG-GCUGAGUAGCUGACACCUAACCCGUGCU ⎫
Tt.maritim  A--CCGAUUCAG--UUCGCCUUCCGGCCUGAAUCGGGAAAACUCAGGAAGGCU │
Tt.neapoli  A--CCGAUCUGGGCUCCGCCUUCCGGCCCGGAUCGGGAAGGUUCAGGAAGGCU │
T.thermoph  A--GCCCGGGGC--CACGCCCUCU--AACCCCGGGCGAAGCUUGAAGGGGGCU │
D.radiodur  A--GCCC-AGGC--GAUUCUCCAU--AGCCGACGGCGAAACU-UUAUGGAGCU │
D.proteoly  A--GCUU-AGGU--GAGGUUCCAU--AGCCAAAAGUGAAACC-AAAUGGAAAU ⎬ PK3
Tmc.roseum  GCCCCUGGCCCA--AGCGCCGGUG---CGGGCCAGGUCAAGCGUGAUCCGGCU │
Ctb.proteo  GC-UCUUAAGCAG--UGGCACCAG--CUGUUUAAGGGUGAAAAGAGUGGUGCU │
Her.aurant  CGCUCCCCUAGUU--AUGUCUGUG--GGCUAGGGG--CUAAGAUUAACAGGCU │
Tdb.commun  UU-GGGAGGCUUAA-UCGGUGGGG--UUAAGCCUCCCGAGAUUACAUCCCACCU │
Ver.spinos  G--GCCAAAAGAGC-GGGCGACCG-GC-CCCAAGGCGAGAUCUACAGGCCGCU │
Dcg.thermo  GCCCCUUCCG-----ACUCCCCUA-----AGGAAGGGAAAGA-UGUAGGGGAU ⎭
                                  ══════════

Aqf.aeolic  A--CCCUC-GGGGAGCUUGCCCGUGGGCGACCC-GAGGG--GAAAUCC-UGAACACGGGC ⎫
Tt.maritim  G-UGGGAGAGGACACCCUGCCCGUGGGAGGUCC-CUCCC--GAGACG-AAAACACGGGC │
Tt.neapoli  G-UGGGAAGCGACACCCUGCCCGUGGGGGGUC-CUUCCC--GAGACAC-GAAACACGGGC │
T.thermoph  C-GCUCCUGGCC--GCCCGUCCGCGGGCCAAGCCAGGAG--GACACGC-GAAACGCGGAC │
D.radiodur  A-CGGCCUGCGAGAACCUGCCCACUGGUGAGCGCCGGCCC-GACAAUC-AAACAGUGGGA │
D.proteoly  A-AGGCGGACGGCAGCCUGUUUGCUGGCAGCCCAGGCCC--GACAAUU-UAAGAGCAGAC ⎬ PK4
Tmc.roseum  C-GGCUGACCGGGAUCCUGUCGGUGGGAGCCUGG-CAGC--GACAGUA--GAACACCGAC │
Ctb.proteo  G--GGCAGUGCGGUU-GGGCU-UCCUGGGCUGCACUGUC--GACACUU-CACAGGAGGGC │
Her.aurant  G-GUCGUGGC-CCGCUUUGUCUAUCGGGUGGUGCACCGAU-AAGAUUU-AAUCAAUAGAC │
Tdb.commun  G--GUAGGGUUGCUUGGUGCCUGUGACAAGCA-CCCUAC--GAGAUUU--UCCCACAGGC │
Ver.spinos  G--GAUGGACGGCAUCCUGGCAGUAGGAGGCUGGACAUC--GAGAUCA--AAUNAUUGCC │
Dcg.thermo  AGGUGCUUACAGAAUCCUGCGGGAGGGAGUCUGUAAGUGCCGAAAAGUUAAAACUCCCGC ⎭
                              ══════════                          ═════

Aqf.aeolic  UAAGCC-UGUAGAGCCUCGGAUGUGGCCGCCGUCCUCGGACGCGGGUUCGAUUCCCGCCGCCUCCACCA
Tt.maritim  UGCGCU-CGGAGAAGCCCAGGGG---CCUCCAUCUUCGGACGGGGGUUCGAAUCCCCCGCCUCCACCA
Tt.neapoli  UGCGCU-CGGAGAAGCCCAGGGG---CCUCCAUCUUCGGACGGGGGUUCGAUUCCCGCCGCCUCCA***
T.thermoph  UACGCG-CGUAGAGGCcacgccc---cggcgaccuucggacgggggguucgauucccccaccuccacca
D.radiodur  UACACA-CGUAGACGCA-CGCUG---GACGGACCUUUGGACGGCGGUUCGACUCCGCCCACCUCCACCA
D.proteoly  UACGCA-CGUAGAUGCA-CGCUG---GAUGGACCUUUGGACGGCGGUUCGAUUCCCGCCGCCU-CACCA
Tmc.roseum  UAAGCC-UGUAGCAUAUCCUCGG---CUGAACGCUCUGGACGGGGGUUCAACUCCCGCCAGCUCCACCA
Ctb.proteo  UAAGCC-UGUAGACGCGAAAGGU---GGCGGCUCGUCGGACGCGGGUUCGAUUCCCGCCGCCUCCACCA
Her.aurant  UACGCU-UGUAGAUGCUUGCGGU----UUAACUUUUUGGACGCGGGUUCGAUUCCCGCCGCCUCCACCA
Tdb.commun  UAAGCC-UGUAGCGGUUUAAUCU---GAACUAUCUCCGGACGCGGGUUCGAUUCCCGCCGCCUCCACCA
Ver.spinos  UGAGCA-UGGAGACGCUUUCAUA-----AAGGNGUUCGGACAGGG********************
Dcg.thermo  UAAGCU-UGUAGAGGCUUUUGAU---UCUUGCUCUCUGGACGCGGGUUCGAUUCCCGCCGCCUCCACCA ③'
            ══════     ═══════════         ══════════════      ═════
              H2            H5                  H6              H1

+RNA-LIKE DOMAIN H1-H6
```

FIG. 4B

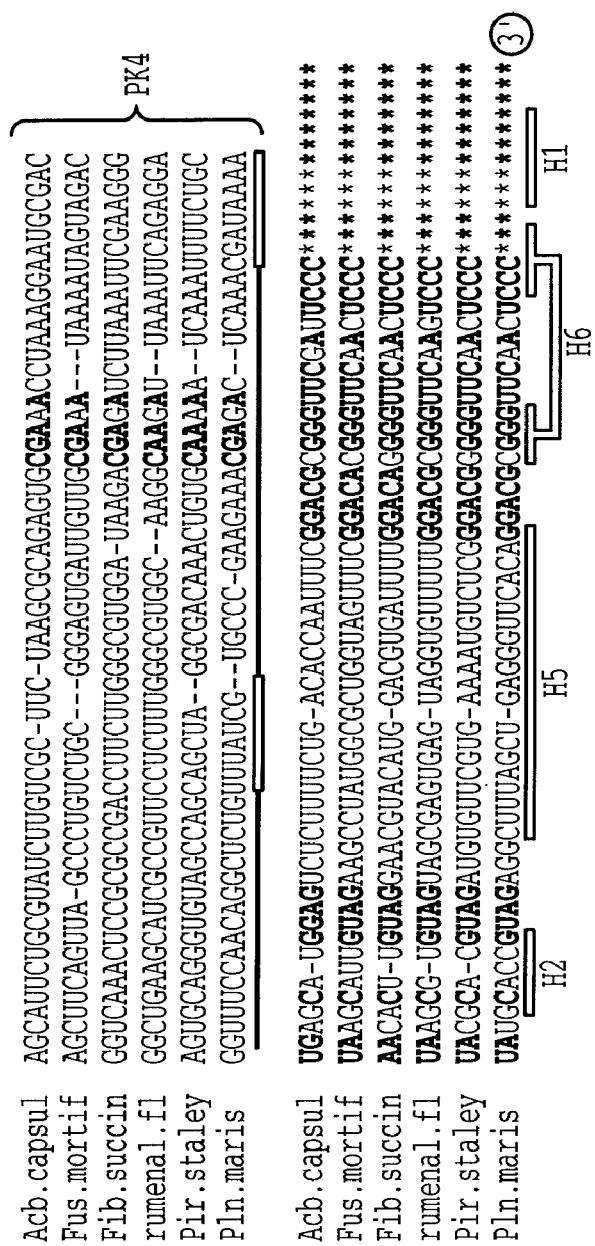

```
Alc.faecal   GCAGUGUUAU-UUACAAAGAAU--C-GAAUCGGUCUGCGCCACGAAGUCCGGUUCUAAAA-CUUAGUGGAU ⎫
Alc.eutrop   GCGAGGUCAU-UUACGUCAGAU--A-AGCUCCGGAAGGGUCACGAAGCCGGGGACGAAAA-CCUAGUGACU ⎪
Ral.picket   GCGAGGUCAU-UUACGUCAGAU--A-AGCUUUAGGUGAGUCACGGGCCUAGAGACGAAAA-CUUAGUGAAU ⎪
Nis.gonorr   GCAACGUCAUCUUACAUUGACU--G-GUUUCCAGCCGGGUUACUUGGCAGGAAAUAAGACUUAAGGUAACU ⎪
Nis.meninS   GCAACGUCAUCUUACAUUGACU--G-GUUUCCUGCCGGGUUAUUUGGCAGGAAAUGAGAUUUAAGGUAACU ⎪
Chb.violac   GUAGUGUCACUCUACAUCUGCU--A-GUGCUGUUCCGGGUUACUUGGUUCAGUGCGAAAUAAUAGGUAACU ⎪
Nms.cryoto   GCAGAGUCAU-UAG-CAAGGAU--C-GCGUUCUGUAGGGUCACUUUACAGAACGUUAAACAAUAGGUGACU ⎬ PK3
Mtb.glycog   GCAGCGUCAU-UAAGAGAGGAU--C-GUGCGAUAUUGGGUUACUUAAUAUCGUAUUAAAUCCAAGGUAACU ⎪
Ps.testost   GCAAGGGAAU-UUUCAUUAGCU--G-GCUGGAUACCGGGCUUCUUGGUAUUUGGCGAUUUUAGGAAGCU ⎪
Vx.paradox   GCAAGGAUAA-CUACAUGGGCU--G-GCUCCGAUCCGGGUACCUUGGGUCGGGGCGAGAAAAUAGGGUACU ⎪
Hph.paller   GCAAGGUAAU-UUACAUCGGCU--G-GUUCUGCGUCGGGCACCUUGGCGCAGGAUGAGAUUCAAGGAUGCU ⎪
Brd.pertus   GCAGCGACAU-UCACAAGGAAU--C GGCCACCGCUGGGGUCACA-CGGCGUUGGUUUAAA-UUACGUGAAU ⎭
                                   PK2

Alc.faecal   CGCCAAGG-AAAGGCCUGUCA-AUUGGCAUAGUCCAAGGUUAAAACUUAAAAUUAAU-UGAC ⎫
Alc.eutrop   CGCCGUCG-UAGAGCGUGUUC-GUCCGCGAUG-CGCCGGUUAAAU---CAAA-UGACAGAAC ⎪
Ral.picket   CGCCGUCG-UAGAGCGUGUUC-GUCCGCGAUG-CGGCGGUUAAAU---CAAA-UGACAGAAC ⎪
Nis.gonorr   GGUUUCCA-AAAGGCCUGUUG-GUCGGCAUGA-UGGAAAUAAGAUUUUCAAAUAGACACAAC ⎪
Nis.meninS   GGUUUCCA-AAAGGCCUGUUG-GUCGGCAUGA-UGGAAAUAAGAUUUUCAAAUAGACACAAC ⎪
Chb.violac   CGCCAAAGUCCA-GCCUGUCC-GUCGGCGUGG-CAGAGGUUAAAUC--CAAA-UGACACGAC ⎪
Nms.cryoto   CGCCUGCC-AUCAGCCCGCCA-GCUGGCGGUU-GUCAGGUUAAAU---UAAA-GAGCAUGGC ⎬ PK4
Mtb.glycog   CGCCUGCU-GUUUGCUUGCUC-GUUGGUGAGC-AUCAGGUUAAAU---CAAA-CAACACAGC ⎪
Ps.testost   GGCUACCCAAGCAGCGUGUGC-CUGCGGGGUUUGGGUGGCGAGAUU--UAAA-ACAGAGCAC ⎪
Vx.paradox   GGCGUCCGGUUUAGCGUGUGA-CUGCGCGACUCCGGAAGCGAGACU--CAAA-ACAGAUCAC ⎪
Hph.paller   GGCUUCCCGUUUAGCGUGCCA-CUGCGCGACUCGGGCGGCGAGACC--CAAA-UCAGACGGC ⎪
Brd.pertus   CGCCCUGG-UCCGGCCCGUCG-AUCGGCUAAGUCCAGGGUUAAAUC--CAAAUAGAU-CGAC ⎭

Alc.faecal   UACACAUGUAGAACUGUCUGUGGACGGCUUGCGGACGGGGGUUCGAUUCCC***********
Alc.eutrop   UAAGUAUGUAGAACUCUCUGUGGAGGGCUUACGGACGCGGGUUCGAUUCCCGCCGGCUCCACCA
Ral.picket   UAAGUAUGUAGAACUCUCUGUGGAGGGCUUGCGGACGCGGGUUCGAUUCCC***********
Nis.gonorr   UAAGUAUGUAGAACGCUUUGUAGAGGACUUUCGGACGGGGGUUCGAUUCCCCCCGCCUCCACCA
Nis.meninS   UAAGUAUGUAGAACGCUUUGUAGAGGACUUUCGGACGGGGGUUCGAUUCCCCCCGCCUCCACCA
Chb.violac   UAAGUAUGUAGAACUCACUGUAGAGGACUUUCGGACGCGGGUUCAACUCCC***********
Nms.cryoto   UAAGUAUGUAGAACUGUCUGUAGAGGACUUGCGGACGCGGGUUCAACUCCC***********
Mtb.glycog   UAAGUAUGUAGAACUGUCUGUGGAGGGCUUGCGGACGGGGGUUCGAUUCCC***********
Ps.testost   UAAACAUGUAGAUCUGUCCGGCGAAGGCUUACGGACGCGGGUUCAAUUCCCGCCGGCUCCA***
Vx.paradox   UAAACAUGUAGAACUGCGCGAUGAAGGCUUGCGGACGGGGGUUCAACUCCC***********
Hph.paller   UACACAUGUAGAACUGCUCGAAAAGGCUUGCGGACGGGGGUUCAACUCCC***********
Brd.pertus   UAAGCAUGUAGAACUGGUUGCGGAGGGCUUGCGGACGGGGGUUCAAUUCCCCCCGGCUCCACCA  ③'
                  H2         H5            H6    H1
```

FIG. 9B

```
              ⑤ ═       H1                    H5              H2
                  ━━━━━━━━━━━━━━━     ═══════════════      ━━━━━━━━━━
Leg.pneumo  ******************CGUGGGUUGCAAAACCGGAAGUGCAUGC
Chr.vinosu  ******************CGUGGGUCGCGAAACCUAAGGUGCAUGC
Dcb.nodosu  **************************CUCGAGGUGCAUGU
Ps.aerugin  GGGGCCGAUU-AGGAUUCGACGCCGGUAACAAAACUUGAGGGGCAUGC
Ps.fluores  ******************CGCCGGUUGCGAACCUUUAGGUGCAUGC
Mar.hydroc  ******************CGCCGGUGACGAACCCUUGGGUGCAUGC
Shw.putref  GGGGGCGAUUCUGGAUUCGACAGGAUUCACGAAACCCUGGGAGCAUGC
Psm.halopl  ******************CGGAAUUCAAGAAGCCCGAGGUGCAUGU
Ae.salmoni  ******************CAAGAUUCACGAAACCCAAGGUGCAUGC
S.typhimur  GGGGCUGAUUCUGGAUUCGACGGGAUUUGCGAAACCCAAGGUGCAUGC
E.coli      GGGGCUGAUUCUGGAUUCGACGGGAUUUGCGAAACCCAAGGUGCAUGC
Yer.pestis  GGGGCUGAUUCUGGAUUCGACGGGAUUCGCGAAACCCAAGGUGCAUGC
V.cholerae  GGGGCUGAUUCAGGAUUCGACGGGAAUUUUGCAGUCUGAGGUGCAUGC
H.influenz  GGGGCUGAUUCUGGAUUCGACGGGAUUAGCGAAGCCCAAGGUGCACGU
H.actinomy  GGGGCUGAUUCUGGAUUCGACGGGAUUAGCGAAGCCCGAAGUGCACGU
                                      PK1
                              ┌─────────────┐
Leg.pneumo  CGAG-AAGGAGAUC-UCUCGUAAAUA-AGA-CUCAAUUA-AAU
Chr.vinosu  CGAG-GUGCGGUUGACCUCGUAAAAC--CCUCCGCAAA--CUU
Dcb.nodosu  CGAG-AAUGAGAGAAUCUCGUUAAAU--ACUUUCAAAA--CUU
Ps.aerugin  CGAGCUGGUAGCAGAACUCGUAAAUUCGCUGCUGCAAA--CUU
Ps.fluores  CGAGUUGGUAACAGAACUCGUAAAUCCACUGUUGCAACUUUCU
Mar.hydroc  CGAGAUGGCAGCGAAUCUCGUAAAUCCAAAGCUGCAAC--GUA
Shw.putref  CGAG-GGGCGGUUGGCCUCGUAAA----AAGCCGCAAA--GUU
Psm.halopl  CGAG-GUGCGGUUUGCCUCGUAAAA---AAGCCGCAAUU-UAA
Ae.salmoni  CGAG-GUGCGGUAGGCCUCGUUAAC---AAACCGCAAA--AAA
S.typhimur  CGAG-GGGCGGUUGGCCUCGUAAA----AAGCCGCAAA--AAA
E.coli      CGAG-GGGCGGUUGGCCUCGUAAA----AAGCCGCAAA---AA
Yer.pestis  CGAG-GUGCGGUG-GCCUCGUAAA----AAACCGCAAA-AAAA
V.cholerae  CGAG-GUGCGGUAGGCCUCGUUAAC---AAACCGCAAA--AAA
H.influenz  CGAG-GUGCGGUAGGCCUCGUAAAU---AAACCGCAAA--AAA
H.actinomy  CGAG-GUGCGGUAGGCCUCGUAAAU---AAACCGCAAA--AAA
                                                          CODING SEQUENCE
                                                                ↓
            ┌──────────────────────────────────────────────┐
Leg.pneumo  A-UAAAU gcaaacgaugaaaacuuugcugguggggaagcuaucgcugcc UAA-----UAAGCACUUU
Chr.vinosu  A-UAGUU gccaacgacgacaacuac-------------gcucucgcugcu UAA-----UCCCAGCGGG
Dcb.nodosu  A-UAGUU gcaaacgacgacaacuac-------------gcuuuagcgggcu UAA-----UUCCCGCUUU
Ps.aerugin  A-UAGUU gccaacgacgacaacuac-------------gcucuagcugcu UAA------UGCGGCUAG
Ps.fluores  A-UAGUU gccaaugacgaaaccuac---ggggaauacgcucucgcugcg UAA-------GCAGCCUU
Mar.hydroc  A-UAGUC gcaaacgacgaaacuac-------------gcacuggcggcg UAA---GCCGUU-CCAGU
Shw.putref  A-UAGUU gcaaacgacgauaacuac-------------gcucuagccgcu UAA------UGCCGCUAG
Psm.halopl  AGUAAUC gcaaacgacgauaacuac-------------ucucuagcagcu UAG------GCUGGCUAG
Ae.salmoni  A-UAGUC gcaaacgacgaaaacuac-------------gcacuagcagcu UAAUAACCUGCAUAGAGC
S.typhimur  A-UAGUC gcaaacgacgaaaccuac-------------gcuuuagcagcu UAAUAACCUGCUUAGAGC
E.coli      A-UAGUC gcaaacgacgaaaccuac-------------gcuuuagcagcu UAAUAACCUGCUUAGAGC
Yer.pestis  A-UAGUU gcaaacgacgaaaacuac-------------gcacuagcagcu UAAUAACCUGCUUAGAGC
V.cholerae  A-UAGUC gcaaacgacgaaaacuac-------------gcacuagcagcu UAAUACCCUGCUCAGAGC
H.influenz  A-UACUC gcaaacgacgaacaauac-------------gcuuuagcagcu UAAUAACCUGCAUUUAGC
H.actinomy  A-UAGUC gcaaacgacgaacaauac-------------gcuuuagcagcu UAAUAACCUGCCUUUAGC
                                                                  ══════  ════
                                                                       H4
```

FIG. 10A

```
Leg.pneumo  AGUUAAACCAUCACUGUGUACUGGCCAAUAAACCCAGUAUC
Chr.vinosu
Dcb.nodosu
Ps.aerugin
Ps.fluores  AGCCCUUCCCUCCUGGUACCUUCGGGUCCAG
Mar.hydroc
Shw.putref
Psm.halopl
Ae.salmoni
S.typhimur
E.coli
Yer.pestis
V.cholerae
H.influenz
H.actinomy Leg.pneumo  CCGUUCG-ACCGAGCCC--GCUUAUC-GGUAUCGAA-------UCAACGGUCAU-AAGAGAU-AAGCU
Chr.vinosu  CCUCUGA-CCGUCACUU--GCCUGUGGGCGGCGGAUU------CCAGGGGUAAC-CUCACAC-AGGAU
Dcb.nodosu  CGCUUAC-CUAGAUUU---GUCUGUGGGUUUACC---------GUAAGCGACAU--UAACAC-AGAAU
Ps.aerugin  CAGUCGC-UAGGGGAU---GCCUGUAAACCCGAAA--------CGACUGUCAG-AUAGAAC-AGGAU
Ps.fluores  CAAUCAU-CAGGGGAU---GUCUGUAAACCCAAAG--------UGAUUGUCAU-AUAGAAC-AGAAU
Mar.hydroc  CGUCCUG-GCUGAGGC---GCCUAUAACUCAGUAGCAACAUCCCAGGACGUCAU-CGCUUAU-AGGCU
Shw.putref  CCAUCUA-CCACACGCUUUGCACAUGGGCAGUGGAUU-------UGAUGGUCAU-CUCACAUCGUGCU
Psm.halopl  CGCUCCU-UCCAUGUAU--UCUUGUG-GACUGGAUUUU------GGAGUGUCACCCUAACAC-CUGAU
Ae.salmoni  CCUUCUA-CCCUAGCUU--GCCUGUGUCCUAGGGAAUC------GGAAGGUCAU-CCUUCAC-AGGAU
S.typhimur  CCUCUCU-CCCUAGCCUCCGCUCUUAGGACGGGGAUCA-----AGAGAGGUCAAACCCAAAA-GAGAU
E.coli      CCUCUCU-CCCUAGCCUCCGCUCUUAGGACGGGGAUCA-----AGAGAGGUCAAACCCAAAA-GAGAU
Yer.pestis  CCUCUCU-CCCUAGCCUCCGCUCUUAGGACGGGGAUCA-----AGAGAGGUCAAACCUAAAA-GAGCU
V.cholerae  CCUUCCU-CCCUAGCUUCCGCUUGUAAGACGGGGAAAUC----AGGAAGGUCAAACCAAAUC-AAGCU
H.influenz  CUUCGCG-CUCCAGCUUCCGCUCGUAAGACGGGGAUAA-----CGCGGAGUCAAACCAAAAC-GAGAU
H.actinomy  CUUCGCU-CCCCAGCUUCCGCUCGUAAGACGGGGAUAA-----AGCGGAGUCAAACCAAAAC-GAGAU
                                                              PK2
```

FIG. 10B

```
                        PK3
            ┌─────────────────────────────────────────────────────────────────┐
Leg.pneumo  -AGCG-UCCU-AAUCU--AUCCC-GGGUU-AUGG-CGCGAAA-CU-CA--GGGAAU
Chr.vinosu  -CGUG-GUGA-CGGGA--GUCCG-GACCU-GAUC-CACUAAAACC-UA-ACGGAAU
Dcb.nodosu  -CGCU-GGUU-AACG--CGUCCGC-UGUU-AAUC-GGUUAAA-UU-AA-GCGGAAU
Ps.aerugin  -CGCC-GCCA-AGUU--CGCUGUA-GACG-UAAC-GGCUAAAACU-CA-UACAGCU
Ps.fluores  -CGCC-GUGC-AGUA--CGUUGUG-GACG-AAGC-GGCUAAAACU-UA-CACAACU
Mar.hydroc  GCUCC-GUUC-ACCAG-AGCUCA-CUGGU-GUUC-GGCUAAG-AU-UA-AAGAGCU
Shw.putref  -AGCGAGGGA-ACCC--UGUCUGG-GGGU-GAAC-CGCGAAACAG-UA-CCGGACU
Psm.halopl  -CGCGACGGA-AACCC-UGGCCG-GGGUU-GAAG-CGUUAAAACU-AA-GCGGCCU
Ae.salmoni  -CGUG-UGGA-AGUCC-UGCUCG-GGGCG-GAAG-CAUUAAAACC-AA-UCGAGCU
S.typhimur  -CGCG-CGGA-UGCCC-UGCCUG-GGGUU-GAAG-CGUUAAAACG-AA-UCAGGCU
E.coli      -CGCG-UGGA-AGCCC-UGCCUG-GGGUU-GAAG-CGUUAAAACUUAA-UCAGGCU
Yer.pestis  -CGUG-UGGA-AACCU-UGCCUG-GGGUG-GAAG-CAUUAAAACU-AA-UCAGGAU
V.cholerae  -GGCG-UGGA-UUCCCCCACCUGA-GGGAUGAAG-CGCGAGAUCU-AAUUCAGGUU
H.influenz  -CGUG-UGGA-AGCCACCGUUUGA-GGAUCGAAG-CACUAAAUUG-AA-UCAAACU
H.actinomy  -CGUG-UGGA-AGCCACCGUUUGA-GGAUCGAAG-CAUUAAAUUA-AA-UCAAAGU ┌─────────────────────────────────────────────────────────────────┐
Leg.pneumo  CGCUGUGUAU-CAUCCUGCCC-GUCGGAGGAGCCACAGUUAAAUUCAAAAGACAAGGC--  ┐
Chr.vinosu  CGCCGACUGAUCGCCCUGCCC-UUCGGGCGGCAGAAGGCUAAAAACAAUAGAGUGGGC--  │
Dcb.nodosu  CGCUUGUAAA-AUGCCUGAGC-GUUGGCUGUUUAUGAGUUAAACCUAAUUAACUGCUC--  │
Ps.aerugin  CGCUCCAAGC--ACCCUGCCA-CUCGGGCGGCGCGGAGUUAA-CUCAGUAGAGCUGGC--  │
Ps.fluores  CGCCCAAAGC--ACCCUGCCC-GUCGGGUCGCUGAGGGUUAA-CUUAAUAGACACGGC--  │
Mar.hydroc  CGCCUCUUGC--ACCCUGACC-UUCGGGUCGCUUGAGGUUAA-AUCAAUAGAA-GGACAC  │
Shw.putref  CACCGUGUGG-GAUCCUGUCU-UUCGGAGUUCAAACGGUUAA-ACAAUA-GAA-AGAC--  │
Psm.halopl  CGCCUUUAUC-UACCGUGUUU-GUCCGGGAUUUAAAGGUUAA-UUAAAU-GACAAUAC--  ├PK4
Ae.salmoni  AGUCAAUUCG-UGGCGUGUCU-CUCCGCAGCGGGUUGGCGAA-UGUAAA-GAG-UGAC--  │
S.typhimur  AGUCUGGUAG-UGGCGUGUCC-GUCCGCAGGUGCCAGGCGAA-UGUAAA-GAC-UGAC--  │
E.coli      AGUUUGUUAG-UGGCGUGUCC-GUCCGCAGCUGGCAAGCGAA-UGUAAA-GAC-UGAC--  │
Yer.pestis  AGUUUGUCAG-UAGCGUGUCC-AUCCGCAGCUGGCCGGCGAA-UGUAAU-GAUUGGAC--  │
V.cholerae  AGCCAUUCGU-UAGCGUGUCG-GUUCGCAGGCG-GUGGUGAA-AUUAAA-GAU-CGAC--  │
H.influenz  AGCUUAAGUU-UAGCGUGUCU-GUCCGCA-UGCUUAAGUGAA-AUUAAA-GACGAGAC--  │
H.actinomy  AGCUUAAUUG-UCGCGUGUCC-GUCAGCA-GGAUUAAGUGAA-UUUAAA-GACCGGAC--  ┘

Leg.pneumo  UAUGCAUGUAGAGCUAAAGGCAGAGGACUUGCGGACGCGG**********************
Chr.vinosu  UAAGCAUGUAGGACCGAGGGCAGAGGGCUUGCGGACGCGG**********************
Dcb.nodosu  UAAACAUGUAGUACCAAAAGUUAAGGAUUCGCGGACGGGGGUUCAAAUCCCCCGCCUCCACCA
Ps.aerugin  UAAGCAUGUAGAACCGAUAGCGGAGAGCUGGCGGACGGGGGUUCAAAUCCCCCGGCUCCACCA
Ps.fluores  UACGCAUGUAGUACCGACAGCAGAGUACUGGCGGACGGGG**********************
Mar.hydroc  UAAGCAUGUAGACCUCAAGGCCUAGUGCUGGCGGACGCGG**********************
Shw.putref  UAAGCAUGUAGCGCCUUGGAUGUAGGUUUUCUGGACGCGGGUUCAAGUCCCGCCGCCUCCACCA
Psm.halopl  UAAACAUGUAGUACCGACGGUCGAGGCUUUUCGGACGGGG**********************
Ae.salmoni  UAAGCAUGUAGUACCGAGGAUGUAGUAAUUUGGACGGGG***********************
S.typhimur  UAAGCAUGUAGUACCGAGGAUGUAGGAAUUUCGGACGCGGGUUCAACUCCCGCCAGCUCCACCA
E.coli      UAAGCAUGUAGUACCGAGGAUGUAGGAAUUUCGGACGCGGGUUCAACUCCCGCCAGCUCCACCA
Yer.pestis  UAAGCAUGUAGUGCCGACGGUGUAGUAAUUUCGGACGGGGGUUCAAAUCCCCCAGCUCCACCA
V.cholerae  UAAGCAUGUAGUACCAAAGAUGAAUGGUUUUCGGACGGGGGUUCAACUCCCCCCAGCUCCACCA
H.influenz  UAAACGUGUAGUACUGAAGGUAGAGUAAUUUCGGACGGGGGUUCAACUCCCCCCAGCUCCACCA
H.actinomy  UAAACGUGUAGUGCUAACGGCAGAGGAAUUUCGGACGGGGGUUCAACUCCCCCCAGCUCCACCA ③
            ──────        ─────────          ────────          ─────
              H2              H5                H6                H1
```

EUBACTERIAL TMRNA SEQUENCES AND USES THEREOF

CROSS-REFERENCE TO RELATED APPLICATIONS

The present application is division of U.S. patent application Ser. No. 11/329,230 filed on 11 Jan. 2006, which in turn in a division of U.S. patent application Ser. No. 09/958,206 filed on 20 Feb. 2002, now U.S. Pat. No. 7,115,366, which in turn is a national stage filing under 35 U.S.C. §371 of International patent application No. PCT/US00/08988 filed on 6 Apr. 2000, which in turn is related to and claims priority under 35 U.S.C. §119(e) to U.S. provisional patent application Ser. No. 60/128,058 filed on 7 Apr. 1999. Each of these applications is incorporated herein by reference.

This application was made with Government support under Grant No. GM 48152, funded by the National Institutes of Health, Bethesda, Md. The Government has certain rights in this invention.

BACKGROUND OF THE INVENTION

The present invention is directed to eubacterial tmDNA sequences and the corresponding tmRNA sequences. The present invention is further directed to alignments of eubacterial tmDNA sequences and use of the sequences and sequence alignments for the development of antibacterial drugs. The present invention is also directed to the use of the sequences for the development of diagnostic assays.

The publications and other materials used herein to illuminate the background of the invention or provide additional details respecting the practice are incorporated by reference, and for convenience are respectively grouped in the appended List of References.

Eubacterial tmRNAs (10Sa RNAs) are unique since they function, at least in *E. coli*, both as tRNA and as mRNA (for a review, see Muto et al., 1998). These ≈360±10% nucleotide RNAs are charged with alanine at their 3'-ends (Komine et al., 1994; Ushida et al., 1994) and also have a short reading frame coding for 9 to 27 amino acids depending on the bacterial species. *E. coli* tmRNA mediates recycling of ribosomes stalled at the end of terminatorless mRNAs, via a trans-translation process (Tu et al., 1995; Keiler et al., 1996; Himeno et al., 1997). In *E. coli*, this amino acid tag is co-translationally added to polypeptides synthesized from mRNAs lacking a termination codon, and the added 11 amino acid C-terminal tag makes the protein a target for specific proteolysis (Keiler et al., 1996).

Structural analyses based on phylogenetic (Felden, et al., 1996; Williams and Bartel, 1996) and probing (Felden et al., 1997; Hickerson et al., 1998) data have led to a compact secondary structure model encompassing 6 helices and 4 pseudoknots. tmRNAs have some structural similarities with canonical tRNAs, especially with tRNA acceptor branches. *E. coli* tmRNA contains two modified nucleosides, 5-methyluridine and pseudouridine, located in the tRNA-like domain of the molecule, in a seven-nucleotide loop mimicking the conserved sequence of T loops in canonical tRNAs (Felden et al., 1998).

Fifty-three tmRNA sequences are now known from both experimental data and Blast searches on sequenced genomes (summarized in Williams, 1999; Wower and Zwieb, 1999). These sequences cover only 10 phyla, less than one third of the known bacterial taxa. It is desired to determine additional tmRNA sequences and to use the tmRNA sequences for drug development.

SUMMARY OF THE INVENTION

The present invention relates to eubacterial tmDNA sequences and the corresponding tmRNA sequences. The present invention further relates to alignments of eubacterial tmDNA sequences and use of the sequences and sequence alignments for the development of antibacterial drugs.

In one aspect of the present invention, an extensive phylogenetic analysis was performed. Fifty-eight new tmDNA sequences including members from nine additional phyla were determined. Remarkably, tmDNA sequences could be amplified from all species tested apart from those in the alpha-Proteobacteria. This aspect of the invention allowed a more systematical study of the structure and overall distribution of tmRNA within eubacteria In a second aspect of the invention, alignments are made with the newly isolated tmDNA sequences and previously disclosed tmRNA sequences.

In a third aspect of the invention, the alignments of the tmRNA sequences allow the identification of targets for development of antibacterial drugs.

In a fourth aspect of the invention, the novel tmDNA or tmRNA sequences of the present invention are used to develop diagnostic assays, such as amplification-based assays, for the bacterial species disclosed herein.

BRIEF DESCRIPTION OF THE FIGURES

FIGS. 3A, 3B and 3C show the sequence alignment, structural domains and structural features for the tmRNA of several species of Firmicutes. The tmRNA sequences are set forth in SEQ ID NOs:67-87.

FIGS. 4A and 4B show the sequence alignment, structural domains and structural features for the tmRNA of several species of Thermophiles. The tmRNA sequences are set forth in SEQ ID NOs:88-99.

FIGS. 7A-1, 7A-2, 7B, 7C and 7D show the sequence alignment, structural domains and structural features for the tmRNA of several species of Mesophiles (7A-1, 7A-2, 7C, 7D) and environmental sludge (7B). The tmRNA sequences of the Mesophiles are set forth in SEQ ID NOs:118-123 and 125-128, and the tmRNA sequence of the environmental sludge is set forth in SEQ ID NO:124. The tmRNA sequences of several species of Clamydia are set forth in SEQ ID NOs:129-131.

FIGS. 9A and 9B show the sequence alignment, structural domains and structural features for the tmRNA of several species of Pourpres beta. The tmRNA sequences are set forth in SEQ ID NOs:143-154.

FIGS. 10A, 10B and 10C show the sequence alignment, structural domains and structural features for the tmRNA of several species of Pourpres gamma. The tmRNA sequences are set forth in SEQ ID NOs:155-169.

Figure 11A:
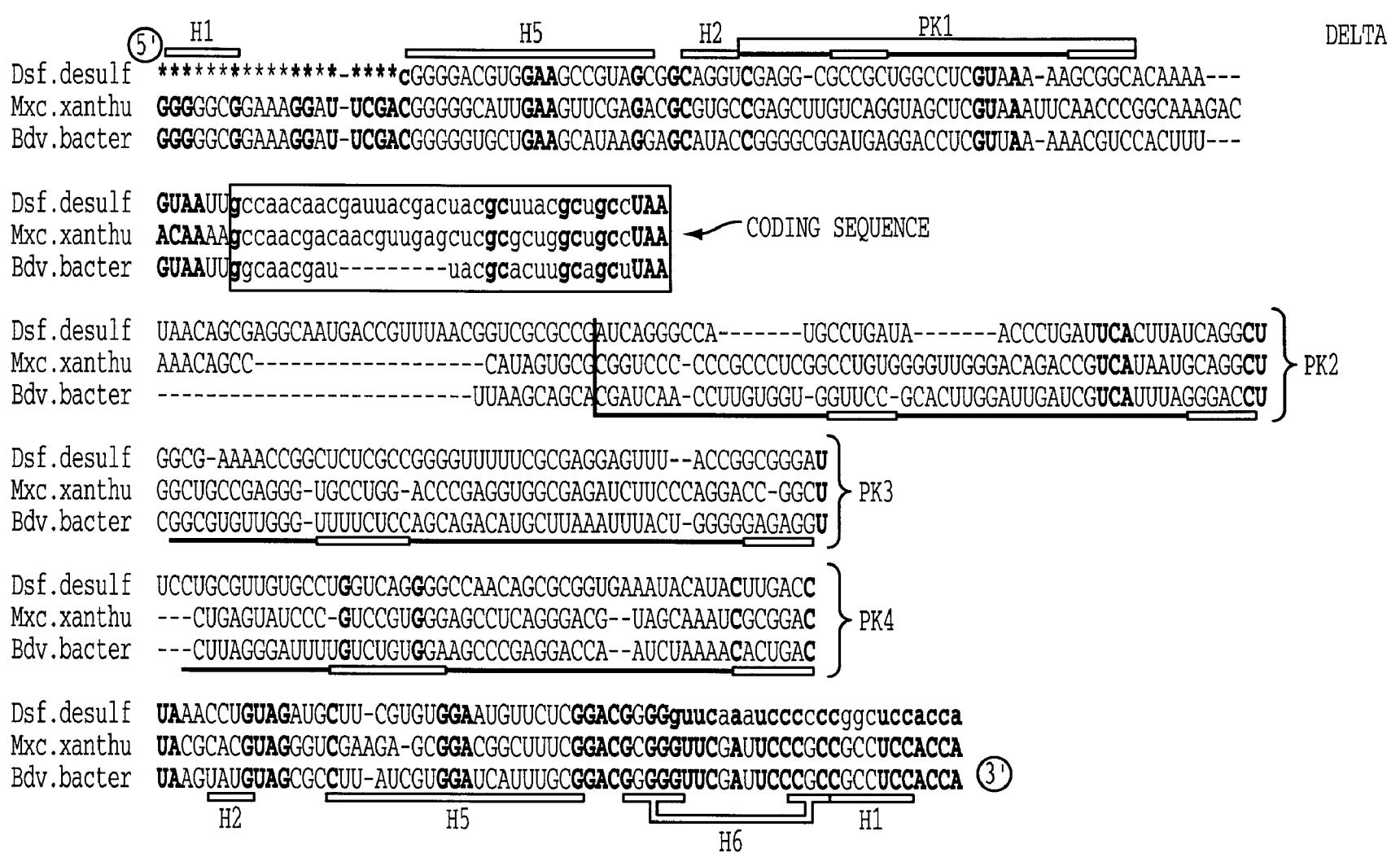

FIGS. 11A and 11B show the sequence alignment, structural domains and structural features for the tmRNA of several species of Pourpres delta (11A) and Pourpres epsilon (11B). The tmRNA sequences of the Pourpres delta are set forth in SEQ ID NOs:170-172, and the tmRNA sequences of the Pourpres epsilon are set forth in SEQ ID NOs:173-175.

DETAILED DESCRIPTION OF THE INVENTION

Figure 1B:
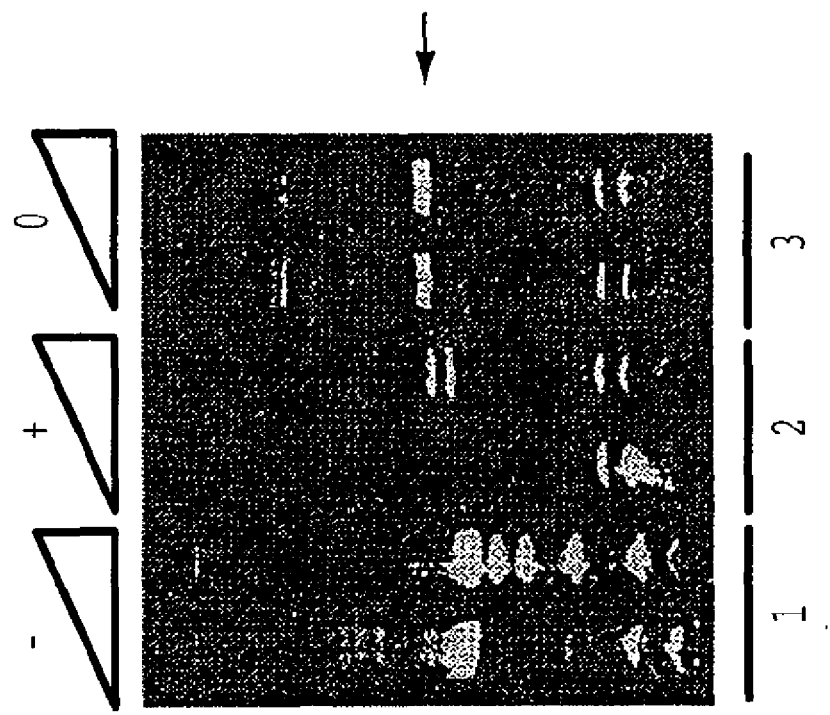
FIGS. 1A-1B show the effect of the annealing temperature (FIG. 1A) and magnesium concentration (FIG. 1B) on amplifying eubacterial tmRNA genes from genomic DNAs using PCR. A: Varying the annealing temperature from 50° to 70° C. during the PCR amplification of *Thermus aquaticus* (1). B; Varying the magnesium concentration to amplify tmDNA genes from *Thermus aquaticus* (1), negative effect of increasing the magnesium concentration), *Acholeplasma laidlawii* (2), positive effect of increasing the magnesium concentration, the upper band is the tmDNA gene) and from *Mycoplasma salivarium* (3), no discernible effect of magnesium ions in that concentration range). The arrows point toward the 4 novel tmDNA genes that have been sequenced.

The present invention is directed to eubacterial tmDNA sequences and the corresponding tmRNA sequences. The present invention is further directed to alignments of eubacterial tmDNA sequences and use of the sequences and sequence alignments for the development of antibacterial drugs.

The novel eubacterial tmDNA sequences determined in accordance with the present invention are set forth in Tables 1-58, below. The alignment of tmRNA sequences is shown in FIGS. 3A-11B, which also show the structural domains and structural features of the tmRNA. The present invention also includes the tmRNA sequences set forth in these figures to the extent they differ from the sequences set forth in Tables 1-58.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria. Thus, the present invention is further directed to the development of drugs for the therapeutic treatment of bacteria, generically or specifically. Suitable drugs are developed on the basis of the tmRNA sequences as described herein.

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. Since these pseudoknots are not found in all canonical transfer RNAs, they can also be targeted with specific drugs. Disruption of either PK1 or PK2 or PK3 with a specific drug would lead to inactive tmRNA molecules in vivo.

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding (such as shown for *Escherichia coli*; Matveeva et al., 1997), and thus, is also available for interaction with other drugs. Moreover, the coding sequence is a critical functional domain of the molecule in its quality-control mechanism in cells.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 basepairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

It has recently been discovered that even the alpha-proteobacteria possess tmRNA genes. These genes are permuted and are made in two parts, connected via a processed linker. These tmRNA gene sequences from alpha-proteobacteria were not found in the course of the present invention because usual PCR methods could not amplify them.

Recent reports have shown that whereas the gene encoding tmRNA is non-essential in *E. coli* (does not kill the bacteria when disrupted), it is indeed essential in *Neisseria gonor-*

*rheae* (Huang et al., 2000). Also, tmRNA is directly involved in *Salmonella typhymurium* pathogenticity (Julio et al., 2000).

In summary, tmRNA genes are present in all eubacterial genomes, with no exceptions, but are not present in any genomes from archebacteries or eukaryotes, with the exception of some chloroplasts. The very specific location of tmRNA genes within one of the three main kingdoms of life make them ideal targets for the design of novel antibiotics that will, in principle, interfere very weakly with human biochemistry, compared to usual antibiotics. For a recent review about designing novel antibiotics, see Breithaupt (1999).

The present invention is also directed to diagnostic assays and kits for the detection of bacterial infection, particularly infections caused by bacterial agents disclosed herein. In one embodiment, the coding sequence of each bacterial species is used to design specific primers for use in amplification-based diagnostic assays for infectious diseases. Specific primers are designed in accordance with well known techniques, and such design is readily done by a skilled artisan. Amplification-based diagnostic assays are performed in accordance with conventional techniques well known to skilled artisans. Examples of amplification-based assays include, but are not limited to, polymerase chain reaction (PCR) amplification, strand displacement amplification (SDA), ligase chain reaction (LCR) amplification, nucleic acid sequence based amplification (3SR or NASBA) and amplification methods based on the use of Q-beta replicase.

Drugs which target the sequences described herein are active agents can be formulated in pharmaceutical compositions, which are prepared according to conventional pharmaceutical compounding techniques (Remington's, 1990). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences* (18).

Alternatively, targeting therapies may be used to deliver the active agent more specifically to certain types of cell, by the use of targeting systems such as antibodies or cell-specific ligands. Targeting may be desirable for a variety of reasons, e.g. if the agent is unacceptably toxic, or would otherwise require too high a dosage, or otherwise be unable to enter the target cells.

Antisense active agents can also be delivered by techniques described in U.S. Pat. Nos. 5,811,088; 5,861,290 and 5,767,102.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

1. Extraction of Genomic DNA

Bacterial genomic DNAs were prepared from ≈10 mg freeze-dried cells provided from ATCC (American Type Culture Collection, Virginia, USA). Cell pellets were resuspended in 750 µL of lysis buffer (50 mM Tris (pH 8.0), 50 mM EDTA and 20% sucrose). 150 µL of a 10 mg/mL solution of lysozyme was mixed and let stand at room temperature for 15 min. 150 µL of 1% SDS was added and let stand at room temperature for 15 minutes. Four to five phenol/chloroform extractions were performed, until the sample was clear and there was no interphase. Two to five µL of a 10 mg/mL solution of RNase DNase-free was added and incubated at room temperature for 30 minutes. After a phenol/chloroform extraction of the enzyme, the genomic DNA was precipitated with 1/10 volume of 3M NaOAc (pH 5.5) and 1 volume isopropanol, and stored at −20° C. for 2 hours. After centrifugation, the genomic DNAs were washed with 70% ethanol, vacuum-dried and diluted in sterile water to a final concentration of 10 ng/µL.

2. Primer Sets for PCR Reactions

The following primer sets were used during the PCR:
primer set A (based on *E. coli* tmRNA termini):

```
5'-GGG GCT GAT TCT GGA TTC GAC-3'    (SEQ ID NO: 1)
and
5'-TGG AGC TGG CGG GAG TTG AAC-3';   (SEQ ID NO: 2)
``` primer set B (based on *T. neapolitana* tmRNA termini):

```
5'-GGG GGC GGA AAG GAT TCG ACG-3'    (SEQ ID NO: 3)
and

5'-TGG AGG CGG CGG GAA TCG AAC-3';   (SEQ ID NO: 4)
``` primer set C (based on *M. pneumoniae* tmRNA termini):

```
5'-GGG GAT GTC ATG GTT TTG ACA-3'    (SEQ ID NO: 5)
and

5'-TGG AGA TGG CGG GAA TCG AAC-3';   (SEQ ID NO: 6)
``` primer set D (based on *C. tepidum* tmRNA termini):

```
5'-GGG GAT GAC AGG CTA TCG ACA-3'    (SEQ ID NO: 7)
and

5'-TGG AGA TGG CGG GAC TTG AAC-3'.   (SEQ ID NO: 8)
```

3. PCR Reaction

Sequences of tmRNA genes were obtained by polymerase chain reaction (PCR) in 25 µL using 40 ng of genomic DNA per reaction. The following general scheme was utilized for all of the sequences:

(a) 94° C. to 96° C. for 4 min. (first denaturation of genomic DNAs, done only once); then (b) 35 to 40 PCR cycles with 2.5 to 5 Units of Taq DNA polymerase in a 25 µL reaction volume, according to the following scheme (40 ng of genomic DNAs/PCR reaction):
1. denature at 94° to –96° C. for 25 to 30 sec;
2. anneal at 44° to 55° C. for 20 to 30 sec; and
3. extension at 72° C. for 10 sec.

The magnesium conc. was optimized for each phyla from 3.5 to 13.5 mM.

4. Elution of Amplified DNAs

The various PCR-amplified tmDNA bands were gel purified (5% PAGE), stained (ethidium bromide staining), cut using a sterile razor blade, and shaken over-night (passive elution, using a vibrator) in a 350 µl solution containing 10 mM Tris-HCl buffer (pH 8.1). The following day, the PCR amplified tmDNAs were ethanol precipitated, washed in 70% ETOH, vacuum dried and the DNA pellets were dissolved in 18 µl of RNase-DNase free sterile water.

5. DNA Sequencing

Six µL of amplified DNAs were added to 3.2 picomoles of the primer that was used in the PCR. To verify the novel tmDNA sequences, each of the two primers were used independently to sequence each of the two PCR-amplified DNA strands. Some tmDNAs were already engineered at their 5'-ends with a T7 promoter, to be able to transcribe directly the tmDNAs into tmRNAs by in vitro transcription.

Dye terminator sequencing was achieved at the DNA sequencing facility of the Human Genetics Institute. In addition to novel tmRNA sequences that are not available publicly, several tmDNA sequences that were already known have been verified and several sequencing mistakes have been found and corrected (especially for *Alcaligenes eutrophus* tmRNA).

Example 2

Amplification Reactions for Eubacterial tmDNA

Eubacterial tmDNA was amplified by PCR in accordance with Example 1, using the following conditions.

Acidobacterium:
  Primer Set B; Annealing temp. during PCR: 53° C. for 20 sec; $Mg^{2+}$ conc.: 4.5 mM.

Coprothermobacter:
  Primer Set B; Annealing temp. during PCR: 55° C. for 30 sec; $Mg^{2+}$ conc.: 5.5 mM.

Cytophagales:
  Primer Set A; Annealing temp. during PCR: 46° C. for 30 sec; $Mg^{2+}$ conc.: 4.5 mM.

Dictyoglomus:
  Primer set B; Annealing temp. during PCR: 55° C. for 30 sec; $Mg^{2+}$ conc.: 4.5 mM.

Environmental samples:
  Sludge DNA
    Primer set C; Annealing temp. during PCR: 51° C. for $20^{sec}$; $Mg^{2+}$ conc.: 13.5 mM.
  Rumenal fluid DNA
    Primer set D; Annealing temp. during PCR: 50° C. for 30 sec; $Mg^{2+}$ conc.: 9.5 mM.

Fibrobacter:
  Primer set A; Annealing temp. during PCR: 51° C.; $Mg^{2+}$ conc.: 3.5 mM.

Firmicutes:
  Fusobacteria:
    Primer set A; Annealing temp. during PCR: 52° C.; $Mg^{2+}$ conc.: 5.5 mM.
  High G-C:
    Primer set A; Annealing temp. during PCR: 50-55° C.; $Mg^{2+}$ conc.: 4.5 mM.
  Low G-C:
    Primer sets A or B; Annealing temp. during PCR: 52° C.; $Mg^{2+}$ conc.: 5.5 to 7.5 mM.
  Mycoplasmes:
    Primer set A; Annealing temp. during PCR: 52° C.; $Mg^{2+}$ conc.: 3.5 to 5.5 mM.

Green non-sulfur:
  Primer sets A or B; Annealing temp. during PCR: 46 to 52° C.; $Mg^{2+}$ conc.: 4.5 mM.

Green sulfur:
  Primer set A; Annealing temp. during PCR: 46° C.; $Mg^{2+}$ conc.: 4.5 mM.

Planctomycetales:
  Primer set A; Annealing temp. during PCR: 48 to 52° C.; $Mg^{2+}$ conc.: 7.5 mM.

Proteobacteria:
  beta:
    Primer sets A and/or B; Annealing temp. during PCR: 50° C. for 25 sec; $Mg^{2+}$ conc.: 3.5 mM.
  delta:
    Primer set B; Annealing temp. during PCR: 55° C.; $Mg^{2+}$ conc.: 3.5 to 4.5 mM.
  epsilon:
    Primer set A; Annealing temp. during PCR: 46° C. for 30 sec; $Mg^{2+}$ conc.: 3.5 mM.
  gamma:
    Primer set A; Annealing temp. during PCR: 44 C for 30 sec; $Mg^{2+}$ conc.: 5.5 mM.

Spirochetes:
  Primer set A; Annealing temp. during PCR: 52° C.; $Mg^{2+}$ conc.: 4.5 mM.

Thermodesulfobacterium:
  Primer set B; Annealing temp. during PCR: 55° C.; Mg$^{2+}$ conc.: 5.5 mM.

Thermotogales:
  Primer set B; Annealing temp. during PCR: 46° C.; Mg$^{2+}$ conc.: 7.5 mM.

Deinococcales:
  Primer set B; Annealing temp. during PCR: 52° C.; Mg$^{2+}$ conc.: 3.5 mM.

Verrucomicrobia:
  Primer set A; Annealing temp. during PCR: 53° C. for 25 sec; Mg$^{2+}$ conc.: 3.5 mM.

Example 3

Amplification of Eubacterial tmDNA

Figure 1A:
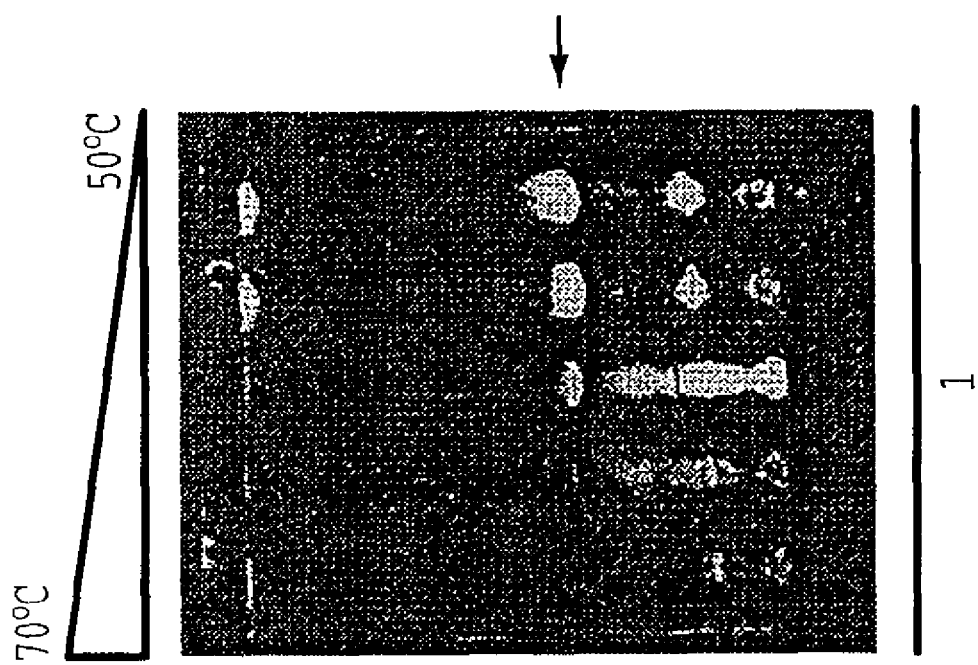

Specific PCR amplification of tmRNA genes was achieved for both thermophilic and mesophilic eubacterial tmRNA genes. For the novel tmDNA genes found in thermophiles, both the magnesium concentration and the annealing temperature (FIG. 1A) were optimized. As shown in FIG. 1A, a specific amplification of *Thermus aquaticus* tmDNA was observed with an annealing temperature around 50° C., whereas at higher temperatures there is a gradual decrease in the amount of amplified tmDNA. For mesophiles, the magnesium concentration during PCR was critical (FIG. 1B), but the annealing temperature could vary from 44° C. to 60° C. without significant effects on the amplification. FIG. 1B shows various effects of increasing the magnesium concentration on the PCR amplification of three novel eubacterial tmDNA genes. Increasing magnesium concentration from 3.5 mM to 5.5 mM has either a negative (FIG. 1B, panel 1), a positive (FIG. 1B, panel 2) or no effect on specifically amplifying eubacterial tmDNA genes.

Figure 2:
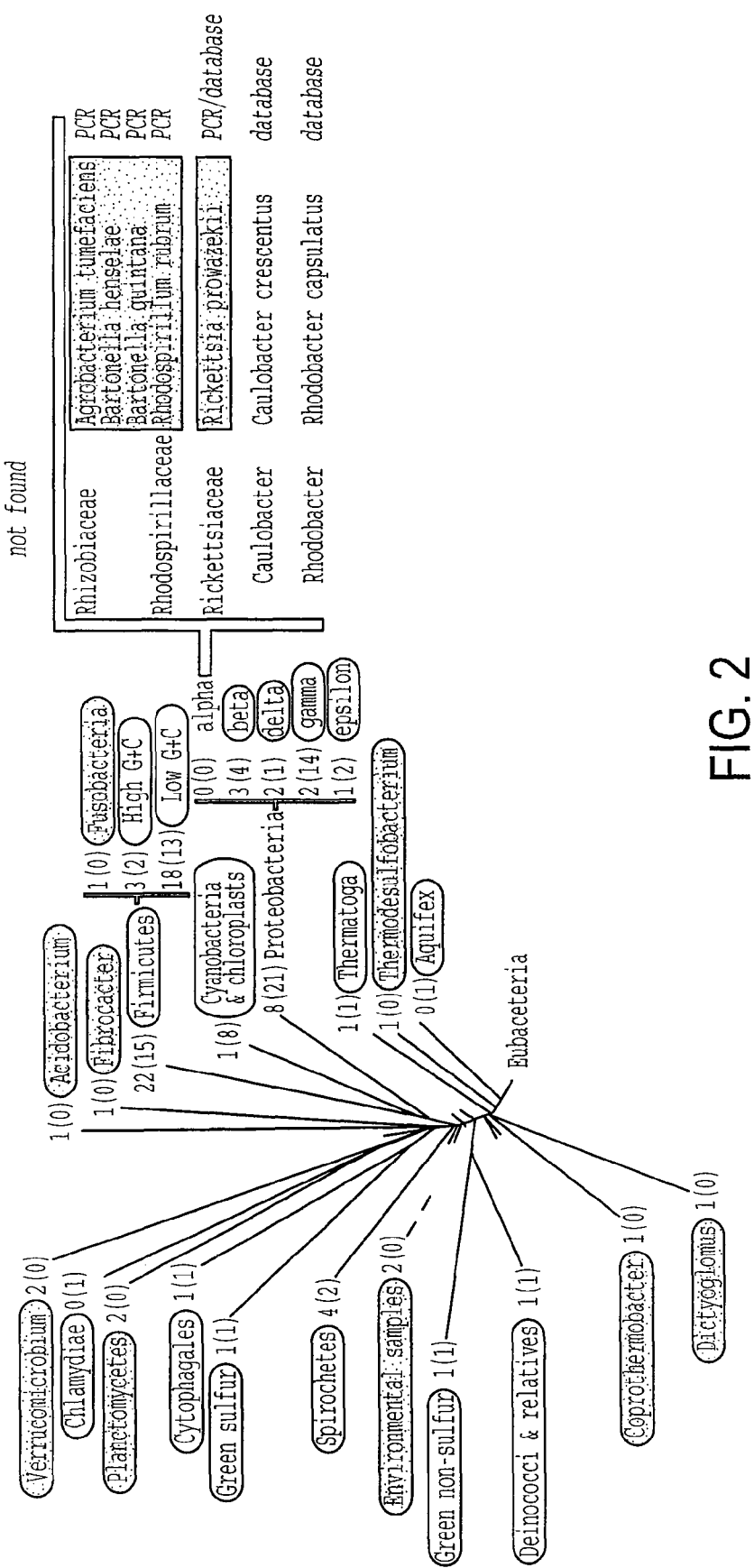
FIG. 2 shows the distribution of tmDNA sequences within eubacterial genomes. The circled phyla or subgroups contain tmDNA sequences and those shaded are new members of this category. The numbers shown close to each phylum are the 51 tmDNA sequences that have are disclosed herein and the numbers in parenthesis are the 53 tmDNA sequences that were previously known (summarized in Williams, 1999; Wower and Zwieb, 1999). The environmental samples are indicated with a dashed line as their connection to the tree is unknown. The 5 alpha-Proteobacteria in which tmDNA sequences were not detected by PCR analysis are labeled "PCR" and the 3 analyzed by Blast search of the complete, or nearly complete, sequenced genomes are labeled "database".
Figure 3A:
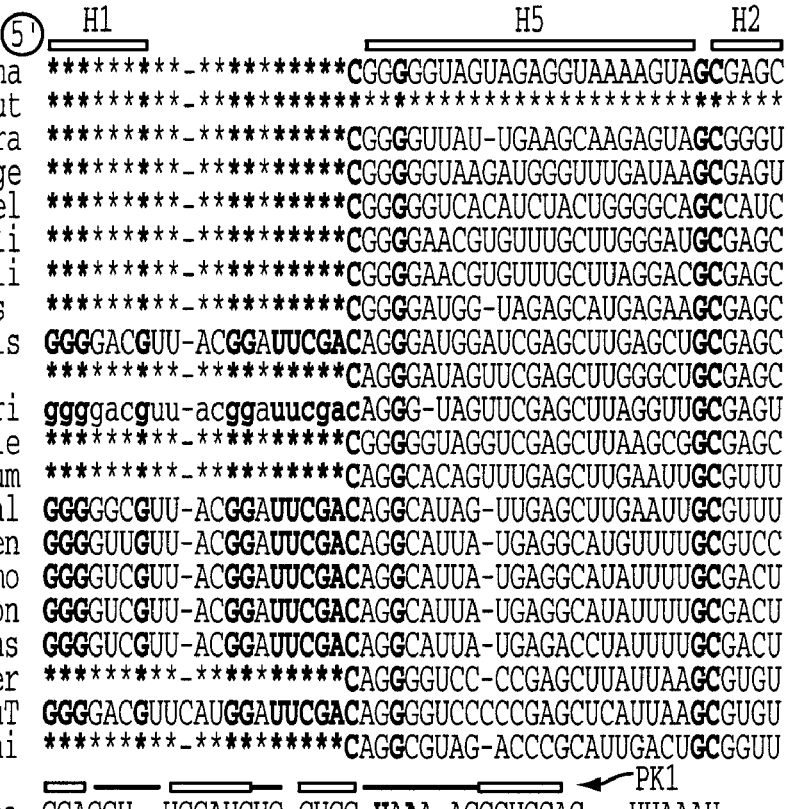
Figure 4A:
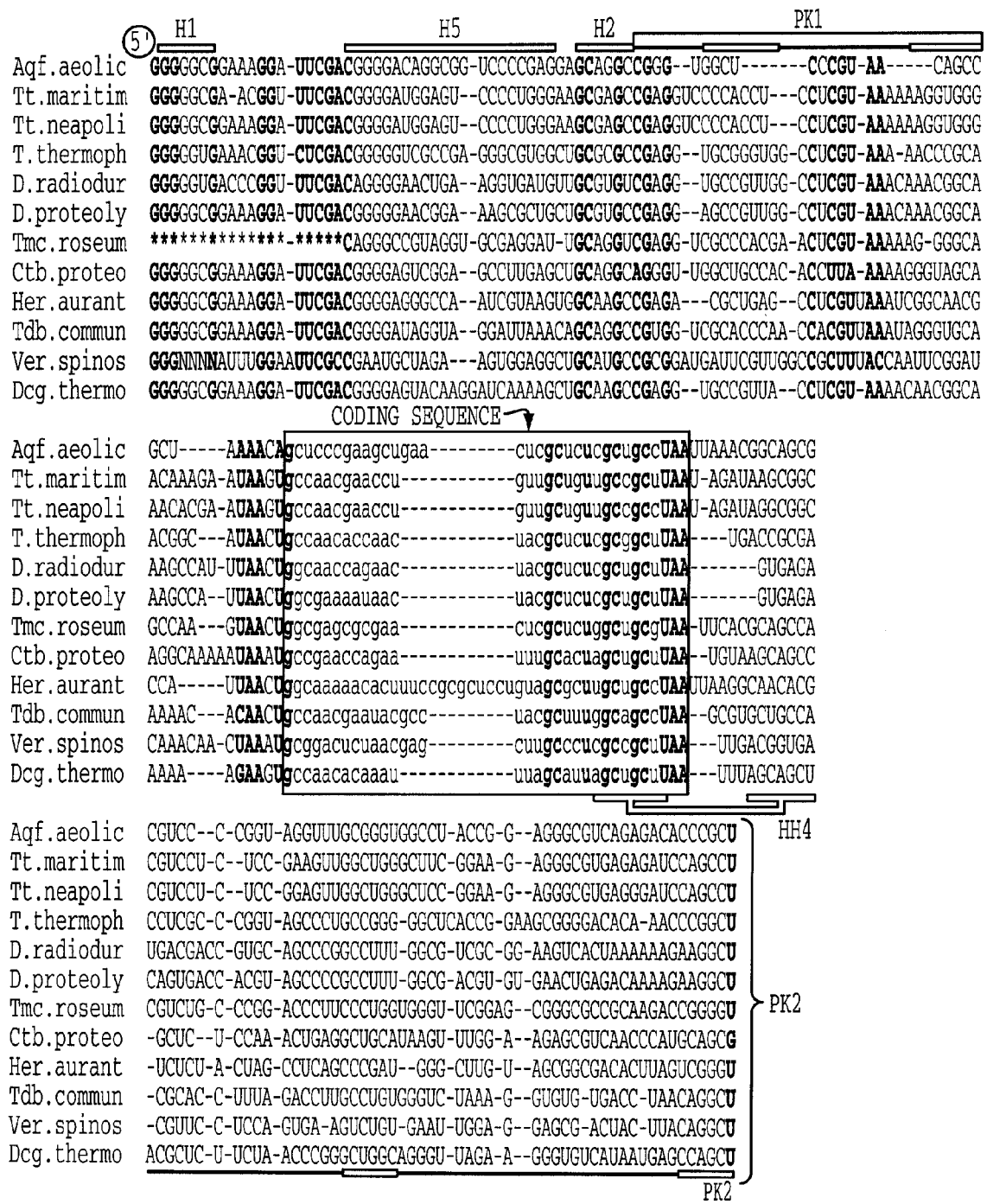
Figure 5A:
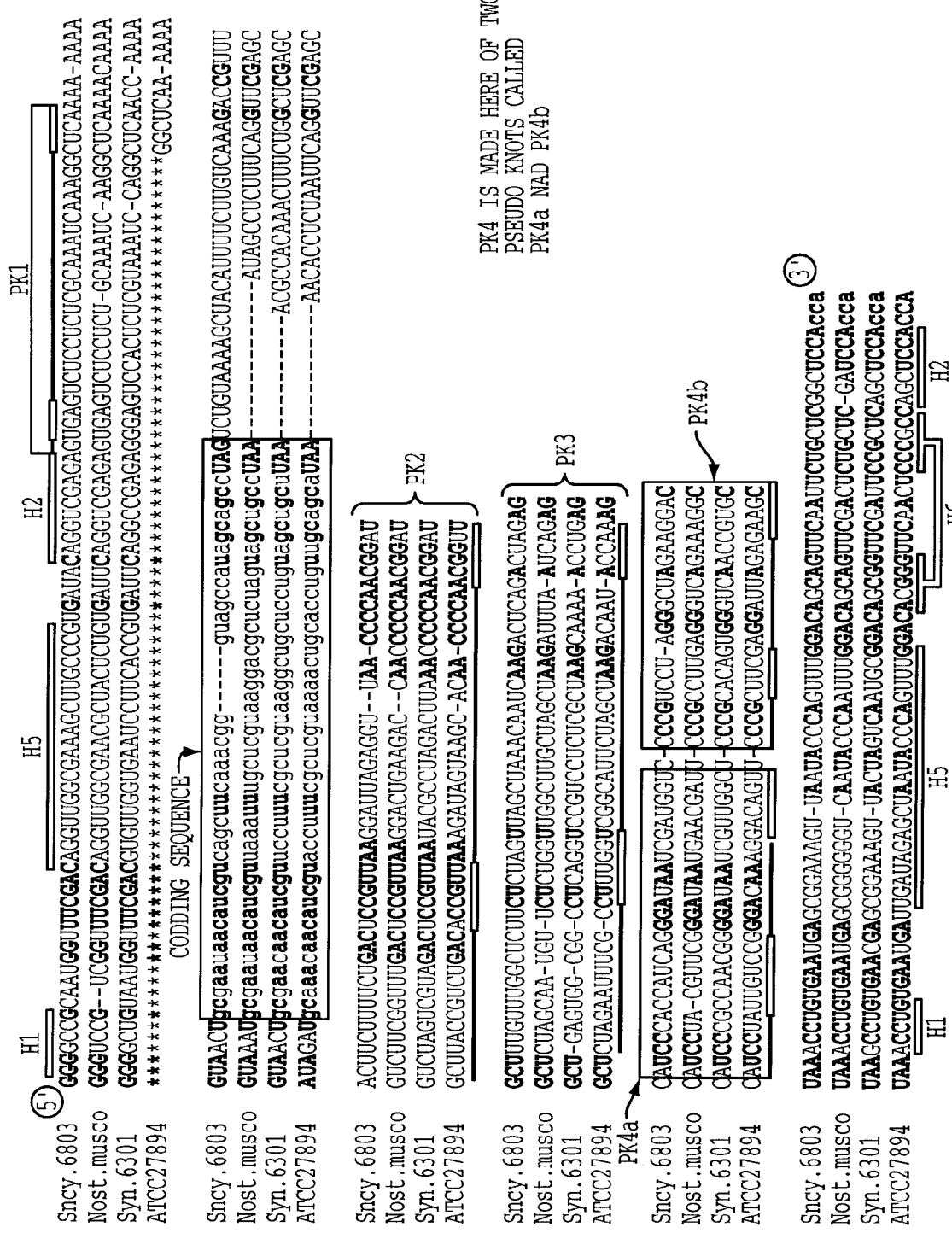
FIGS. 5A and 5B show the sequence alignment, structural domains and structural features for the tmRNA of several species of Cyanobacteries (5A) and chloroplasts (5B). The tmRNA sequences of the Cyanobacteries are set forth in SEQ ID NOs:100-103, and the tmRNA sequences of the chloroplasts are set forth in SEQ ID NOs:104-108.
Figure 5B:
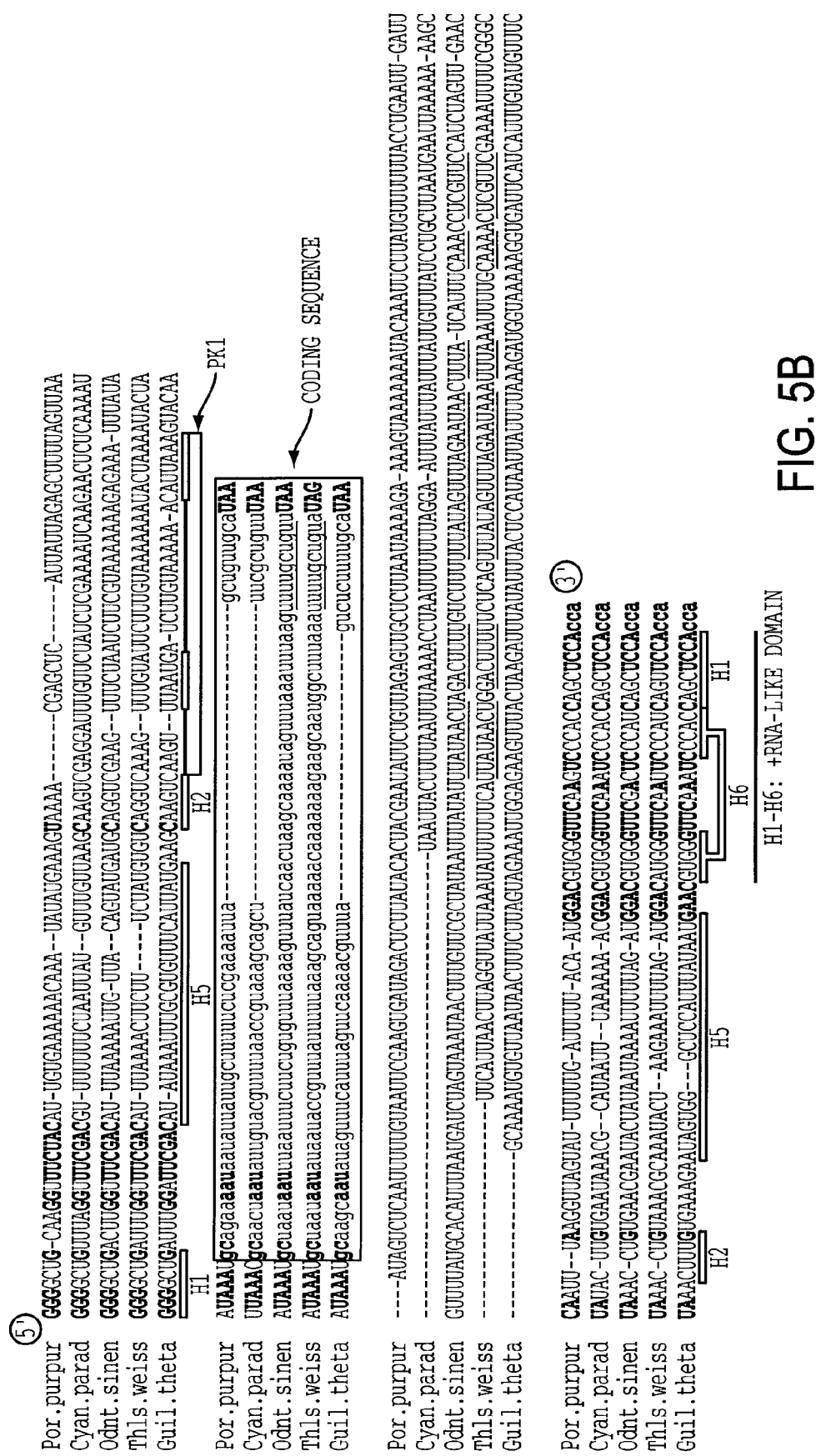
Figure 6A:
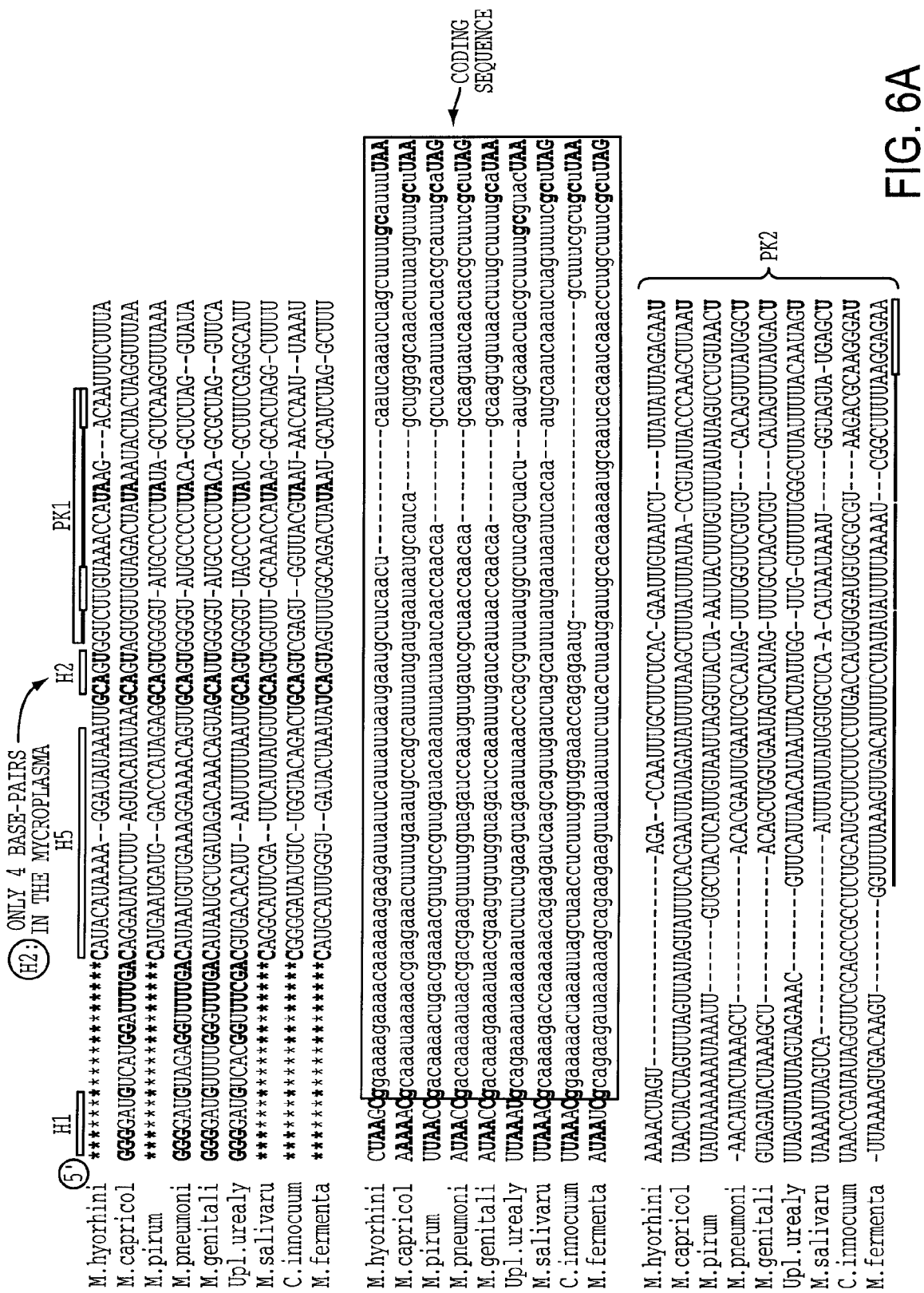
FIGS. 6A and 6B show the sequence alignment, structural domains and structural features for the tmRNA of several species of Mycoplasmes. The tmRNA sequences are set forth in SEQ ID NOs:109-117.
Figure 6B:
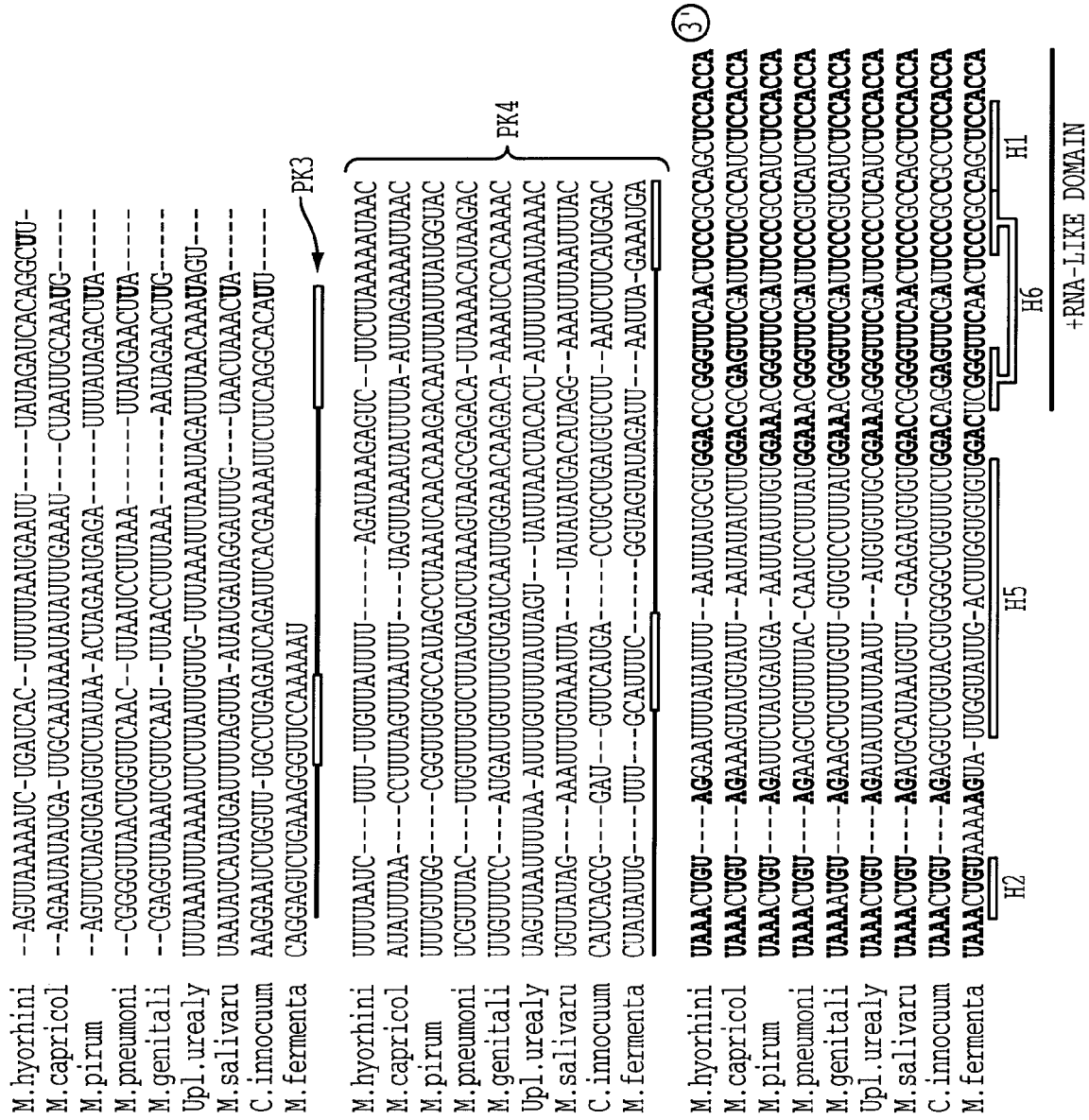
Figures 1, 7A:
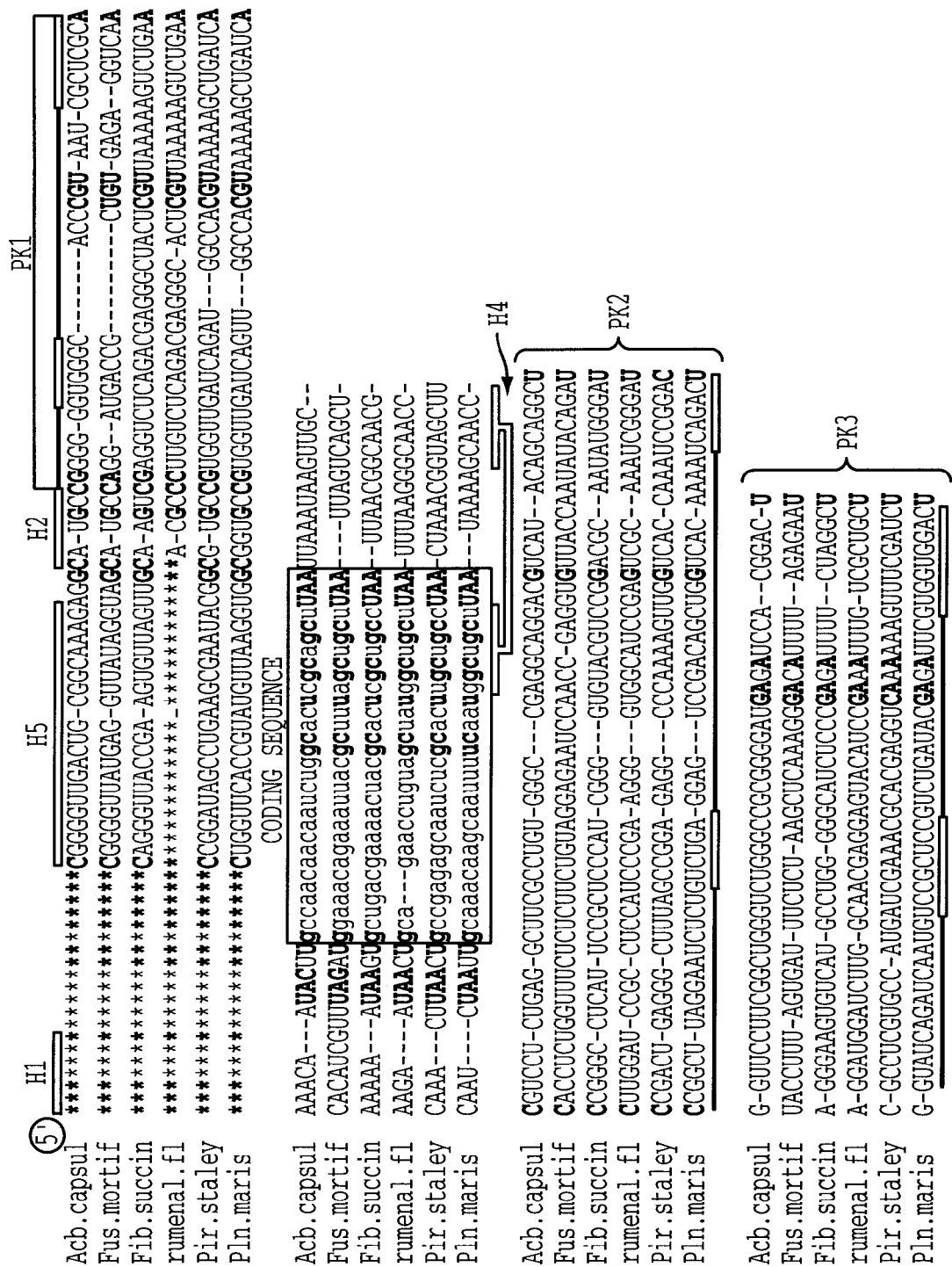
Figure 7C:
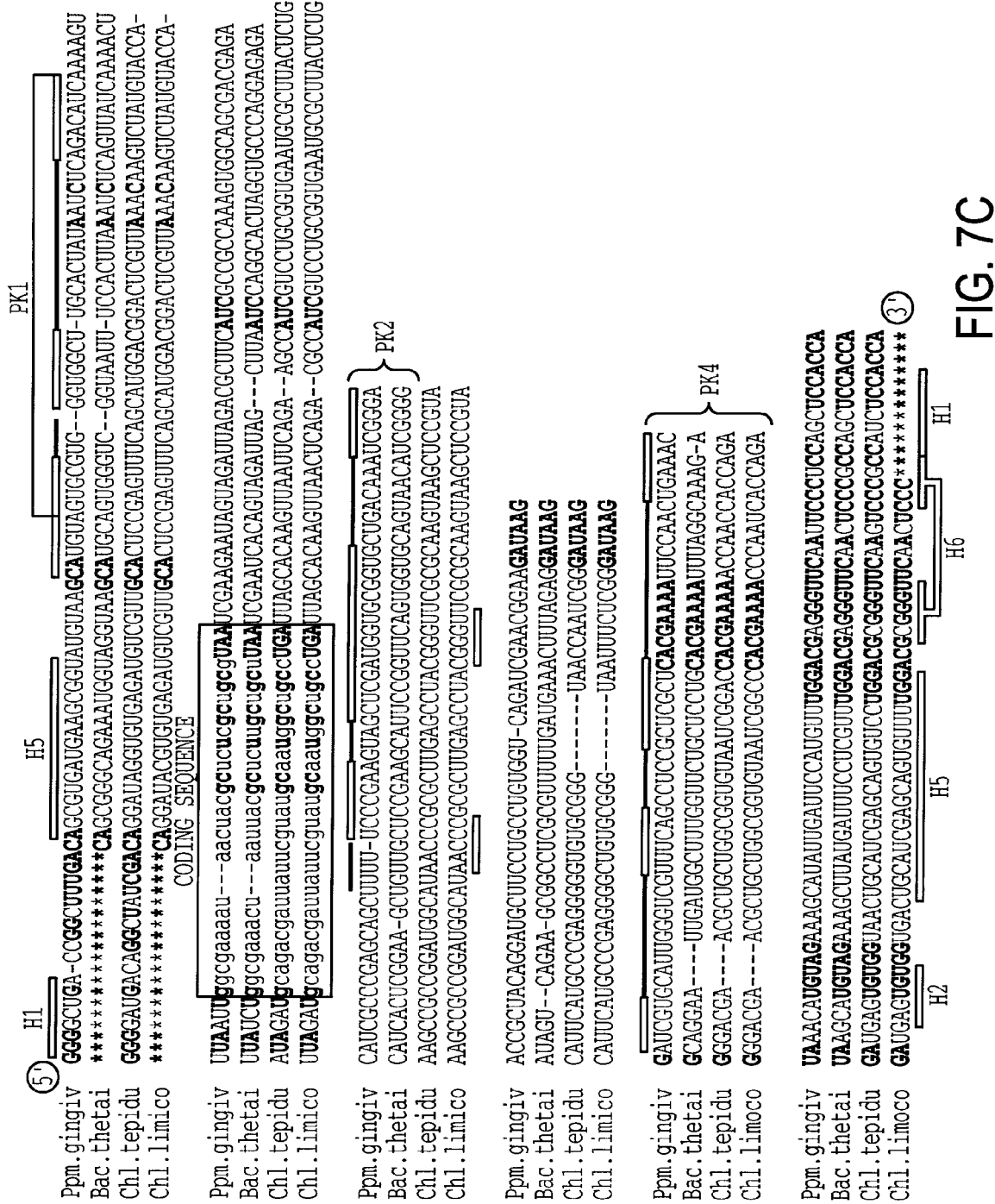
Figure 7D:
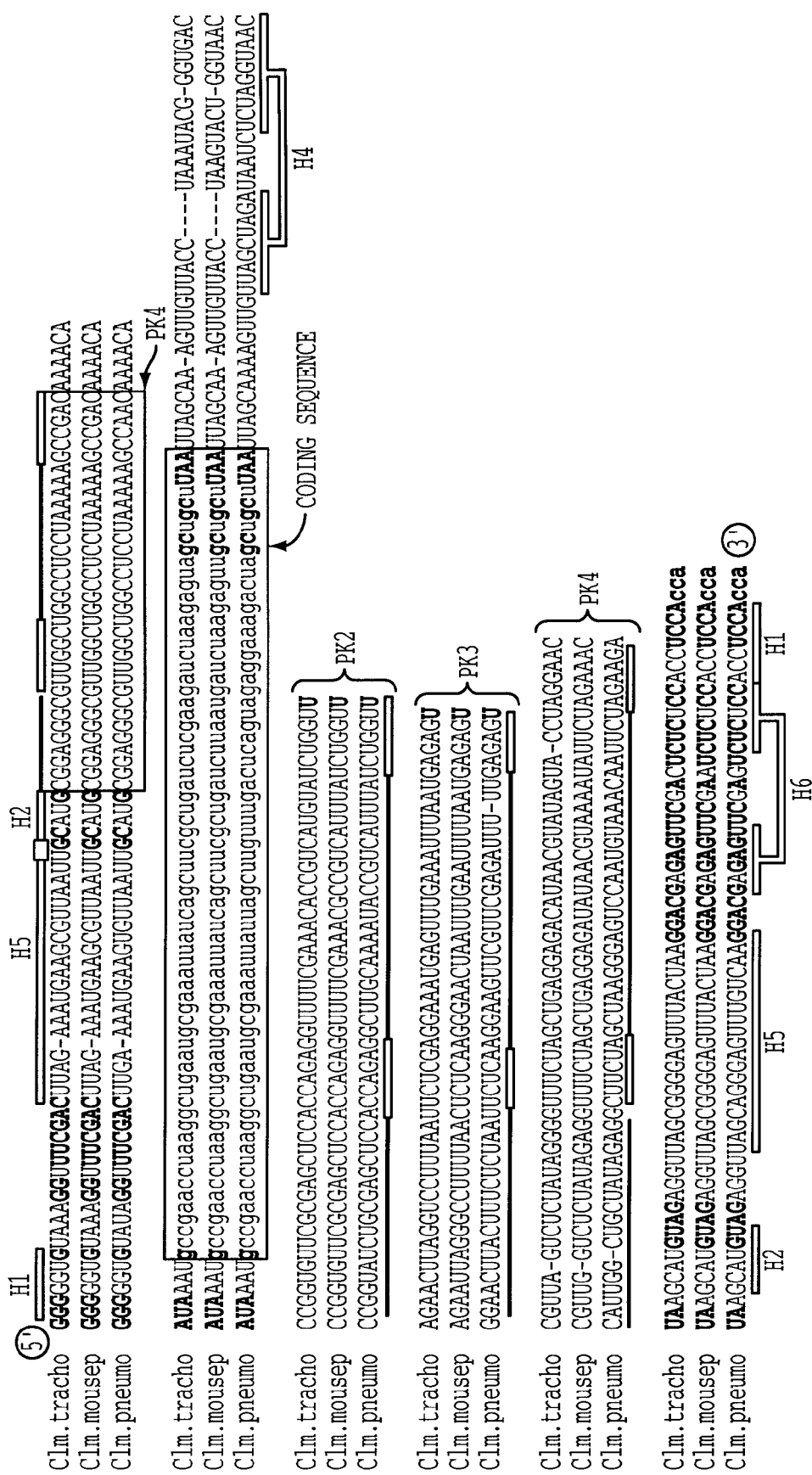
Figure 8A:
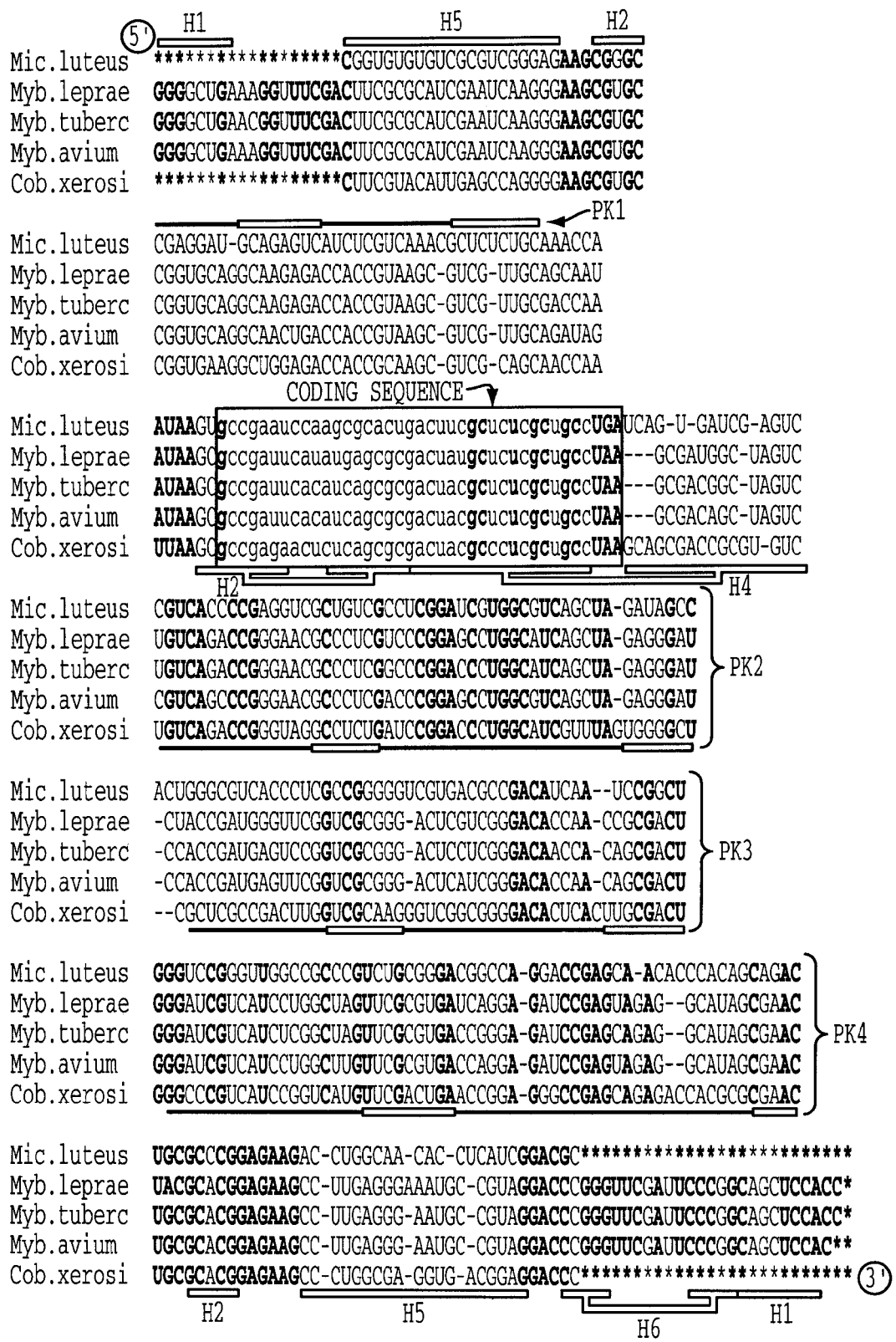
FIGS. 8A and 8B show the sequence alignment, structural domains and structural features for the tmRNA of several species of Actinobacteries (8A) and Spirochaetes (8B). The tmRNA sequences of the Actinobacteries are set forth in SEQ ID NOs:132-136, and the tmRNA sequences of the Spirochaetes are set forth in SEQ ID NOs:137-142.
Figure 8B:
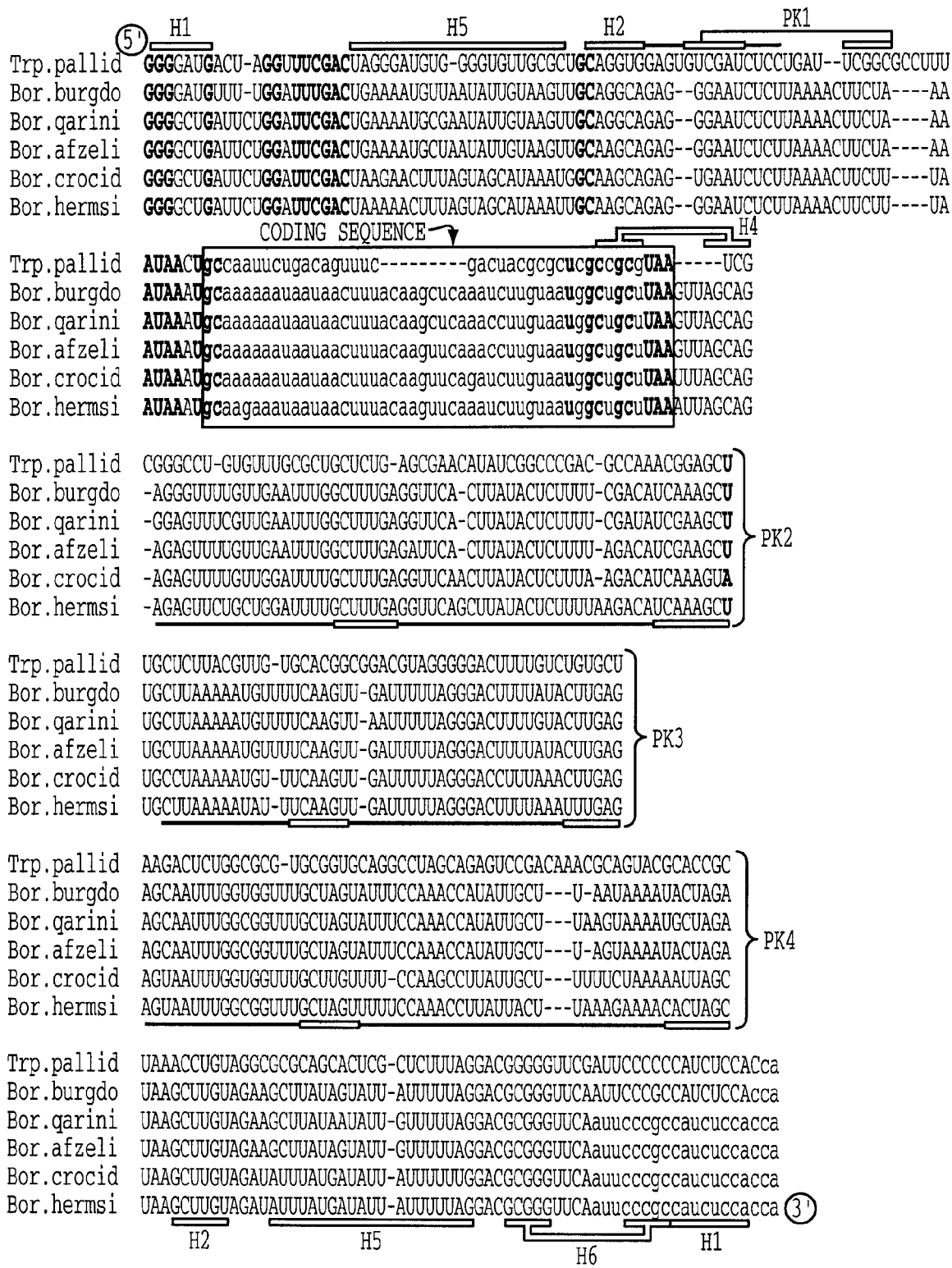
Figure 9A:
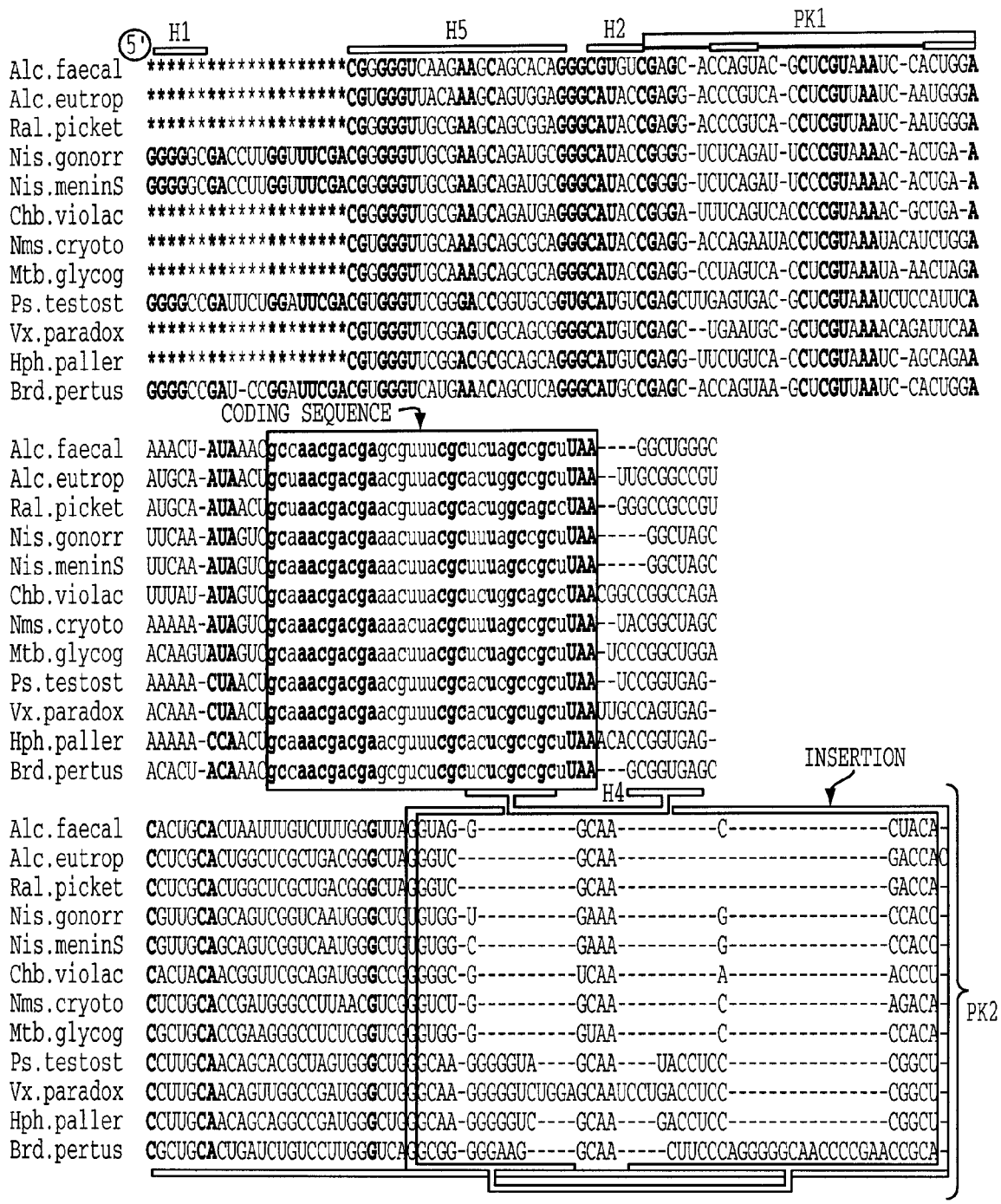
Figure 11B:
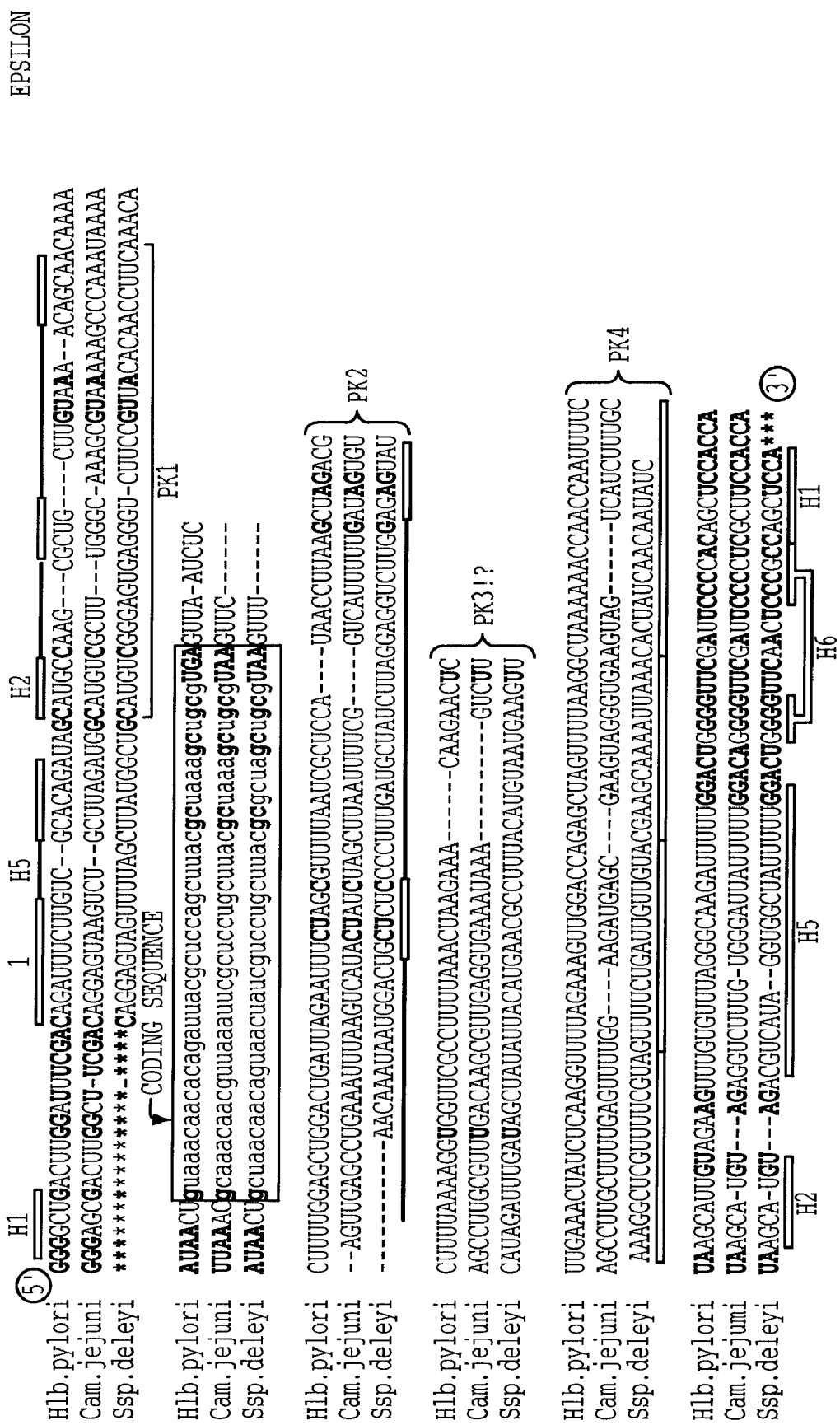

According to these procedures, tmRNA genes from many eubacteria including known human pathogens were amplified. The PCR was facilitated by sequence conservation at both 5' and 3' ends and was performed as described (Williams and Bartel, 1996), with modifications. This study was initiated to collect further sequences from eubacterial tmDNA genes, as well as to test experimentally whether tmDNA genes could be found in all bacterial phyla or subgroups. 51 new tmDNA sequences were determined (FIG. 2), including sequences from members of 8 additional phyla and 1 subgroup (shaded boxes in FIG. 2). The 58 new tmDNA sequences are set forth in Tables 1-58. This brings coverage to a total of 104 sequences in 19 bacterial phyla. Interestingly, tmDNA sequences could be amplified from all species tested apart from those in the alpha-Proteobacteria. Five genomic DNAs from alpha-Proteobacteria (*Agrobacterium tuefaciens*, *Bartonella henselae*, *Bartonella quintana*, *Rhodospirillum rubrum* and *Rickettsia prowazekii*) were extensively checked using various oligonucleotides, annealing temperatures and magnesium concentrations. No specific amplified tmDNA sequences were detected in this subgroup. Moreover, no putative tmDNA sequences could be identified (results herein and Williams, 1999) by Blast searches on the 1 fully sequenced (*Rickettsia prowazekii*) and 2 nearly completed (*Caulobacter crescentus* and *Rhodobacter capsulatus*) alpha-proteobacterial genomes (FIG. 2).

It cannot be ruled out that tmDNA sequences may have largely diverged in the alpha-proteobacterial sub-group compared to other bacterial phyla, and that both PCR methods and Blast searches are missing the relevant sequences. While tmRNA is dispensable in *E. coli* (Ando et al., 1996), it is striking that it has been found in all bacteria tested other than the alpha-Proteobacteria. The alpha-Proteobacteria have undergone reductive evolution. This has been more intensive in one of the two sub-classes than in the other (Gray and Spencer, 1996), but tmRNA sequences have not been found even in the sub-class with the larger genome. Based on sequence comparison, the alpha-Proteobacteria and mitochondria are evolutionary relatives (Yang et al., 1985; Andersson et al., 1998). The drastic downsizing in what has become mitochondrial genomes means that it is not reasonable to draw inferences on the relationship between alpha-Proteobacteria and mitochondria based on their mutual apparent absence of tmRNA. It is nevertheless, of interest, that at least some chloroplasts and cyanelle genomes have tmDNA sequences, and the cyanobacteria, with which they are evolutionary related, also have tmRNA.

TABLE 1 tmDNA Sequence for *Acidobacterium capsulatum* (*Acidobacterium*)

(SEQ ID NO: 9)
GGGGGCGGAAAGGATTCGACGGGGTTGACTGCGGCAAAGAGGCATGCCGG
GGGGTGGGCACCCGTAATCGCTCGCAAAACAATACTTGCCAACAACAATC
TGGCACTCGCAGCTTAATTAAATAAGTTGCCGTCCTCTGAGGCTTCGCCT
GTGGGCCGAGGCAGGACGTCATACAGCAGGCTGGTTCCTTCGGCTGGGTC
TGGGCCGCGGGGATGAGATCCACGGACTAGCATTCTGCGTATCTTGTCGC
TTCTAAGCGCAGAGTGCGAAACCTAAAGGAATGCGACTGAGCATGGAGTC
TCTTTTCTGACACCAATTTCGGACGCGGGTTCGATTCCCGCCGCCTCCAC
CA

TABLE 2 tmDNA Sequence for *Coprothermobacter proteolyticus* (60 degrees)

(SEQ ID NO: 10)
GGGGGCGGAAAGGATTCGACGGGGAGTCGGAGCCTTGAGCTGCAGGCAGG
GTTGGCTGCCACACCTTAAAAAGGGTAGCAAGGCAAAAATAAATGCCGAA
CCAGAATTTGCACTAGCTGCTTAATGTAAGCAGCCGCTCTCCAAACTGAG
GCTGCATAAGTTTGGAAGAGCGTCAACCCATGCAGCGGCTCTTAAGCAGT
GGCACCAGCTGTTTAAGGGTGAAAAGAGTGGTGCTGGGCAGTGCGGTTGG
GCTTCCTGGGCTGCACTGTCGAGACTTCACAGGAGGGCTAAGCCTGTAGA
CGCGAAAGGTGGCGGCTCGTCGGACGCGGGTTCGATTCCCGCCGCCTCCA
CCA

TABLE 3 tmDNA Sequence for *Bacteroides thetaiotaomicron* (*bacteroides/flavobacterium*)

(SEQ ID NO: 11)
GGGGCTGATTCTGGATTCGACAGCGGGCAGAAATGGTAGGTAAGCATGCA
GTGGGTCGGTAATTTCCACTTAAATCTCAGTTATCAAAACTTTATCTGGC
GAAACTAATTACGCTCTTGCTGCTTAATCGAATCACAGTAGATTAGCTTA
ATCCAGGCACTAGGTGCCAGGACGAGACATCACTCGGAAGCTGTTGCTCC
GAAGCATTCCGGTTCAGTGGTGCAGTAACATCGGGGATAGTCAGAAGCGG
CCTCGCGTTTTTGATGAAACTTTAGAGGATAAGGCAGGAATTGATGGCTT
TGGTTCTGCTCCTGCACGAAAATTTAGGCAAAGATAAGCATGTAGAAAGC
TTATGATTTCCTCGTTTGGACGAGGGTTCAACTCCCGCCAGCTCCACCA

TABLE 4 tmDNA Sequence for *Dictyoglomus thermophilum* (70 degrees)

(SEQ ID NO: 12)
GGGGCTGATTCTGGATTCGACAGGGAGTACAAGGATCAAAAGCTGCAAGC
CGAGGTGCCGTTACCTCGTAAAACAACGGCAAAAAAGAAGTGCCAACACA

TABLE 4-continued tmDNA Sequence for *Dictyoglomus thermophilum* (70 degrees)

AATTTAGCATTAGCTGCTTAATTTAGCAGCTACGCTCTTCTAACCCGGGC
TGGCAGGGTTAGAAGGGTGTCATAATGAGCCAGCTGCCCCTTCCGACTCC
CCTAAGGAAGGGAAAGATGTAGGGGATAGGTGCTTACAGAATCCTGCGGG
AGGGAGTCTGTAAGTGCCGAAAAGTTAAAACTCCCGCTAAGCTTGTAGAG
GCTTTTGATTCTTGCTCTCTGGACGCGGGTTCAACTCCCGCCAGCTCCAC
CA

TABLE 5 tmDNA Sequence for Environmental Sample from Rumenal Fluid (SEQ ID NO: 13)
ACGCCCTTGTCTCAGACGAGGGCACTCGTTAAAAAGTCTGAAAAGAATAA
CTGCAGAACCTGTAGCTATGGCTGCTTAATTTAAGGGCAACCCTTGGATC
CGCCTCCATCCCGAAGGGGTGGCATCCGAGTCGCAAATCGGGATAGGATG
GATCTTGGCAACGAGGAGTACATCCGAAATTTGTCGCTGCTGGCTGAAGC
ATCGCCGTTCCTCTTTGGGCGTGGCAAGGCAAGATTAAATTCAGAGGATA
AGCGTGTAGTAGCGAGTGAGTAGGTGTTTTTGGACGCGGGTTCAAGTCCC
GCCATCTCCACCA

TABLE 6 tmDNA Sequence for Environmental Sample from Sludge (SEQ ID NO: 14)
GGGGATGTCATGGTTTTGACAGGGAACCAGGAGGTGTGAGATGCATGCCG
GAGACGCTGTCCGCTCCGTTATCAAGCAGCAAACAAAACTAATTGCAAAC
AACAATTACTCCTTAGCAGCGTAAGCAGCTAACGTTCAACCTCTCCGGAC
CGCCGGGAGGGGATTTGGGCGTCGAAACAGCGCGGACGCTCCGGATAGGA
CGCCCATAATATCCGGCTAAGACCATGGGTCTGGCTCTCGCGGGTCTGAT
TGTCTTCCACCGCGCGGGCCGCGATCAAAGACAACTAAGCATGTAGGTTC
TTGCATGGCCTGTTCTTTGGACGCGGGTTCGATTCCCGCCATCTCCACCA

TABLE 7 tmDNA Sequence for *Fibrobacter succinogenes* (*Fibrobacter*)

(SEQ ID NO: 15)
GGGGCTGATTCTGGATTCGACAGGGTTACCGAAGTGTTAGTTGCAAGTCG
AGGTCTCAGACGAGGGCTACTCGTTAAAAAGTCTGAAAAAAAATAAGTGC
TGACGAAAACTACGCACTCGCTGCCTAATTAACGGCAACGCCGGGCCTCA
TTCCGCTCCCATCGGGGTGTACGTCCGGACGCAATATGGGATAGGGAAGT
GTCATGCCTGGGGGCATCTCCCGAGATTTTCTAGGCTGGTCAAACTCCGC
GCCGACCTTCTTGGGCGTGGATAAGACGAGATCTTAAATTCGAAGGGAAC
ACTTGTAGGAACGTACATGGACGTGATTTTGGACAGGGGTTCAACTCCCG
CCAGCTCCA

TABLE 8 tmDNA Sequence for *Fusobacterium mortiferum*

(SEQ ID NO: 16)
GGGGCTGATTCTGGATTCGACGGGGTTATGAGGTTATAGGTAGCATGCCA
GGATGACCGCTGTGAGAGGTCAACACATCGTTTAGATGGAAACAGAAATT
ACGCTTTAGCTGCTTAATTAGTCAGCTCACCTCTGGTTTCTCTCTTCTGT
AGGAGAATCCAACCGAGGTGTTACCAATATACAGATTACCTTTAGTGATT
TCTCTAAGCTCAAAGGGACATTTTAGAGAATAGCTTCAGTTAGCCCTGTC
TGCGGGAGTGATTGTTGCGAAATAAAATAGTAGACTAAGCATTGTAGAAG
CCTATGGCGCTGGTAGTTTCGGACACGGGTTCAACTCCCGCCAGCTCCAA

TABLE 9 tmDNA Sequence for *Corynebacterium xerosis* (gram +, high G-C content)

(SEQ ID NO: 17)
GGGGCTGATTCTGGATTCGACTTCGTACATTGAGCCAGGGGAAGCGTGCC
GGTGAAGGCTGGAGACCACCGCAAGCGTCGCAGCAACCAATTAAGCGCCG
AGAACTCTCAGCGCGACTACGCCCTCGCTGCCTAAGCAGCGACCGCGTGT
CTGTCAGACCGGGTAGGCCTCTGATCCGGACCCTGGCATCGTTTAGTGGG
GCTCGCTCGCCGACTTGGTCGCAAGGGTCGGCGGGGACACTCACTTGCGA
CTGGGCCCGTCATCCGGTCATGTTCGACTGAACCGGAGGGCCGAGCAGAG
ACCACGCGCGAACTGCGCACGGAGAAGCCCTGGCGAGGTGACGGAGGACC
CGGGGTTCAACTCCCGCCAGCTCCACCA

TABLE 10 tmDNA Sequence for *Micrococcus luteus* (parfait)

(SEQ ID NO: 18)
GGGGCTATTCTGGATTCGACGGTGTGTGTCGCGTCGGGAGAAGCGGGCCG
AGGATGCAGAGTCATCTCGTCAAACGCTCTCTGCAAACCAATAAGTGCCG
AATCCAAGCGCACTGACTTCGCTCTCGCTGCCTGATCAGTGATCGAGTCC
GTCACCCCGAGGTCGCTGTCGCCTCGGATCGTGGCGTCAGCTAGATAGCC
ACTGGGCGTCACCCTCGCCGGGGGTCGTGACGCCGACATCAATCCGGCTG
GGTCCGGGTTGGCCGCCCGTCTGCGGGACGGCCAGGACCGAGCAACACCC
ACAGCAGACTGCGCCCGGAGAAGACCTGGCAACACCTCATCGGACGCGGG
TTCAACTCCCGCANTCCCACCA

TABLE 11 tmDNA Sequence for *Mycobacterium smegmatis*

(SEQ ID NO: 19)
TCATCTCGGCTTGTTCGCGTGACCGGGAGATCCGAGTAGAGACATAGCGA
ACTGCGCACGGAGAGGGGCTGATTCCTGGATTCGACTTCGAGCATCGAAT
CCAGGGAAGCGTGCCGGTGCAGGCAAGAGACCACCGTAAGCGTCGTTGCA
ACCAATTAAGCGCCGATTCCAATCAGCGCGACTACGCCCTCGCTGCCTAA
GCGACGGCTGGTCTGTCAGACCGGGAGTGCCCTCGGCCCGGATCCTGGCA
TCAGCTAGAGGGACCCACCCACGGGTTCGGTCGCGGGACCTGTGGGGACA
TCAAACGACTGGGATCGAGCCTCGAGGACATGCCGTAGGACCCGGGT
TCAACTCCCGCCAGCTCCACCA

TABLE 12 tmDNA Sequence for *Bacillus badius*

(SEQ ID NO: 20)
GGGGGTGATTCTGGATTCGACAGGGATAGTTCGAGCTTGGGCTGCGAGCC
GGAGGGCCGTCTTCGTACCAACGCAAACGCCTAAATATAACTGGCAAAAA
AGATTTAGCTTTAGCTGCCTAATATAGGTTCAGCTGCTCCTCCCGCTATC
GTCCATGTAGTCGGGTAAGGGGTCCAAACTTAGTGGACTACGCCGGAGTT
CTCCGCCTGGGGACAAAGGAAGAGATCAATCAGGCTAGCTGCCCGGACGC
CCGTCGATAGGCAAAAGGAACAGTGAACCCCAAATATATCGACTACGCTC
GTAGACGTTCAAGTGGCGTTATCTTTGGACGTGGGTTCAACTCCCGCCAG
CTCCA

TABLE 13 tmDNA Sequence for *Bacillus brevis*

(SEQ ID NO: 21)
GGGGGCGGAAAGGATTCGACGGGGATGGTAGAGCATGAGAAGCGAGCCGG
GGGGTTGCGGACCTCGTCACCAACGCAAACGCCATTAACTGGCAACAAAC
AACTTTCTCTCGCTGCTTAATAACCAGTGAGGCTCTCCCACTGCATCGGC
CCGTGTGCCGTGGATAGGGCTCAACTTTAACGGGCTACGCCGGAGGCTTC
CGCCTGGAGCCAAAGGAAGAAGACCAATCAGGCTAGGTGCCAGGTCAGCG
CGTCACTCGCGAATCTGTCACCGAAACTCTAAACGAGTGACTGCGCTCG
GAGATGCTCATGTATCGCTGTTTTCGGACGGGGGTTCGATTCCCGCCGCC
TCACCCA

TABLE 14 tmDNA Sequence for *Bacillus thermoleovorans* (50-60 degres)

(SEQ ID NO: 22)
GGGGGCGGAAAGGATTCGACGGGGGTAGGTCGAGCTTAAGCGGCGAGCCG
AGGGGGACGTCCTCGTAAAAACGTCACCTAAAGATAACTGGCAAACAAAA
CTACGCTTTAGCTGCCTAATTGCTGCAGCTAGCTCCTCCCGCCATCGCCC
GCGTGGCGTTCGAGGGGCTCATATGGAGCGGGCTACGCCCAAATCCGCCG
CCTGAGGATGAGGGAAGAGACGAATCAGGCTAGCCGCCGGGAGGCCTGTC
GGTAGGCGGAACGGACGGCGAAGCGAAATATACCGACTACGCTCGTAGAT
GCTTAAGTGGCGATGCCTCTGGACGTGGGTTCGATTCCCGCCGCCTCCCC
ACCA

TABLE 15 tmDNA Sequence for *Clostridium innocuum*

(SEQ ID NO: 23)
GGGGGCGGAAAGGATTCGACGGGGATATGTCTGGTACAGACTGCAGTCGA
GTGGTTACGTAATAACCAATTAAATTTAAACGGAAAAACTAAATTAGCTA
ACCTCTTTGGTGGAAACCAGAGAATGGCTTTCGCTGCTTAATAACCGATA
TAGGTTCGCAGCCGCCTCTGCATGCTTCTTCCTTGACCATGTGGATGTGC
GCGTAAGACGCAAGGGATAAGGAATCTGGTTTGCCTGAGATCAGATTCAC
GAAAATTCTTCAGGCACATTCATCAGCGGATGTTCATGACCTGCTGATGT
CTTAATCTTCATGGACTAAACTGTAGAGGTCTGTACGTGGGGCTGTTTCT
GGACAGGAGTTCGATTCCCGCCGCCTCACCACCA

TABLE 16 tmDNA Sequence for *Clostridium lentocellum*

(SEQ ID NO: 24)
GGGGGCGGAAAGGATTCGACGGGGGTCACATCTACTGGGGCAGCCATCCG
TAGAACGCCGGAGTCTACGTTAAAAGCTGGCACTTAAAGTAAACGCTGAA
GATAATTTAGCAATCGCTGCCTAATTAAGGCGCAGTCCTCCTAGGTCTTC
CGCAGCCTAGATCAGGGCTTCGACTCGCGGATCCTTCACCTGGCAAAGCT
TTGAGCCAACGTGAACACTATGAAGCTACTAAAATCTAGAGCCTGTCTTT
GGGCGCTAGATGGAGGGAATGTCAAAACAAAGAATATGATGGTAGAGACC
ACGCTATATGGGCTTTCGGACAGGGGTTCGATTCCCGCCGCCTTCACCA

TABLE 17 tmDNA Sequence for *Clostridium perfringens*

(SEQ ID NO: 25)
GGGGCTGATTCTGGATTCGACGGGGGTAAGATGGGTTTGATAAGCGAGTC
GAGGGAAGCATGGTGCCTCGATAATAAAGTATGCATTAAAGATAAACGCA
GAAGATAATTTTGCATTAGCAGCTTAATTTAGCGCTGCTCATCCTTCCTC
AATTGCCCACGGTTGAGAGTAAGGGTGTCATTTAAAAGTGGGGAACCGAG
CCTAGCAAAGCTTTGAGCTAGGAACGGAATTTATGAAGCTTACCAAAGAG
GAAGTTTGTCTGTGGACGTTCTCTGAGGGAATTTTAAAACACAAGACTAC
ACTCGTAGAAAGTCTTACTGGTCTGCTTTCGGACACGGGTTCAACTCCCG
CCACTCCA

TABLE 18 tmDNA Sequence for *Clostridium stercorarium*

(SEQ ID NO: 26)
GGGGGCGGAAAGGATTCGACGGGGTTATTGAAGCAAGAGTAGCGGGTAGA
GGATTCTCGTTGGCCTCTTTAAAAAACGAGAGCTAAAAATAAACGCAAAC
AACGATAACTACGCTTTAGCTGCTGCGTAAGTAACACGCAGCCCGTCGGC
CCCGGGGTTCCTGCGCCTCGGGATACCGGCGTCATCAAGGCAGGGAACCA
GCCGGATCAGGCTTCAGGTCCGTGGGATTTAATGAAGCTACCGACTTAT
AAAGCCTGTCTCTGGGCGTTATAAGAAGGGAATGTCAAAACAGAGACTGC
ACCCGGAGAAGCTCTTGTGGATATGGTTCCGGACACGAGTTCGATTCCCG
CCGCCTCCACCA

TABLE 19 tmDNA Sequence for *Enterococcus faecium* (sp.)

(SEQ ID NO: 27)
GGGGCTGATTATGGATTCGACAGGATNGTTGAGCTTGAATTGCGTTTCGT
AGGTTACGGCTACGTTAAAACGTTACAGTTAAATATAACTGCTAAAAACG
AAAACAATTCTTTCGCTTTAGCTGCCTAAAAACCAGCTAGCGAAGATCCT
CCCGGCATCGCCCATGTGCTCGGGTCAGGGTCCTAATCGAAGTGGGATAC
GCTAAATTTTTCCGTCTGTAAAATTTAGAGGAGCTTACCAGACTAGCAAT
ACAAGAATGCCTGTCACTCGGCACGCTGTAAAGCGAACCTTTAAATGAGT
GTCTATGAACGTAGAGATTTAAGTGGGAATATGTTTTGGACGCGGGTTCA
ACTCCCGCCAGCTCCACCA

TABLE 20 tmDNA Sequence for *Heliobacillus mobilis* (photosyn/gram +)

(SEQ ID NO: 28)
GGGGCTGATTCTGGATTCGACGGGGAACGTGTTTGCTTGGGATGCGAGCC
GGGTTGCCGCCAGGACCGTAAAAAGGGCGGAAGGCTTTAATTGCCGAAGA
TAACTACGCTTTAGCTGCTTAATTGCAGTCTAACCTCTTCTCCTCTGTGC
TCTCGGTGAGGATGTAAGGGGTCATTTAAGAGAGCTGGCTCGACCAATT
CTCGGAGGTCCAAGCGAGATTTATCGAGATAGCCTGACCAACGCTCTGTC
TGCCGTGCGGAAGGAAGGCGAAATCTAAAACGACAGACTACGCTCGTAGT
GTCCTTTGTGGGCATTTCTTCGGACGCGGGTTCAACTCCCGCCAGCTCCA
CCA

TABLE 21 tmDNA Sequence for *Heliospirillum gestii*

(SEQ ID NO: 29)
GGGGCTGATTCTGGATTCGACGGGGAACGTGTTTGCTTAGGACGCGAGCC
GGGTTGCCGCCAGGACCGTAAAAAGGGCGGAAGGCTTTAATTGCCGAAGA
TAACTACGCTTTAGCTGCTTAATTGCAGTCTAACCTCTTCTCCTCTGTGC
TCTCGGTGAGGATGTAAGGGGTCATTTAAGAGAGCTGGCTCGAACCAATT
CTCGGAGGTTCGGGTAAGACTTATCGAGATAGCCTGACCAACGCTCTGTC
TGCCGTGCGGAAGGATGGCGAAATCTAAAACGACAGAATACGCTCGTAGT
GTCCTTTGTGGGCATTTCTTCGGACGCGGGTTCAACTCCCGCCAGCTCCA
CCA

TABLE 22 tmDNA Sequence for *Lactobacillus acidophilus*

(SEQ ID NO: 30)
GGGGCTGATTCTGGATTCGACAGGCGTAGACCCGCATTGACTGCGGTTCG
TAGGTTACGTCTACGTAAAAACGTTACAGTTAAATATAACTGCAAATAAC
AAAAATTCTTACGCATTAGCTGCTTAATTTAGCGCATGCGTTGCTCTTTG
TCGGTTTACTCGTGGCTGACACTGAGTATCAACTTAGCGAGTTACGTTTA
ACTACCTCACCTGAATAGTTGAAAAGAGTCTTAGCAGGTTAGCTAGTCCA
TACTAGCCCTGTTATATGCGTTTTGGACTAGTGAAGTTCAAGTAATATA
ACTATGATCGTAGAGGTCAGTGACGAGATGCGTTTGGACAGCGGGTTCAA
CTCCCGCCAGCTCCACCA

TABLE 23 tmDNA Sequence for *Staphylococcus epidermidis*

(SEQ ID NO: 31)
GGGGCTGATTCTGCATTCGACAGGGGTCCCCGAGCTTATTAAGCGTGTGG
AGGGTTGGCTCCGTCATCAACACATTTCGGTTAAATATAACTGACAAATC
AAACAATAATTTCGCAGTAGCTGCGTAATAGCCACTGCATCGCCTAACAG
CATCTCCTACGTGCTGTTAACGCGATTCAACCCTAGTAGGATATGCTAAA
CACTGCCGCTTGAAGTCTGTTTAGATGAAATATAATCAAGCTAGTATCAT
GTTGGTTGTTTATTGCTTAGCATGATGCGAAAATTATCAATAAACTACAC
ACGTAGAAAGATTTGTATCAGGACCTCTGGACGCGGGTTCAACTCCCGCC
AGCTCCACCA

TABLE 24 tmDNA Sequence for *Streptococcus faecium*

(SEQ ID NO: 32)
GGGGCTGATTCTGGATTCGACAGGCACAGTTTGAGCTTGAATTGCGTTTC
GTAGGTTACGTCTACGTTAAAACGTTACAGTTAAATATAACTGCTAAAAA
CGAAAACAACTCTTACGCTTTAGCTGCCTAAAAACAGTTAGCGTAGATCC
TCTCGGCATCGCCCATGTGCTCGAGTAAGGGTCTCAAATTTAGTGGGATA
CGTGACAACTTTCCGTCTGTAAGTTGTTAAAGAGATCATCAGACTAGCGA
TACAGAATGCCTGTCACTCGGCAAGCTGTAAAGCGAAACCACAAATGAGT
TGACTATGAACGTAGATTTTTAAGTGGCGATGTGTTTGGACGCGGGTTCA
ACTCCCGCCGTTCCACCA

TABLE 25 tmDNA Sequence for *Thermoanaerobacterium saccharolyticum* (*Bacillus/clostridium*)

(SEQ ID NO: 33)
GGGGTAGTAGAGGTAAAAGTAGCGAGCCGAGGTTCCATCTGCTCGTAAAA
CGGTGGACTTAAATATAAACGCAAACGATAATTTAGCTTACGCTGCTTAA
TTACAAGCAGCCGTTCAACCTTTGATTCCCACATCAAAGGATTGGGCGTC
GATTTAGTGGGGAACTGATTTATCAAAGCTTTGAGATAAATCGGATTTTA
TGAAGCTACCAAAGCAGTTATCCTGTCACTGGGAGAACTGCAGAGGGAAT
GTCAAAACAGTGACTGCGCTCGGAGAAGCTTTTACTGTGACACCTTCGGA
CCGGGGTTCAACTCCCGCCAGCTCCACCA

TABLE 26 tmDNA Sequence for *Mycoplasma fermentans*

(SEQ ID NO: 34)
GGGGCTGATTCTGGATTCGACATGCATTGGGTGATACTAATATCAGTAGT
TTGGCAGACTATAATGCATCTAGGCTTTATAATCGCAGAAGATAAAAAAG
CAGAAGAAGTTAATATTTCTTCACTTATGATTGCACAAAAAATGCAATCA
CAATCAAACCTTGCTTTCGCTTAGTAAAAGTGACAAGTGGTTTTAAAGT
TGACATTTTCCTATATATTTTAAAATCGGCTTTTAAGGAGAACAGGAGTC
TGAAAGGGTTCCAAAAATCTATATTGTTTGCATTTCGGTAGTATAGATTA
ATTAGAAATGATAAACTGTAAAAAGTATTGGTATTGACTTGGTGTGTGGA
CTCGGGTTCAACTCCCGCCAGCTCCACCA

TABLE 27 tmDNA Sequence for *Mycoplasma hyorhinis*

(SEQ ID NO: 35)
GGGGCTGATTCTGGATTCGACATACATAAAAGGATATAAATTGCAGTGGT
CTTGTAAACCATAAGACAATTTCTTTACTAAGCGGAAAAGAAAACAAAAA
AGAAGATTATTCATTATTAATGAATGCTTCAACTCAATCAAATCTAGCTT
TTGCATTTTAAAAAACTAGTAGACCAATTTGCTTCTCACGAATTGTAATC
TTTATATTAGAGAATAGTTAAAAATCTGATCACTTTTTAATGAATTTATA
GATCACAGGCTTTTTAATCTTTTTGTTATTTTAGATAAAGAGTCTTCTT
AAAAATAACTAAACTGTAGGAATTTATATTTAATTATGCGTGGACCCGGG
TTCAACTCCCGCCAGCTCCACCA

TABLE 28 tmDNA Sequence for *Mycoplasma pirum*

(SEQ ID NO: 36)
GGGGAGTCATGGTTTTGACATGAATGATGGACCCATAGAGGCAGTGGGGT
ATGCCCCTTATAGCTCAAGGTTTAAATTAACCGACAAAACTGACGAAAAC
GTTGCCGTTGATACAAATTTATTAATCAACCAACAAGCTCAATTTAACTA
CGCATTTGCATAGTATAAAAAAATAAATTGTGCTACTCATTGTAATTAGG
TTACTAAATTACTTTGTTTTATATAGTCCTGTAACTAGTTCTAGTGATGT
CTATAAACTAGAATGAGATTTATAGACTTATTTGTTGGCGGTTGTGCCAT
AGCCTAAATCAACAAAGACAATTTATTTATGGTACTAAACTGTAGATTCT
ATGATGAAATATTTGTGGAAACGGGTTCGATTCCCGCCATCTCCACCA

TABLE 29 tmDNA Sequence for *Mycoplasma salivarium*

(SEQ ID NO: 37)
GGGGCTGATTCTGGATTCGACAGGCATTCGATTCATTATGTTGCAGTGGT
TTGCAAACCATAAGGCACTAGGCTTTTTTAAACGCAAAAGACCAAAAAAC
AGAAGATCAAGCAGTTGATCTAGCATTTATGAATAATTCACAAATGCAAT
CAAATCTAGTTTTCGCTTAGTAAAATTAGTCAATTTATTATGGTGCTCAA
CATAATAAATGGTAGTATGAGCTTAATATCATATGATTTTAGTTAATATG
ATAGGATTTGTAACTAAACTATGTTATAGAAATTTGTAAATTATATATAT
GACATAGGAAATTTAATTTACTAAACTGTAGATGCATAATGTTGAAGATG
TGTGGACCGGGGTTCAACTCCCGCCAGCTCCACCA

TABLE 30 tmDNA Sequence for *Herpetosiphon aurantiacus*

(SEQ ID NO: 38)
GGGGGCGGAAAGGATTCGACGGGGAGGGCCAATCGTAAGTGGCAAGCCGA
GACGCTGAGCCTCGTTAAATCGGCAACGCCATTAACTGGCAAAAACACTT
TCCGCGCTCCTGTAGCGCTTGCTGCCTAATTAAGGCAACACGTCTCTACT
AGCCTCAGCCCGATGGGCTTGTAGCGGCGACACTTAGTCGGGTCGCTCCC
CTAGTTATGCTCTGTGGGCTAGGGGCTAAGATTAACAGGCTGGTCGTGGCC
CGCTTTGTCTATCGGGTGGTGCACCGATAAGATTTAATCAATAGACTACG
CTTGTAGATGCTTGCGGTTTAACTTTTTGGACGCGGGTTCGATTCCCGCC
GCCTCACCACCA

TABLE 31 tmDNA Sequence for *Thermomicrobium roseum*
(352 nts, temp. 70 degrees, green non sulfur)

(SEQ ID NO: 39)
GGGGCTGATTCTGGATTCGACAGGGCCGTAGGTGCGAGGATTGCAGGTCG
AGGTCGCCCACGAACTCGTAAAAAGGGGCAGCCAAGTAACTGGCGAGCGC
GAACTCGCTCTGGCTGCGTAATTCACGCAGCCACGTCTGCCCGGACCCTT
CCCTGGTGGGTTCGGAGCGGGCGCCGCAAGACCGGGGTGCCCCTGGCCCA
AGCGCCGGTGCGGGCCAGGTCAAGCGTGATCCGGCTCGGCTGACCGGGAT
CCTGTCGGTGGGAGCCTGGCAGCGACAGTAGAACACCGACTAAGCCTGTA
GCATATCCTCGGCTGAACGCTCTGGACGCGGGTTCAACTCCCGCCAGCTC
CACCA

TABLE 32 tmDNA Sequence for *Chlorobium limicola*

(SEQ ID NO: 40)
GGGGCTGATTCTGGATTCGACAGGATACGTGTGAGATGTCGTTGCACTCC
GAGTTTCAGCATGGACGGACTCGTTAAACAAGTCTATGTACCATTAGATG
CAGACGATTATTCGTATGCAATGGCTGCCTGATTAGCACAAGTTAACTCA
GACGCCATCGTCCTGCGGTGAATGCGCTTACTCTGAAGCCGCCGGATGGC
ATAACCCGCGCTTGAGCCTACGGGTTCGCGCAAGTAAGCTCCGTACATTC
ATGCCCGAGGGGCTGTGCGGGTAATTTCTCGGGATAAGGGGACGAACGCT
GCTGGCGGTGTAATCGGCCCACGAAAACCCAATCACCAGAGATGAGTGTG
GTGACTGCATCGAGCAGTGTTTTGGACGCGGGTTCAACTCCCGCCAGCTC
CACCA

TABLE 33 tmDNA Sequence for *Pirellula staleyi*
(*planctomyces*)

(SEQ ID NO: 41)
GGGGCTGATTCTGGATTCGACCGGATAGCCTGAAGCGAATACGGCGTGCC
GTGGTTGATCAGATGGCCACGTAAAAAGCTGATCACAAACTTAACTGCCG
AGAGCAATCTCGCACTTGCTGCCTAACTAAACGGTAGCTTCCGACTGAGG
GCTTTAGCCGGAGAGGCCCAAAAGTTGGTCACCAAATCCGGACCGCCTCG
TGCCATGATCGAAACGCACGAGGTCAAAAAAGTTTCGATCTAGTGCAGGG

TABLE 33-continued tmDNA Sequence for *Pirellula staleyi*
(planctomyces)

TGTAGCCAGCAGCTAGGCGACAAACTGTGCAAAAATCAAATTTTCTGCTA
CGCACGTAGATGTGTTCGTGAAAATGTCTCGGGACGGGGGTTCAACTCCC
GCCACTCCACCA

TABLE 34 tmDNA Sequence for *Planctomyces limnophilus*

(SEQ ID NO: 42)
GGGGCTGATTCTGGATTCGACAACCTCTCAAGAGGAGCGTGGCCACTATG
GGACTCGATTATGTTGAATTCGTCATGGATCTTGAAGAGACCTTCGACAT
CAAACTGGATGACAAACATTTTTCAGCAGTCAAAACACCACGCGATTTGG
CAATCATTATTCGGGATCAATTAGCTGCTGAAGGCAGAATCTGGGATGAA
TCGAATGCTTTTCGCAAAATCTCGAATTTGAATTGGACGATGTTGCCCGA
GTTCCGGATGTGGACTCAAATCAAAAGCTCTCTACCAGTTTCTTTTCACC
GACTGCGTCCCAGCACCCGTCTCGTTCAACTCCCGCCANTCCACCA

TABLE 35 tmDNA Sequence for *Planctomyces maris*

(SEQ ID NO: 43)
GGGGCTGATTCTGGATTCGACTGGTTCACCGTATGTTAAGGTGGCGGTGC
CGTGGTTGATCAGTTGGCCACGTAAAAAGCTGATCACAATCTAATTGCAA
ACAAGCAATTTTCAATGGCTGCTTAATAAAAGCAACCCCAGCTTAGGAAT
CTCTGTCTGAGGAGTCCGACAGCTGGTCACAAAATCAGACTGGTATCAGA
TCAATGTCCGCTCCGTCTGATACGAGATTCGTGGTGGACTGGTTTCCAAC
AGGCTCTGTTTATCGTGCCCGAAGAAACGAGACTCAAACGATAAAATATG
CACCGTAGAGGCTTTAGCTGAGGGTTCACAGGACGCGGGTTCAACTCCCG
CCAGCTCCACCA

TABLE 36 tmDNA Sequence for *Alcaligenes eutrophus*

(SEQ ID NO: 44)
GGGGTTGATTCTGGATTCGACGTGGGTTACAAAGCAGTGGAGGGCATACC
GAGGACCCGTCACCTCGTTAATCAATGGGAATGCAATAACTGCTAACGAC
GAACGTTACGCACTGGCCGCTTAATTGCGGCCGTCCTCGCACTGGCTCGC
TGACGGGCTAGGGTCGCAAGACCACGCGAGGTCATTTACGTCAGATAAGC
TCCGGAAGGGTCACGAAGCCGGGGACGAAAACCTAGTGACTCGCCGTCGT
AGAGCGTGTTCGTCCGCGATGCGCCGGTTAAATCAAATGACAGAACTAAG
TATGTAGAACTCTCTGTGGAGGGCTTACGGACGCGGGTTCAACTCCCGCC
AGCTCCACCA

TABLE 37 tmDNA Sequence for *Alcaligenes faecalis*
(beta proteobacteria)

(SEQ ID NO: 45)
GGGGGCGGAAAGGATTCGACGGGGGTCAAGAAGCAGCACAGGGCGTGTCG
AGCACCAGTACGCTCGTAAATCCACTGGAAAACTATAAACGCCAACGACG
AGCGTTTCGCTCTAGCCGCTTAAGGCTGGGCCACTGCACTAATTTGTCTT
TGGGTTAGGTAGGGCAACCTACAGCAGTGTTATTTACAAAGAATCGAATC
GGTCTCGCCACGAAGTCCGGTTCTAAAACTTAGTGGATCGCCAAGGAAA
GGCCTGTCAATTGGCATAGTCCAAGGTTAAAACTTAAAATTAATTGACTA
CACATGTAGAACTGTCTGTGGACGGCTTGCGGACGGGGGTTCGATTCCCC
CGCCTCCACCA

TABLE 38 tmDNA Sequence for *Chromobacterium violaceum*
(beta-purple)

(SEQ ID NO: 46)
GGGGCTGATTCTGGATTCGACGGGGGTTGCGAAGCAGATGAGGGCATACC
GGGATTTCAGTCACCCCGTAAAACGCTGAATTTATATAGTCGCAAACGAC
GAAACTTACGCTCTGGCAGCCTAACGGCCGGCCAGACACTACAACGGTTC
GCAGATGGGCCGGGGCGTCAAAACCCTGTAGTGTCACTCTACATCTGCT
AGTGCTGTTCCGGGTTACTTGGTTCAGTGCGAAATAATAGGTAACTCGCC
AAAGTCCAGCCTGTCCGTCGGCGTGGCAGAGGTTAAATCCAAATGACACG
ACTAAGTATGTAGAACTCACTGTAGAGGACTTTCGGACGCGGGTTCAACT
CCCGCCAGCTCCACCA

TABLE 39 tmDNA Sequence for *Hydrogenophaga palleroni*
(beta-purple)

(SEQ ID NO: 47)
GGGGCTGATTCTGGATTCGACGTGGGTTCGGACGCGCAGCAGGGCATGTC
GAGGTTCTGTCACCTCGTAAATCAGCAGAAAAAAACCAACTGCAAACGAC
GAACGTTTCGCACTCGCCGCTTAAACACCGGTGAGCCTTGCAACAGCAGG
CCGATGGGCTGGGCAAGGGGGTCGCAAGACCTCCCGGCTGCAAGGTAATT
TACATCGGCTGGTTCTGCGTCGGGCACCTTGGCGCAGGATGAGATTCAAG
GATGCTGGCTTCCCGTTTAGCGTGCCACTGCGCGACTCGGGCGGCGAGAC
CCAAATCAGACGGCTACACATGTAGAACTGCTCGAAAAAGGCTTGCGGAC
GGGGGTTCAACTCCCGCCAGCTCCACCA

TABLE 40 tmDNA Sequence for *Methylobacillus glycogenes*
(beta-purple)

(SEQ ID NO: 48)
GGGGGCGGAAAGGATTCGACGGGGGTTGCAAAGCAGCGCAGGGCATACCG
AGGCCTAGTCACCTCGTAAATAAACTAGAACAAGTATAGTCGCAAACGAC
GAAACTTACGCTCTAGCCGCTTAATCCCGGCTGGACGCTGCACCGAAGGG
CCTCTCGGTCTGGGTGGGGTAACCCACAGCAGCGTCATTAAGAGGATCG
TGCGATATTGGGTTACTTAATATCGTATTAAATCCAAGGTAACTCGCCTG
CTGTTTGCTTGCTCGTTGGTGAGCATCAGGTTAAATCAAACAACACAGCT
AAGTATGTAGAACTGTCTGTGGAGGGCTTGCGGACGGGGGTTCGATTCCC
GCCGCCTCACCACCA

TABLE 41 tmDNA Sequence for *Nitrosomonas cryotolerans*
(beta-purple)

(SEQ ID NO: 49)
GGGGCTGATTCTGGATTCGACGTGGGTTGCAAAGCAGCGCAGGGCATACC
GAGGACCAGAATACCTCGTAAATACATCTGGAAAAAAATAGTCGCAAACG
ACGAAAACTACGCTTTAGCCGCTTAATACGGCTAGCCTCTGCACCGATGG
GCCTTAACGTCGGGTCTGGCAACAGACAGCAGAGTCATTAGCAAGGATCG
CGTTCTGTAGGGTCACTTTACAGAACGTTAAACAATAGGTGACTCGCCTG
CCATCTCAGCCCGCCAGCTGGCGGTTGTCAGGTTAAATTAAAGAGCATGGCT
AAGTATGTAGAACTGTCTGTAGAGGACTTGCGGACGCGGGTTCAACTCCC
GCCAGTCCACCA

TABLE 42 tmDNA Sequence for *Pseudomonas testosteroni*

(SEQ ID NO: 50)
GGGGCTGATTCTGGATTCGACGTGGGTTCGGGACCGGTGCGGTGCATGTC
GAGCTTGAGTGACGCTCGTAAATCTCCATTCAAAAAACTAACTGCAAACG
ACGAACGTTTCGCACTCGCCGCTTAATCCGGTGAGCCTTGCAACAGCACG
CTAGTGGGCTGGGCAAGGGGGTAGCAATACCTCCCGGCTGCAAGGGAATT
TCATTAGCTGGCTGGATACCGGGCTTCTTGGTATTTGGCGAGATTTTAG
GAAGCTGGCTACCCAAGCAGCGTGTGCCTGCGGGGTTTGGGTGGCGAGAT

TABLE 42-continued tmDNA Sequence for *Pseudomonas testosteroni*

TTAAAACAGAGCACTAAACATGTAGATCTGTCCGGCGAAGGCTTACGGAC
GCGGGTTCAACTCCCGCCAGCTCCACCA

TABLE 43 tmDNA Sequence for *Ralstonia pickettii* (*Burkholderia*)

(SEQ ID NO: 51)
GGGGGCGGAAAGGATTCGACGGGGGTTGCGAAGCAGCGGAGGGCATACCG
AGGACCCGTCACCTCGTTAATCAATGGGAATGCAATAACTGCTAACGACG
AACGTTACGCACTGGCAGCCTAAGGGCCGCCGTCCTCGCACTGGCTCGCT
GACGGGCTAGGGTCGCAAGACCAGCGAGGTCATTTACGTCAGATAAGCTT
TAGGTGAGTCACGGGCCTAGAGACGAAAACTTAGTGAATCGCCGTCGTAG
AGCGTGTTCGTCCGCGATGCGCGGTTAAATCAAATGACAGAACTAAGTA
TGTAGAACTCTCTGTGGAGGGCTTGCGGACGCGGGTTCGATTCCCGCCGC
CTCACCACCA

TABLE 44 tmDNA Sequence for *Variovax paradoxus* (*pseudomonas* sp.)

(SEQ ID NO: 52)
GGGGCTGATTCTGGATTCGACGTGGGTTCGGAGTCGCAGCGGGGCATGTC
GAGCTGAATGCGCTCGTAAAACAGATTCAAACAAACTAACTGCAAACGAC
GAACGTTTCGCACTCGCTGCTTAATTGCCAGTGAGCCTTGCAACAGTTGG
CCGATGGGCTGGGCAAGGGGGTCTGGAGCAATCCTGACCTCCCGGCTGCA
AGGATAACTACATGGGCTGGCTCCGATCCGGGTACCTTGGGTCGGGGCGA
GAAAATAGGGTACTGGCGTCCGGTTTAGCGTGTGACTGCGCGACTCCGGA
AGCGAGACTCAAAACAGATCACTAAACATGTAGAACTGCGCGATGAAGGC
TTGCGGACGGGGGTTCAACTCCCGCCAGCTCCACCA

TABLE 45 tmDNA Sequence for *Bdellovibrio bacteriovorus* (delta proteobacterie)

(SEQ ID NO: 53)
GGGGGCGGAAAGGATTCGACGGGGGTGCTGAAGCATAAGGAGCATACCGG
GGCGGATGAGGACCTCGTTAAAAACGTCCACTTTGTAATTGGCAACGATT
ACGCACTTGCAGCTTAATTAAGCAGCAGATCAACCTTGTGGTGGTTCCG
CACTTGGATTGATCGTCATTTAGGGACCTCGGCGTGTTGGGTTTTCTCCA
GCAGACATGCTTAAATTTACTGGGGAGAGGTCTTAGGGATTTTGTCTGT
GGAAGCCCGAGGACCAATCTAAAACACTGACTAAGTATGTAGCGCCTTAT
CGTGGATCATTTGCGGACGGGGGTTCGATTCCCGCCGCCTCCACCA

TABLE 46 tmDNA Sequence for *Myxococcus xanthus* (delta proteobacterie)

(SEQ ID NO: 54)
GGGGGCGGAAAGGATTCGACGGGGGCATTGAAGTTCGAGACGCGTGCCGA
GCTTGTCAGGTAGCTCGTAAATTCAACCCGGCAAAGACACAAAAGCCAAC
GACAACGTTGAGCTCGCGCTGGCTGCCTAAAAACAGCCCATAGTGCGCGG
TCCCCCGCCCTCGGCCTGTGGGGTTGGGACAGACCGTCATAATGCAGGC
TGGCTGCCGAGGGTGCCTGGACCCGAGGTGGCGAGATCTTCCCAGGACCG
GCTCTGAGTATCCCGTCCGTGGGAGCCTCAGGGACGTAGCAAATCGGGA
CTACGCACGTAGGGTCGAAGAGCGGACGGCTTTCGGACGCGGGTTCGATT
CCCGCCGCCTCCACCA

TABLE 47 tmDNA Sequence for *Sulfurospirillum Deleyianum*

(SEQ ID NO: 55)
GGGGGCTGATTCTGGATTCGACAGGAGTAGTTTTAGCTTATGGCTGCATGT
CGGGAGTGAGGGTCTTCCGTTACACAACCTTCAAACAATAACTGCTAACA
ACAGTAACTATCGTCCTGCTTACGCGCTAGCTGCGTAAGTTTAACAAATA
ATGGACTGCTCTCCCCTTTGATGCTATCTTAGGAGGTCTTGGAGAGTATC
ATAGATTTGATAGCTATATTACATGAACGCCTTTACATGTAATGAAGTTA
AAGGCTCGTTTTGCGTAGTTTTCTGATTGTTGTACGAAGCAAAATTAAAC
ACTATCAACAATATCTAAGCATGTAGACGTCATAGGTGGCTATTTTTGGA
CTGCGGGTTCAACTCCCGCCAGCTCCACCA

TABLE 48 tmDNA Sequence for *Chromatium vinosum*

(SEQ ID NO: 56)
GGGGCTGATTCTGGATTCGACGTGGGTCGCGAAACCTAAGGTGCATGCCG
AGGTGCGGTTGACCTCGTAAAACCCTCCGCAAACTTATAGTTGCCAACGA
CGACAACTACGCTCTCGCTGCTTAATCCCAGCGGGCCTCTGACCGTCACT
TGCCTGTGGGCGGCGGATTCCAGGGGTAACCTCACACAGGATCGTGGTGA
CGGGAGTCCGGACCTGATCCACTAAAACCTAACGGAATCGCCGACTGATC
GCCCTGCCCTTCGGGCGGCAGAAGGCTAAAAACAATAGAGTGGGCTAAGC
ATGTAGGACCGAGGGCAGAGGGCTTGCGGACGCGGGTTCAACTCCCGCCA
GCTCCACCA

TABLE 49 tmDNA Sequence for *Pseudomonas fluorescens* (gamma proteobacteria)

(SEQ ID NO: 57)
GGGGCTGATTCTGGATTCGACGCCGGTTGCGAACCTTTAGGTGCATGCCG
AGTTGGTAACAGAACTCGTAAATCCACTGTTGCAACTTTCTATAGTTGCC
AATGACGAAACCTACGGGGAATACGCTCTCGCTGCGTAAGCAGCCTTAGC
CCTTCCCTCCTGGTACCTTCGGGTCCAGCAATCATCAGGGGATGCTGTA
AACCCAAAGTGATTGTCATATAGAACAGAATCGCCGTGCAGTACGTTGTG
GACGAAGCGGCTAAAACTTACACAACTCGCCCAAAGCACCCTGCCCGTCG
GGTCGCTGAGGGTTAACTTAATAGACACGGCTACGCATGTAGTACCGACA
GCAGAGTACTGGCGGACGCGGGTTCAACTCCCGCCAGCTCCACCA

TABLE 50 tmDNA Sequence for *Borrelia afzeli*

(SEQ ID NO: 58)
GGGGCTGATTCTGGATTCGACTGAAAATGCTAATATTGTAAGTTGCAAGC
AGAGGGAATCTCTTAAAACTTCTAAAATAAATGCAAAAAATAATAACTTT
ACAAGTTCAAACCTTGTAATGGCTGCTTAAGTTAGCAGAGAGTTTTGTTG
AATTTGGCTTTGAGATTCACTTATACTCTTTTAGACATCGAAGCTTGCTT
AAAAATGTTTTCAAGTTGATTTTTAGGGACTTTTATACTTGAGAGCAATT
TGGCGGTTTGCTAGTATTTCCAAACCATATTGCTTAGTAAAATACTAGAT
AAGCTTGTAGAAGCTTATAGTATTGTTTTTAGGACGCGGGTTCAACTCCC
GCCAGTCCACCA

TABLE 51 tmDNA Sequence for *Borrelia crociduarae*

(SEQ ID NO: 59)
GGGGCTGATTCTGGATTCGACTAAGAACTTTAGTAGCATAAATGGCAAGC
AGAGTGAATCTCTTAAAACTTCTTTAATAAATGCAAAAAATAATAACTTT
ACAAGTTCAGATCTTGTAATGGCTGCTTAATTTAGCAGAGAGTTTTGTTG
GATTTTGCTTTCAACTTATACTCTTTAAGACATCAAAGTATGCC
TAAAAATGTTTCAAGTTGATTTTTAGGGACCTTTAAACTTGAGAGTAATT
TGGTGGTTTGCTTGTTTTCCAAGCCTTATTGCTTTTTCTAAAAATTAGCT
AAGCTTGTAGATATTTATGATATTATTTTTAGGACGCGGGTTCAACTCCC
GCCAGTTCCACCA

TABLE 52 tmDNA Sequence for *Borrelia hermsii*

(SEQ ID NO: 60)
GGGGCTGATTCTGGATTCGACTAAAAACTTTAGTAGCATAAATTGCAAGC
AGAGGGAATCTCTTAAAACTTCTTTAATAAATGCAAGAAATAATAACTTT
ACAAGTTCAAATCTTGTAATGGCTGCTTAAATTAGCAGAGAGTTCTGCTG
GATTTTGCTTTGAGGTTCAGCTTATACTCTTTTAAGACATCAAAGCTTGC
TTAAAAATATTTCAAGTTGATTTTTAGGGACTTTTAAATTTGAGAGTAAT
TTGGCGGTTTGCTAGTTTTTCCAAACCTTATTACTTAAAGAAAACACTAG
CTAAGCTTGTAGATATTTATGATATTATTTTTAGGACGCGGGTTCAACTC
CCGCCAGCTCCACCA

TABLE 53 tmDNA Sequence for *Borrelia garinii*

(SEQ ID NO: 61)
GGGGCTGATTCTGGATTCGACTGAAAATGCGAATATTGTAAGTTGCAGGC
AGAGGGAATCTCTTAAAACTTCTAAAATAAATGCAAAAAATAATAACTTT
ACAAGCTCAAACCTTGTAATGGCTGCTTAAGTTAGCAGGGAGTTTCGTTG
AATTTGGCTTTGAGGTTCACTTATACTCTTTTCGATATCGAAGCTTGCTT
AAAAATGTTTTCAAGTTAATTTTTAGGGACTTTTGTACTTGAGAGCAATT
TGGCGGTTTGCTAGTATTTCCAAACCATATTGCTTAAGTAAAATGCTAGA
TAAGCTTGTAGAAGCTTATAATATTGTTTTTAGGACGCGGGTTCAACTCC
CGCCAGTCCACCA

TABLE 54 tmDNA Sequence for *Thermodesulfobacterium commune* (70 degrees)

(SEQ ID NO: 62)
GGGGGCGGAAAGGATTCGACGGGGATAGGTAGGATTAAACAGCAGGCCGT
GGTCGCACCCAACCACGTTAAATAGGGTGCAAAAACACAACTGCCAACGA
ATACGCCTACGCTTTGGCAGCCTAAGCGTGCTGCCACGCACCTTTAGACC
TTGCCTGTGGGTCTAAAGGTGTGTGACCTAACAGGCTTTGGGAGGCTTAA
TCGGTGGGGTTAAGCCTCCCGAGATTACATCCCACCTGGTAGGGTTGCTT
GGTGCCTGTGACAAGCACCCTACGAGATTTTCCCACAGGCTAAGCCTGTA
GCGGTTTAATCTGAACTATCTCCGGACGCGGGTTCGATTCCCGCCGCCTC
CCCACCA

TABLE 55 tmDNA Sequence for *Thermotoga neapolitana* (*Thermotogales*)

(SEQ ID NO: 63)
GGGGGCGGAAAGGATTCGACGGGGATGGAGTCCCCTGGGAAGCGAGCCGA
GGTCCCCACCTCCTCGTAAAAAAGGTGGGAACACGAATAAGTGCCAACGA
ACCTGTTGCTGTTGCCGCCTAATAGATAGGCGGCCGTCCTCTCCGGAGTT
GGCTGGGCTCCGGAAGAGGGCGTGAGGGATCCAGCCTACCGATCTGGGCT
CCGCCTTCCGGCCCGGATCGGGAAGGTTCAGGAAGGCTGTGGGAAGCGAC
ACCCTGCCCGTGGGGGGTCCTTCCCGAGACACGAAACACGGGCTGCGCTC
GGAGAAGCCCAGGGGCCTCCATCTTCNGACGCGGGTTCGATTCCCGCCAC
CTCCACCA

TABLE 56 tmDNA Sequence for *Deinococcus proteolyticus*

(SEQ ID NO: 64)
GGGGGCGGAAAGGATTCGACGGGGGAACGGAAAGCGCTGCTGCGTGCCGA
GGAGCCGTTGGCCTCGTAAACAAACGGCAAAGCCATTAACTGGCGAAAAT
AACTACGCTCTCGCTGCTTAAGTGAGACAGTGACCACGTAGCCCCGCCTT
TGGCGACGTGTGAACTGAGACAAAAGAAGGCTAGCTTAGGTGAGGTTCCA
TAGCCAAAAGTGAAACCAAATGGAAATAAGGCGGACGGCAGCCTGTTTGC
TGGCAGCCCAGGCCCGACAATTTAAGAGCAGACTACGCACGTAGATGCAC
GCTGGATGGACCTTTGGACGCGGGTTCGATTCCCGCCAGCTCCACCA

TABLE 57 tmDNA Sequence for *Prosthecobacter fusiformis* (*verrucomicrobia*)

(SEQ ID NO: 65)
GGGGCTGATTCTGGATTCGACGGGGAGTACAAGGATCAAAAGCTGCAAGC
CGAGGTGCCGTTACCTCGTAAAACAACGGCAAAAAAGAAGTGCCAACACA
AATTTAGCATTAGCTGCTTAATTTAGCAGCTACGCTCTTCTAACCCGGGC
TGGCAGGGTTAGAAGGGTGTCATAATGAGCCAGCTGCCCCTTCCGACTCC
CCTAAGGAAGGGAAAGATGTAGGGGATAGGTGCTTACAGAATCCTGCGGG
AGGGAGTCTGTAAGTGCCGAAAAGTTAAAACTCCCGCTAAGCTTGTAGAG
GCTTTTGATTCTTGCTCTCTGGACGCGGGTTCAACTCCCGCCAGCTCCAC
CA

TABLE 58 tmDNA Sequence for *Verrucomicrobium spinosum* (*verrucomicrobium*)

(SEQ ID NO: 66)
GGGNNNNATTTGGAATTCGCCGAATGCTAGAAGTGGAGGCTGCATGCCGC
GGATGATTCGTTGGCCGCTTTACCAATTCGGATCAAACAACTAAATGCGG
ACTCTAACGAGCTTGCCCTCGCCGCTTAATTGACGGTGACGTTCCTCCAG
TGAAGTCTGTGAATTGGAGGAGCGACTACTTACAGGCTGGCCAAAAGAGC
GGGCGACCGGCCCCAAGGCGAGATCTACAGGCCGCTGGATGGACGGCATC
CTGGCCAGTAGGAGGCTGGACATCGAGATCAAATNATTGCCTGAGCATGGA
GACGCTTTCATAAAGGNGTTCGGACAGGG

Example 4

Alignment of tmRNA Sequences

The newly discovered tmRNA sequences and several known tmRNA sequences were aligned to identify target sites for drug development. The alignments of the sequences are shown in FIGS. 3A-11B. The nucleotides in the tmRNA sequences of these figures exist in several motifs (Felden et al., 1999). These motifs include nucleotides considered to be in RNA helices (Watson-Crick base-pairs GC or AU, or GU Wobble base-pairs). Nucleotides that are in in single stranded RNA domains, hence not base-paired. Some nucleotides in the single stranded domains are universally conserved nucleotides. Other nucleotides are the exceptions to a quasi-sequence conservation in the sequences alignment. Several nucleotides exist in well established non-canonical structural motifs in RNA structures; for example AG-GA pairs, AA pairs, etc. Some nucleotides are universally conserved Wobble GU base-pairs.

All the gene sequences have been decomposed in several structural domains that have been indicated with names at the top of each block of sequences. These domains are respectively from the 5'-end to the 3'-end of the sequences: H1, H5, H2, PK1, H4, PK2, PK3, PK4, H5 and H6. The bars delineate all the structural domains. H means helices and PK means pseudoknot. A pseudoknot is made of the pairing of parts of an RNA-loop with an upstream sequence. Consequently, two helices are made (shown in Felden et al., 1999) for all the 4 pseudoknots PK1 to PK4 for each sequence. Moreover, the tRNA-like domain as well as the coding sequence, namely the two functional units of the molecule, have also been indicated for each sequence.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria.

Common Structural Features for Drug Targeting:

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. The PK1 structural domain is strictly conserved in the tmRNAs and is located upstream of the coding sequence. Since these pseudoknots are not found in all canonial transfer RNAs, they can also be targeted with specific drugs. Disruption of either PK1 or PK2 or PK3 with a specific drug would lead to inactive tmRNA molecules in vivo.

Specific Structural Features in Each Phylum that could be Targeted by Drugs:

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding, which has been shown for *Escherichia coli*, and thus, is also available for interaction with other drugs. Moreover, this is a critical functional domain of the molecule in its quality-control mechanism in cells. In addition, this coding sequence would be the ideal target to use for designing specific PCR-based diagnostic assays for infection diseases.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides* thetaiotaomicron and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Andersson, S. G. et al. (1998). *Nature* 396:133-140.
Ando, H. et al. (1996). *Genes & Genet. Syst.* 71:47-50.
Breithaupt, H. (1999). *Nature Biotechnol.* 17:1165-1169.
Felden, B. et al. (1996). *Biochimie* 78:979-983.
Felden, B. et al. (1997). *RNA* 3:89-103.
Felden, B. et al. (1998). *EMBO J.* 17:3188-3196.
Felden et al. (1999). *Biochim. Biophys. Acta* 1446:145-148.
Gray, M. W. and Spencer, D. F. (1996). In *Evolution of Microbial Life*, Cambridge University Press, pp. 109-126.
Hickerson, R. P. et al. (1998). *J. Mol. Biol.* 279:577-587.
Himeno, H. et al. (1997). *J. Mol. Biol.* 268:803-808.
Huang, C. et al. (2000). *EMBO J.* 19:1098-1107.
Julio, S. M et al. (2000). *J. Bacteriol.* 182:1558-1563.
Keiler, K. C. et al. (1996). *Science* 271:990-993.
Komine, Y. et al. (1994). *Proc. Natl. Acad. Sci. USA* 20:9223-9227.
Mateeva, O. et al. (1997). *Nucleic Acids Res.* 25:5010-5016.
Muto, A. et al. (1998). *Trends Biochem. Sci.* 1:25-29.
Nameki, N. et al. (1999). *J. Mol. Biol.* 286:733-744.
Nakemi, N. et al. (2000). *FEBS Lett.* 470:345-349.
*Remington's Pharmaceutical Sciences,* 18th Ed., Mack Publishing Co., Easton, Pa., 1990.
Tu, G. F. et al. (1995). *J. Biol. Chem.* 270:9322-9326.
Ushida, C. et al. (1994). *Nucleic Acids Res.* 16:3392-3396.
Williams, K. P. (1999). *Nucleic Acids Res.* 27:165-166.
Williams, K. P. and Bartel, D. P. (1996). *RNA* 2:1306-1310.
Wower, J. and Zwieb, C. (1999). *Nucleic Acids Res.* 27:167.
Yang, D. et al. (1985). *Proc. Natl. Acad. Sci. USA* 82:4443-4447.

What is claimed is:

1. An isolated nucleic acid sequence selected from the group consisting of a tmRNA sequence for *Neisseria gonorrhoeae*, a tmDNA sequence encoding said tmRNA sequence, and a full-length complement of said tmDNA sequence, wherein the tmRNA sequence for *Neisseria gonorrhoeae* has the sequence set forth in SEQ ID NO:146.

2. A method for diagnosing a bacterial infection associated with *Neisseria gonorrhoeae* comprising determining the presence of a bacterial nucleic acid sequence selected from the group consisting of a tmRNA sequence for *Neisseria gonorrhoeae*, a tmDNA sequence encoding said tmRNA sequence, and a full-length complement of said tmDNA sequence, wherein the tmRNA sequence for *Neisseria gonorrhoeae* has the sequence set forth in SEQ ID NO:146.

3. The method of claim 2, wherein the determination is made by performing an amplification-based assay.

4. The isolated nucleic acid sequence of claim 1, wherein the nucleic acid sequence is the tmDNA sequence encoding the tmRNA sequence for *Neisseria gonorrhoeae*.

5. The method of claim 2, wherein the bacterial nucleic acid sequence is the tmDNA sequence encoding the tmRNA sequence for *Neisseria gonorrhoeae*.

6. The method of claim 3, wherein the bacterial nucleic acid sequence is the tmDNA sequence encoding the tmRNA sequence for *Neisseria gonorrhoeae*.

* * * * *

SEQUENCE LISTING

```
<160> NUMBER OF SEQ ID NOS: 175

<210> SEQ ID NO 1
<211> LENGTH: 21
<212> TYPE: DNA
<213> ORGANISM: Artificial
<220> FEATURE:
```

```
<223> OTHER INFORMATION: PCR primer

<400> SEQUENCE: 1
ggggctgatt ctggattcga c                                              21

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
tggagctggc gggagttgaa c                                              21

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
gggggcggaa aggattcgac g                                              21

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
tggaggcggc gggaatcgaa c                                              21

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
ggggatgtca tggttttgac a                                              21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tggagatggc gggaatcgaa c                                              21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ggggatgaca ggctatcgac a                                              21
```

```
<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagatggc gggacttgaa c                                              21

<210> SEQ ID NO 9
<211> LENGTH: 352
<212> TYPE: DNA
<213> ORGANISM: Acidobacterium capsulatum

<400> SEQUENCE: 9 ggggcggaa aggattcgac ggggttgact gcggcaaaga ggcatgccgg ggggtgggca     60
cccgtaatcg ctcgcaaaac aatacttgcc aacaacaatc tggcactcgc agcttaatta   120
aataagttgc cgtcctctga ggcttcgcct gtgggccgag gcaggacgtc atacagcagg   180
ctggttcctt cggctgggtc tgggccgcgg ggatgagatc cacggactag cattctgcgt   240
atcttgtcgc ttctaagcgc agagtgcgaa acctaaagga atgcgactga gcatggagtc   300
tcttttctga caccaatttc ggacgcgggt tcgattcccg ccgcctccac ca           352

<210> SEQ ID NO 10
<211> LENGTH: 353
<212> TYPE: DNA
<213> ORGANISM: Coprothermobacter proteolyticus

<400> SEQUENCE: 10 ggggcggaa aggattcgac ggggagtcgg agccttgagc tgcaggcagg gttggctgcc     60
acaccttaaa aagggtagca aggcaaaaat aaatgccgaa ccagaatttg cactagctgc   120
ttaatgtaag cagccgctct ccaaactgag gctgcataag tttggaagag cgtcaaccca   180
tgcagcggct cttaagcagt ggcaccagct gtttaagggt gaaagagtg gtgctgggca    240 gtgcggttgg gcttcctggg ctgcactgtc gagacttcac aggagggcta agcctgtaga   300
cgcgaaaggt ggcggctcgt cggacgcggg ttcgattccc gccgcctcca cca          353

<210> SEQ ID NO 11
<211> LENGTH: 399
<212> TYPE: DNA
<213> ORGANISM: Bacteroides thetaiotaomicron

<400> SEQUENCE: 11
ggggctgatt ctggattcga cagcgggcag aaatggtagg taagcatgca gtgggtcggt    60
aatttccact taaatctcag ttatcaaaac tttatctggc gaaactaatt acgctcttgc   120
tgcttaatcg aatcacagta gattagctta atccaggcac taggtgccag gacgagacat   180
cactcggaag ctgttgctcc gaagcattcc ggttcagtgg tgcagtaaca tcggggatag   240
tcagaagcgg cctcgcgttt ttgatgaaac tttagaggat aaggcaggaa ttgatggctt   300
tggttctgct cctgcacgaa aatttaggca aagataagca tgtagaaagc ttatgatttc   360
ctcgtttgga cgagggttca actcccgcca gctccacca                          399

<210> SEQ ID NO 12
<211> LENGTH: 352
<212> TYPE: DNA
<213> ORGANISM: Dictyoglomus thermophilum
```

-continued

```
<400> SEQUENCE: 12
ggggctgatt ctggattcga cagggagtac aaggatcaaa agctgcaagc cgaggtgccg      60
ttacctcgta aaacaacggc aaaaagaag tgccaacaca aatttagcat tagctgctta     120
atttagcagc tacgctcttc taacccgggc tggcagggtt agaagggtgt cataatgagc    180
cagctgcccc ttccgactcc cctaaggaag ggaaagatgt aggggatagg tgcttacaga    240
atcctgcggg agggagtctg taagtgccga aagttaaaa ctcccgctaa gcttgtagag     300
gcttttgatt cttgctctct ggacgcgggt tcaactcccg ccagctccac ca             352

<210> SEQ ID NO 13
<211> LENGTH: 313
<212> TYPE: DNA
<213> ORGANISM: Artificial
<220> FEATURE:
<223> OTHER INFORMATION: sequence isolated from rumenal fluid

<400> SEQUENCE: 13
acgcccttgt ctcagacgag ggcactcgtt aaaagtctg aaaagaataa ctgcagaacc       60
tgtagctatg gctgcttaat ttaagggcaa cccttggatc cgcctccatc ccgaaggggt     120
ggcatccgag tcgcaaatcg ggataggatg gatcttggca acgaggagta catccgaaat    180
ttgtcgctgc tggctgaagc atcgccgttc ctctttgggc gtggcaaggc aagattaaat    240
tcagaggata agcgtgtagt agcgagtgag taggtgtttt tggacgcggg ttcaagtccc    300
gccatctcca cca                                                       313

<210> SEQ ID NO 14
<211> LENGTH: 350
<212> TYPE: DNA
<213> ORGANISM: Artificial
<220> FEATURE:
<223> OTHER INFORMATION: sequence isolated from sludge

<400> SEQUENCE: 14
ggggatgtca tggttttgac agggaaccag gaggtgtgag atgcatgccg gagacgctgt      60
ccgctccgtt atcaagcagc aaacaaaact aattgcaaac aacaattact ccttagcagc    120
gtaagcagct aacgttcaac ctctccggac cgccgggagg ggatttgggc gtcgaaacag    180
cgcggacgct ccggatagga cgcccataat atccggctaa gaccatgggt ctggctctcg    240
cgggtctgat tgtcttccac cgcgcgggcc gcgatcaaag acaactaagc atgtaggttc    300
ttgcatggcc tgttctttgg acgcgggttc gattcccgcc atctccacca                350

<210> SEQ ID NO 15
<211> LENGTH: 359
<212> TYPE: DNA
<213> ORGANISM: Fibrobacter succinogenes

<400> SEQUENCE: 15
ggggctgatt ctggattcga cagggttacc gaagtgttag ttgcaagtcg aggtctcaga      60
cgagggctac tcgttaaaaa gtctgaaaaa aaataagtgc tgacgaaaac tacgcactcg    120
ctgcctaatt aacggcaacg ccgggcctca ttccgctccc atcggggtgt acgtccggac    180
gcaatatggg atagggaagt gtcatgcctg ggggcatctc ccgagatttt ctaggctggt    240
caaactccgc gccgaccttc ttgggcgtgg ataagacgag atcttaaatt cgaagggaac    300
acttgtagga acgtacatgg acgtgatttt ggacagggt tcaactcccg ccagctcca     359
```

<210> SEQ ID NO 16
<211> LENGTH: 350
<212> TYPE: DNA
<213> ORGANISM: Fusobacterium mortiferum

<400> SEQUENCE: 16

```
ggggctgatt ctggattcga cggggttatg aggttatagg tagcatgcca ggatgaccgc      60
tgtgagaggt caacacatcg tttagatgga aacagaaatt acgctttagc tgcttaatta     120
gtcagctcac ctctggtttc tctcttctgt aggagaatcc aaccgaggtg ttaccaatat     180
acagattacc tttagtgatt tctctaagct caaagggaca ttttagagaa tagcttcagt     240
tagccctgtc tgcgggagtg attgttgcga aataaaatag tagactaagc attgtagaag     300
cctatggcgc tggtagtttc ggacacgggt tcaactcccg ccagctccaa                350
```

<210> SEQ ID NO 17
<211> LENGTH: 377
<212> TYPE: DNA
<213> ORGANISM: Corynebacterium xerosis

<400> SEQUENCE: 17

```
ggggctgatt ctggattcga cttcgtacat tgagccaggg gaagcgtgcc ggtgaaggct      60
ggagaccacc gcaagcgtcg cagcaaccaa ttaagcgccg agaactctca gcgcgactac     120
gccctcgctg cctaagcagc gaccgcgtgt ctgtcagacc gggtaggcct ctgatccgga     180
ccctggcatc gtttagtggg gctcgctcgc cgacttggtc gcaagggtcg gcggggacac     240
tcacttgcga ctgggcccgt catccggtca tgttcgactg aaccgagggg ccgagcagag     300
accacgcgcg aactgcgcac ggagaagccc tggcgaggtg acggaggacc cgggttcaac     360
tcccgccagc tccacca                                                   377
```

<210> SEQ ID NO 18
<211> LENGTH: 372
<212> TYPE: DNA
<213> ORGANISM: Micrococcus luteus
<220> FEATURE:
<221> NAME/KEY: misc_feature
<222> LOCATION: (1)..(372)
<223> OTHER INFORMATION: n is an unknown base

<400> SEQUENCE: 18

```
ggggctattc tggattcgac ggtgtgtgtc gcgtcgggag aagcgggccg aggatgcaga      60
gtcatctcgt caaacgctct ctgcaaacca ataagtgccg aatccaagcg cactgacttc     120
gctctcgctg cctgatcagt gatcgagtcc gtcaccccga ggtcgctgtc gcctcggatc     180
gtggcgtcag ctagatagcc actgggcgtc accctcgccg ggggtcgtga cgccgacatc     240
aatccggctg ggtccgggtt ggccgcccgt ctgcgggacg gccaggaccg agcaacaccc     300
acagcagact gcgcccggag aagacctggc aacacctcat cggacgcggg ttcaactccc     360
gcantcccac ca                                                        372
```

<210> SEQ ID NO 19
<211> LENGTH: 372
<212> TYPE: DNA
<213> ORGANISM: Mycobacterium smegmatis

<400> SEQUENCE: 19

```
tcatctcggc ttgttcgcgt gaccgggaga tccgagtaga gacatagcga actgcgcacg      60
gagaggggct gattcctgga ttcgacttcg agcatcgaat ccagggaagc gtgccggtgc     120
```

```
aggcaagaga ccaccgtaag cgtcgttgca accaattaag cgccgattcc aatcagcgcg      180
actacgccct cgctgcctaa gcgacggctg gtctgtcaga ccgggagtgc cctcggcccg      240
gatcctggca tcagctagag ggacccaccc acgggttcgg tcgcgggacc tgtggggaca      300
tcaaacagcg actgggatcg agcctcgagg acatgccgta ggacccgggt tcaactcccg      360
ccagctccac ca                                                          372

<210> SEQ ID NO 20
<211> LENGTH: 355
<212> TYPE: DNA
<213> ORGANISM: Bacillus badius

<400> SEQUENCE: 20
gggggtgatt ctggattcga cagggatagt tcgagcttgg gctgcgagcc ggagggccgt       60
cttcgtacca acgcaaacgc ctaaatataa ctggcaaaaa agatttagct ttagctgcct      120
aatataggtt cagctgctcc tcccgctatc gtccatgtag tcgggtaagg ggtccaaact      180
tagtggacta cgccggagtt ctccgcctgg ggacaaagga agagatcaat caggctagct      240
gcccggacgc ccgtcgatag gcaaaaggaa cagtgaaccc caaatatatc gactacgctc      300
gtagacgttc aagtggcgtt atctttggac gtgggttcaa ctcccgccag ctcca           355

<210> SEQ ID NO 21
<211> LENGTH: 357
<212> TYPE: DNA
<213> ORGANISM: Bacillus brevis

<400> SEQUENCE: 21
gggggcggaa aggattcgac ggggatggta gagcatgaga agcgagccgg ggggttgcgg       60
acctcgtcac caacgcaaac gccattaact ggcaacaaac aactttctct cgctgcttaa      120
taaccagtga ggctctccca ctgcatcggc ccgtgtgccg tggatagggc tcaactttaa      180
cgggctacgc cggaggcttc cgcctggagc caaaggaaga agaccaatca ggctaggtgc      240
caggtcagcg cgtcactccg cgaatctgtc accgaaactc taaacgagtg actgcgctcg      300
gagatgctca tgtatcgctg ttttcggacg ggggttcgat tcccgccgcc tcaccca         357

<210> SEQ ID NO 22
<211> LENGTH: 354
<212> TYPE: DNA
<213> ORGANISM: Bacillus thermoleovorans

<400> SEQUENCE: 22
gggggcggaa aggattcgac gggggtaggt cgagcttaag cggcgagccg aggggggacgt       60 cctcgtaaaa acgtcaccta aagataactg gcaaacaaaa ctacgcttta gctgcctaat      120
tgctgcagct agctcctccc gccatcgccc gcgtggcgtt cgagggctc atatggagcg       180 ggctacgccc aaatccgccg cctgaggatg agggaagaga cgaatcaggc tagccgccgg      240
gaggcctgtc ggtaggcgga acggacggcg aagcgaaata taccgactac gctcgtagat      300
gcttaagtgg cgatgcctct ggacgtgggt tcgattcccg ccgcctcccc acca            354

<210> SEQ ID NO 23
<211> LENGTH: 384
<212> TYPE: DNA
<213> ORGANISM: Clostridium innocuum

<400> SEQUENCE: 23
gggggcggaa aggattcgac ggggatatgt ctggtacaga ctgcagtcga gtggttacgt       60
```

| | |
|---|---|
| aataaccaat taaatttaaa cggaaaaact aaattagcta acctctttgg tggaaaccag | 120 |
| agaatggctt tcgctgctta ataaccgata taggttcgca gccgcctctg catgcttctt | 180 |
| ccttgaccat gtggatgtgc gcgtaagacg caagggataa ggaatctggt ttgcctgaga | 240 |
| tcagattcac gaaaattctt caggcacatt catcagcgga tgttcatgac ctgctgatgt | 300 |
| cttaatcttc atggactaaa ctgtagaggt ctgtacgtgg ggctgtttct ggacaggagt | 360 |
| tcgattcccg ccgcctcacc acca | 384 |

<210> SEQ ID NO 24
<211> LENGTH: 349
<212> TYPE: DNA
<213> ORGANISM: Clostridium lentocellum

<400> SEQUENCE: 24

| | |
|---|---|
| gggggcggaa aggattcgac gggggtcaca tctactgggg c

<213> ORGANISM: Enterococcus faecium
<220> FEATURE:
<221> NAME/KEY: misc_feature
<222> LOCATION: (1)..(369)
<223> OTHER INFORMATION: n is an unknown base

<400> SEQUENCE: 27

```
ggggctgatt atggattcga caggatngtt gagcttgaat tgcgtttcgt aggttacggc    60
tacgttaaaa cgttacagtt aaatataact gctaaaaacg aaaacaattc tttcgcttta   120
gctgcctaaa aaccagctag cgaagatcct cccggcatcg cccatgtgct cgggtcaggg   180
tcctaatcga agtgggatac gctaaatttt tccgtctgta aaatttagag gagcttacca   240
gactagcaat acaagaatgc ctgtcactcg gcacgctgta aagcgaacct ttaaatgagt   300
gtctatgaac gtagagattt aagtgggaat atgttttgga cgcgggttca actcccgcca   360
gctccacca                                                          369
```

<210> SEQ ID NO 28
<211> LENGTH: 353
<212> TYPE: DNA
<213> ORGANISM: Heliobacillus mobilis

<400> SEQUENCE: 28

```
ggggctgatt ctggattcga cggggaacgt gtttgcttgg gatgcgagcc gggttgccgc    60
caggaccgta aaagggcgg aaggctttaa ttgccgaaga taactacgct ttagctgctt   120
aattgcagtc taacctcttc tcctctgtgc tctcggtgag gatgtaaggg gtcatttaag   180
agagctggct tcgaccaatt ctcggaggtc caagcgagat ttatcgagat agcctgacca   240
acgctctgtc tgccgtgcgg aaggaaggcg aaatctaaaa cgacagacta cgctcgtagt   300
gtcctttgtg ggcatttctt cggacgcggg ttcaactccc gccagctcca cca         353
```

<210> SEQ ID NO 29
<211> LENGTH: 353
<212> TYPE: DNA
<213> ORGANISM: Heliospirillum gestii

<400> SEQUENCE: 29

```
ggggctgatt ctggattcga cggggaacgt gtttgcttag gacgcgagcc gggttgccgc    60
caggaccgta aaagggcgg aaggctttaa ttgccgaaga taactacgct ttagctgctt   120
aattgcagtc taacctcttc tcctctgtgc tctcggtgag gatgtaaggg gtcatttaag   180
agagctggct cgaaccaatt ctcggaggtt cgggtaagac ttatcgagat agcctgacca   240
acgctctgtc tgccgtgcgg aaggatggcg aaatctaaaa cgacagaata cgctcgtagt   300
gtcctttgtg ggcatttctt cggacgcggg ttcaactccc gccagctcca cca         353
```

<210> SEQ ID NO 30
<211> LENGTH: 368
<212> TYPE: DNA
<213> ORGANISM: Lactobacillus acidophilus

<400> SEQUENCE: 30

```
ggggctgatt ctggattcga caggcgtaga cccgcattga ctgcggttcg taggttacgt    60
ctacgtaaaa acgttacagt taaatataac tgcaaataac aaaaattctt acgcattagc   120
tgcttaattt agcgcatgcg ttgctctttg tcggtttact cgtggctgac actgagtatc   180
aacttagcga gttacgttta actacctcac ctgaatagtt gaaagagtc ttagcaggtt   240
agctagtcca tactagccct gttatatggc gttttggact agtgaagttc aagtaatata   300
```

```
actatgatcg tagaggtcag tgacgagatg cgtttggaca gcgggttcaa ctcccgccag    360
ctccacca                                                              368
```

<210> SEQ ID NO 31
<211> LENGTH: 360
<212> TYPE: DNA
<213> ORGANISM: Staphylococcus epidermidis

<400> SEQUENCE: 31

```
ggggctgatt ctgcattcga caggggtccc cgagcttatt aagcgtgtgg agggttggct     60
ccgtcatcaa cacatttcgg ttaaatataa ctgacaaatc aaacaataat ttcgcagtag    120
ctgcgtaata gccactgcat cgcctaacag catctcctac gtgctgttaa cgcgattcaa    180
ccctagtagg atatgctaaa cactgccgct tgaagtctgt ttagatgaaa tataatcaag    240
ctagtatcat gttggttgtt tattgcttag catgatgcga aaattatcaa taaactacac    300
acgtagaaag atttgtatca ggacctctgg acgcgggttc aactcccgcc agctccacca    360
```

<210> SEQ ID NO 32
<211> LENGTH: 368
<212> TYPE: DNA
<213> ORGANISM: Streptococcus faecium

<400> SEQUENCE: 32

```
ggggctgatt ctggattcga caggcacagt ttgagcttga attgcgtttc gtaggttacg     60
tctacgttaa aacgttacag ttaaatataa ctgctaaaaa cgaaaacaac tcttacgctt    120
tagctgccta aaaacagtta gcgtagatcc tctcggcatc gcccatgtgc tcgagtaagg    180
gtctcaaatt tagtgggata cgtgacaact ttccgtctgt aagttgttaa agagatcatc    240
agactagcga tacagaatgc ctgtcactcg gcaagctgta aagcgaaacc acaaatgagt    300
tgactatgaa cgtagatttt taagtggcga tgtgtttgga cgcgggttca actcccgccg    360
ttccacca                                                              368
```

<210> SEQ ID NO 33
<211> LENGTH: 328
<212> TYPE: DNA
<213> ORGANISM: Thermoanaerobacterium saccharolyticum

<400> SEQUENCE: 33

```
ggggtagtag aggtaaaagt agcgagccga ggttccatct gctcgtaaaa cggtggactt     60
aaatataaac gcaaacgata atttagctta cgctgcttaa ttacaagcag ccgttcaacc    120
tttgattccc acatcaaagg attgggcgtc gatttagtgg ggaactgatt tatcaaagct    180
ttgagataaa tcggatttta tgaagctacc aaagcagtta tcctgtcact gggagaactg    240
cagagggaat gtcaaaacag tgactgcgct cggagaagct tttactgtga caccttcgga    300
ccggggttca actcccgcca gcccacca                                        328
```

<210> SEQ ID NO 34
<211> LENGTH: 379
<212> TYPE: DNA
<213> ORGANISM: Mycoplasma fermentans

<400> SEQUENCE: 34

```
ggggctgatt ctggattcga catgcattgg gtgatactaa tatcagtagt ttggcagact     60
ataatgcatc taggctttat aatcgcagaa gataaaaaag cagaagaagt taatatttct    120
```

```
tcacttatga ttgcacaaaa aatgcaatca caatcaaacc ttgctttcgc ttagttaaaa    180
gtgacaagtg gttttaaagt tgacatttc ctatatattt taaaatcggc ttttaaggag    240
aacaggagtc tgaaagggtt ccaaaaatct atattgtttg catttcggta gtatagatta    300
attagaaatg ataaactgta aaagtattg gtattgactt ggtgtgtgga ctcgggttca    360
actcccgcca gctccacca                                                 379
```

<210> SEQ ID NO 35
<211> LENGTH: 373
<212> TYPE: DNA
<213> ORGANISM: Mycoplasma hyorhinis

<400> SEQUENCE: 35

```
ggggctgatt ctggattcga catacataaa aggatataaa ttgcagtggt cttgtaaacc    60
ataagacaat ttctttacta agcggaaaag aaaacaaaaa agaagattat tcattattaa   120
tgaatgcttc aactcaatca aatctagctt ttgcatttta aaaaactagt agaccaattt   180
gcttctcacg aattgtaatc tttatattag agaatagtta aaaatctgat cacttttaa   240 tgaatttata gatcacaggc tttttaatc tttttgttat tttagataaa gagtcttctt   300
aaaaataact aaactgtagg aatttatatt taattatgcg tggacccggg ttcaactccc   360
gccagctcca cca                                                      373
```

<210> SEQ ID NO 36
<211> LENGTH: 399
<212> TYPE: DNA
<213> ORGANISM: Mycoplasma pirum

<400> SEQUENCE: 36

```
ggggagtcat ggttttgaca tgaatgatgg acccatagag gcagtggggt atgcccctta    60
tagctcaagg tttaaattaa ccgacaaaac tgacgaaaac gttgccgttg atacaaattt   120
attaatcaac caacaagctc aatttaacta cgcatttgca tagtataaaa aaataaattg   180
tgctactcat tgtaattagg ttactaaatt actttgtttt atatagtcct gtaactagtt   240
ctagtgatgt ctataaacta gaatgagatt tatagactta tttgttggcg gttgtgccat   300
agcctaaatc aacaaagaca atttatttat ggtactaaac tgtagattct atgatgaaat   360
tatttgtgga aacgggttcg attcccgcca tctccacca                          399
```

<210> SEQ ID NO 37
<211> LENGTH: 385
<212> TYPE: DNA
<213> ORGANISM: Mycoplasma salivarium

<400> SEQUENCE: 37

```
ggggctgatt ctggattcga caggcattcg attcattatg ttgcagtggt ttgcaaacca    60
taaggcacta ggctttttta aacgcaaaag accaaaaaac agaagatcaa gcagttgatc   120
tagcatttat gaataattca caaatgcaat caaatctagt tttcgcttag taaaattagt   180
caatttatta tggtgctcaa cataataaat ggtagtatga gcttaatatc atatgatttt   240
agttaatatg ataggatttg taactaaact atgttataga aatttgtaaa ttatatatat   300
gacataggaa atttaattta ctaaactgta gatgcataat gttgaagatg tgtggaccgg   360
ggttcaactc ccgccagctc cacca                                         385
```

<210> SEQ ID NO 38
<211> LENGTH: 362

```
<212> TYPE: DNA
<213> ORGANISM: Herpetosiphon aurantiacus

<400> SEQUENCE: 38 ggggggcggaa aggattcgac ggggagggcc aatcgtaagt ggcaagccga gacgctgagc    60
ctcgttaaat cggcaacgcc attaactggc aaaaacactt tccgcgctcc tgtagcgctt   120
gctgcctaat taaggcaaca cgtctctact agcctcagcc cgatgggctt gtagcggcga   180
cacttagtcg ggtcgctccc ctagttatgt ctgtgggcta ggggctaaga ttaacaggct   240
ggtcgtggcc cgctttgtct atcggtggt gcaccgataa gatttaatca atagactacg    300
cttgtagatg cttgcggttt aactttttgg acgcgggttc gattcccgcc gcctcaccac   360
ca                                                                  362

<210> SEQ ID NO 39
<211> LENGTH: 355
<212> TYPE: DNA
<213> ORGANISM: Thermomicrobium roseum

<400> SEQUENCE: 39
ggggctgatt ctggattcga cagggccgta ggtgcgagga ttgcaggtcg aggtcgccca    60
cgaactcgta aaaggggca gccaagtaac tggcgagcgc gaactcgctc tggctgcgta   120
attcacgcag ccacgtctgc ccggacccctt ccctggtggg ttcggagcgg gcgccgcaag  180
accggggtgc ccctggccca agcgccggtg cgggccaggt caagcgtgat ccggctcggc   240
tgaccgggat cctgtcggtg ggagcctggc agcgacagta gaacaccgac taagcctgta   300
gcatatcctc ggctgaacgc tctggacgcg ggttcaactc ccgccagctc cacca        355

<210> SEQ ID NO 40
<211> LENGTH: 405
<212> TYPE: DNA
<213> ORGANISM: Chlorobium limicola

<400> SEQUENCE: 40
ggggctgatt ctggattcga caggatacgt gtgagatgtc gttgcactcc gagtttcagc    60
atggacggac tcgttaaaca agtctatgta ccattagatg cagacgatta ttcgtatgca   120
atggctgcct gattagcaca agttaactca gacgccatcg tcctgcggtg aatgcgctta   180
ctctgaagcc gccggatggc ataacccgcg cttgagccta cgggttcgcg caagtaagct   240
ccgtacattc atgcccgagg ggctgtgcgg gtaatttctc gggataaggg gacgaacgct   300
gctggcggtg taatcggccc acgaaaaccc aatcaccaga gatgagtgtg gtgactgcat   360
cgagcagtgt tttggacgcg ggttcaactc ccgccagctc cacca                   405

<210> SEQ ID NO 41
<211> LENGTH: 362
<212> TYPE: DNA
<213> ORGANISM: Pirellula staleyi

<400> SEQUENCE: 41
ggggctgatt ctggattcga ccggatagcc tgaagcgaat acggcgtgcc gtggttgatc    60
agatggccac gtaaaaagct gatcacaaac ttaactgccg agagcaatct cgcacttgct   120
gcctaactaa acggtagctt ccgactgagg gctttagccg gagaggccca aaagttggtc   180
accaaatccg gaccgcctcg tgccatgatc gaaacgcacg aggtcaaaaa agtttcgatc   240
tagtgcaggg tgtagccagc agctaggcga caaactgtgc aaaaatcaaa ttttctgcta   300
```

```
cgcacgtaga tgtgttcgtg aaaatgtctc gggacggggg ttcaactccc gccactccac    360
ca                                                                   362

<210> SEQ ID NO 42
<211> LENGTH: 346
<212> TYPE: DNA
<213> ORGANISM: Planctomyces limnophilus
<220> FEATURE:
<221> NAME/KEY: misc_feature
<222> LOCATION: (1)..(346)
<223> OTHER INFORMATION: n is an unknown base

<400> SEQUENCE: 42
ggggctgatt ctggattcga caacctctca agaggagcgt ggccactatg ggactcgatt     60
atgttgaatt cgtcatggat cttgaagaga ccttcgacat caaactggat gacaaacatt    120
tttcagcagt caaaacacca cgcgatttgg caatcattat tcgggatcaa ttagctgctg    180
aaggcagaat ctgggatgaa tcgaatgctt ttcgcaaaat ctcgaatttg aattggacga    240
tgttgcccga gttccggatg tggactcaaa tcaaaagctc tctaccagtt tcttttcacc    300
gactgcgtcc cagcacccgt ctcgttcaac tcccgccant ccacca                   346

<210> SEQ ID NO 43
<211> LENGTH: 362
<212> TYPE: DNA
<213> ORGANISM: Planctomyces maris

<400> SEQUENCE: 43
ggggctgatt ctggattcga ctggttcacc gtatgttaag gtggcggtgc cgtggttgat     60
cagttggcca cgtaaaaagc tgatcacaat ctaattgcaa acaagcaatt ttcaatggct    120
gcttaataaa agcaaccccg gcttaggaat ctctgtctga ggagtccgac agctggtcac    180
aaaatcagac tggtatcaga tcaatgtccg ctccgtctga tacgagattc gtggtggact    240
ggtttccaac aggctctgtt tatcgtgccc gaagaaacga gactcaaacg ataaaatatg    300
caccgtagag gctttagctg agggttcaca ggacgcgggt tcaactcccg ccagctccac    360
ca                                                                   362

<210> SEQ ID NO 44
<211> LENGTH: 360
<212> TYPE: DNA
<213> ORGANISM: Alcaligenes eutrophus

<400> SEQUENCE: 44
ggggttgatt ctggattcga cgtgggttac aaagcagtgg agggcatacc gaggacccgt     60
cacctcgtta atcaatggga atgcaataac tgctaacgac gaacgttacg cactggccgc    120
ttaattgcgg ccgtcctcgc actggctcgc tgacgggcta gggtcgcaag accacgcgag    180
gtcatttacg tcagataagc tccggaaggg tcacgaagcc ggggacgaaa acctagtgac    240
tcgccgtcgt agagcgtgtt cgtccgcgat gcgccggtta aatcaaatga cagaactaag    300
tatgtagaac tctctgtgga gggcttacgg acgcgggttc aactcccgcc agctccacca    360

<210> SEQ ID NO 45
<211> LENGTH: 362
<212> TYPE: DNA
<213> ORGANISM: Alcaligenes faecalis

<400> SEQUENCE: 45
gggggcggaa aggattcgac gggggtcaag aagcagcaca gggcgtgtcg agcaccagta     60
```

-continued

```
cgctcgtaaa tccactggaa aactataaac gccaacgacg agcgtttcgc tctagccgct    120
taaggctggg ccactgcact aatttgtctt tgggttaggt agggcaaccct acagcagtgt   180 tatttacaaa gaatcgaatc ggtctgcgcc acgaagtccg gttctaaaac ttagtggatc    240
gccaaggaaa ggcctgtcaa ttggcatagt ccaaggttaa aacttaaaat taattgacta    300
cacatgtaga actgtctgtg gacggcttgc ggacggggggt tcgattcccg ccgcctccac   360
ca                                                                   362

<210> SEQ ID NO 46
<211> LENGTH: 366
<212> TYPE: DNA
<213> ORGANISM: Chromobacterium violaceum

<400> SEQUENCE: 46
ggggctgatt ctggattcga cgggggttgc gaagcagatg agggcatacc gggatttcag     60
tcaccccgta aaacgctgaa tttatatagt cgcaaacgac gaaacttacg ctctggcagc   120
ctaacggccg gccagacact acaacggttc gcagatgggc cggggcgtc aaaaccctgt    180 agtgtcactc tacatctgct agtgctgttc cgggttactt ggttcagtgc gaaataatag   240
gtaactcgcc aaagtccagc ctgtccgtcg gcgtggcaga ggttaaatcc aaatgacacg    300
actaagtatg tagaactcac tgtagaggac tttcggacgc gggttcaact cccgccagct   360
ccacca                                                               366

<210> SEQ ID NO 47
<211> LENGTH: 378
<212> TYPE: DNA
<213> ORGANISM: Hydrogenophaga palleroni

<400> SEQUENCE: 47
ggggctgatt ctggattcga cgtgggttcg gacgcgcagc agggcatgtc gaggttctgt     60
cacctcgtaa atcagcagaa aaaaaccaac tgcaaacgac gaacgtttcg cactcgccgc   120
ttaaacaccg gtgagccttg caacagcagg ccgatgggct gggcaagggg gtcgcaagac   180
ctcccggctg caaggtaatt tacatcggct ggttctgcgt cgggcacctt ggcgcaggat   240
gagattcaag gatgctggct tcccgtttag cgtgccactg cgcgactcgg gcggcgagac   300
ccaaatcaga cggctacaca tgtagaactg ctcgaaaaag gcttgcggac gggggttcaa   360
ctcccgccag ctccacca                                                  378

<210> SEQ ID NO 48
<211> LENGTH: 365
<212> TYPE: DNA
<213> ORGANISM: Methylobacillus glycogenes

<400> SEQUENCE: 48
gggggcggaa aggattcgac gggggttgca aagcagcgca gggcataccg aggcctagtc     60
acctcgtaaa taaactagaa caagtatagt cgcaaacgac gaaacttacg ctctagccgc   120
ttaatcccgg ctggacgctg caccgaaggg cctctcggtc gggtggggta acccacagca   180
gcgtcattaa gagaggatcg tgcgatattg ggttacttaa tatcgtatta aatccaaggt   240
aactcgcctg ctgtttgctt gctcgttggt gagcatcagg ttaaatcaaa caacacagct   300
aagtatgtag aactgtctgt ggagggcttg cggacggggg ttcgattccc gccgcctcac   360
cacca                                                                365
```

<210> SEQ ID NO 49
<211> LENGTH: 362
<212> TYPE: DNA
<213> ORGANISM: Nitrosomonas cryotolerans

<400> SEQUENCE: 49

```
ggggctgatt ctggattcga cgtgggttgc aaagcagcgc agggcatacc gaggaccaga      60
atacctcgta aatacatctg gaaaaaaata gtcgcaaacg acgaaaacta cgctttagcc     120
gcttaatacg gctagcctct gcaccgatgg gccttaacgt cgggtctggc aacagacagc     180
agagtcatta gcaaggatcg cgttctgtag ggtcacttta cagaacgtta aacaataggt     240
gactcgcctg ccatcagccc gccagctggc ggttgtcagg ttaaattaaa gagcatggct     300
aagtatgtag aactgtctgt agaggacttg cggacgcggg ttcaactccc gccagtccac     360
ca                                                                    362
```

<210> SEQ ID NO 50
<211> LENGTH: 378
<212> TYPE: DNA
<213> ORGANISM: Pseudomonas testosteroni

<400> SEQUENCE: 50

```
ggggctgatt ctggattcga cgtgggttcg ggaccggtgc ggtgcatgtc gagcttgagt      60
gacgctcgta aatctccatt caaaaaacta actgcaaacg acgaacgttt cgcactcgcc     120
gcttaatccg gtgagccttg caacagcacg ctagtgggct gggcaagggg gtagcaatac     180
ctcccggctg caagggaatt ttcattagct ggctggatac cgggcttctt ggtatttggc     240
gagattttag gaagctggct acccaagcag cgtgtgcctg cggggtttgg gtggcgagat     300
ttaaaacaga gcactaaaca tgtagatctg tccggcgaag gcttacggac gcgggttcaa     360
ctcccgccag ctccacca                                                   378
```

<210> SEQ ID NO 51
<211> LENGTH: 360
<212> TYPE: DNA
<213> ORGANISM: Ralstonia pickettii

<400> SEQUENCE: 51

```
gggggcggaa aggattcgac gggggttgcg aagcagcgga gggcataccg aggaccgtc       60
acctcgttaa tcaatgggaa tgcaataact gctaacgacg aacgttacgc actggcagcc    120
taagggccgc cgtcctcgca ctggctcgct gacgggctag ggtcgcaaga ccagcgaggt    180
catttacgtc agataagctt taggtgagtc acgggcctag agacgaaaac ttagtgaatc    240
gccgtcgtag agcgtgttcg tccgcgatgc ggcggttaaa tcaaatgaca gaactaagta    300
tgtagaactc tctgtggagg gcttgcggac gcgggttcga ttcccgccgc ctcaccacca    360
```

<210> SEQ ID NO 52
<211> LENGTH: 386
<212> TYPE: DNA
<213> ORGANISM: Variovorax paradoxus

<400> SEQUENCE: 52

```
ggggctgatt ctggattcga cgtgggttcg gagtcgcagc ggggcatgtc gagctgaatg      60
cgctcgtaaa acagattcaa acaaactaac tgcaaacgac gaacgtttcg cactcgctgc    120
ttaattgcca gtgagccttg caacagttgg ccgatgggct gggcaagggg gtctggagca    180
atcctgacct cccggctgca aggataacta catgggctgg ctccgatccg ggtaccttgg    240
```

```
gtcggggcga gaaaataggg tactggcgtc cggtttagcg tgtgactgcg cgactccgga      300
agcgagactc aaaacagatc actaaacatg tagaactgcg cgatgaaggc ttgcggacgg      360
gggttcaact cccgccagct ccacca                                           386
```

```
<210> SEQ ID NO 53
<211> LENGTH: 346
<212> TYPE: DNA
<213> ORGANISM: Bdellovibrio bacteriovirus

<400> SEQUENCE: 53
gggggcggaa aggattcgac gggggtgctg aagcataagg agcataccgg ggcggatgag      60
gacctcgtta aaaacgtcca ctttgtaatt ggcaacgatt acgcacttgc agcttaatta     120
agcagcacga tcaaccttgt ggtggttccg cacttggatt gatcgtcatt tagggacctc     180
ggcgtgttgg gttttctcca gcagacatgc ttaaatttac tggggagag gtcttaggga      240 ttttgtctgt ggaagcccga ggaccaatct aaaacactga ctaagtatgt agcgccttat     300
cgtggatcat ttgcggacgg gggttcgatt cccgccgcct ccacca                    346
```

```
<210> SEQ ID NO 54
<211> LENGTH: 366
<212> TYPE: DNA
<213> ORGANISM: Myxococcus xanthus

<400> SEQUENCE: 54
gggggcggaa aggattcgac gggggcattg aagttcgaga cgcgtgccga gcttgtcagg      60
tagctcgtaa attcaacccg gcaaagacac aaaagccaac gacaacgttg agctcgcgct     120
ggctgcctaa aaacagccca tagtgcgcgg tccccccgcc ctcggcctgt ggggttggga     180
cagaccgtca taatgcaggc tggctgccga gggtgcctgg acccgaggtg gcgagatctt     240
cccaggaccg gctctgagta tcccgtccgt gggagcctca gggacgtagc aaatcgcgga     300
ctacgcacgt agggtcgaag agcggacggc tttcggacgc gggttcgatt cccgccgcct     360
ccacca                                                                366
```

```
<210> SEQ ID NO 55
<211> LENGTH: 380
<212> TYPE: DNA
<213> ORGANISM: Sulfurospirillum deleyianum

<400> SEQUENCE: 55
ggggctgatt ctggattcga caggagtagt tttagcttat ggctgcatgt cgggagtgag     60
ggtcttccgt tacacaacct tcaaacaata actgctaaca acagtaacta tcgtcctgct    120
tacgcgctag ctgcgtaagt ttaacaaata atggactgct ctcccctttg atgctatctt    180
aggaggtctt ggagagtatc atagatttga tagctatatt acatgaacgc ctttacatgt    240
aatgaagtta aaggctcgtt ttgcgtagtt ttctgattgt tgtacgaagc aaaattaaac    300
actatcaaca atatctaagc atgtagacgt cataggtggc tattttttgga ctgcgggttc    360 aactcccgcc agctccacca                                                 380
```

```
<210> SEQ ID NO 56
<211> LENGTH: 359
<212> TYPE: DNA
<213> ORGANISM: Chromatium vinosum

<400> SEQUENCE: 56
```

-continued

```
ggggctgatt ctggattcga cgtgggtcgc gaaacctaag gtgcatgccg aggtgcggtt     60
gacctcgtaa aaccctccgc aaacttatag ttgccaacga cgacaactac gctctcgctg    120
cttaatccca gcgggcctct gaccgtcact tgcctgtggg cggcggattc caggggtaac    180
ctcacacagg atcgtggtga cgggagtccg gacctgatcc actaaaacct aacggaatcg    240
ccgactgatc gccctgccct tcgggcggca gaaggctaaa aacaatagag tgggctaagc    300
atgtaggacc gagggcagag ggcttgcgga cgcgggttca actcccgcca gctccacca     359
```

<210> SEQ ID NO 57
<211> LENGTH: 395
<212> TYPE: DNA
<213> ORGANISM: Pseudomonas fluorescens

<400> SEQUENCE: 57

```
ggggctgatt ctggattcga cgccggttgc gaacctttag gtgcatgccg agttggtaac     60
agaactcgta aatccactgt tgcaactttc tatagttgcc aatgacgaaa cctacgggga    120
atacgctctc gctgcgtaag cagccttagc ccttccctcc tggtaccttc gggtccagca    180
atcatcaggg gatgtctgta aacccaaagt gattgtcata tagaacagaa tcgccgtgca    240
gtacgttgtg gacgaagcgg ctaaaactta cacaactcgc ccaaagcacc ctgcccgtcg    300
ggtcgctgag ggttaactta atagacacgg ctacgcatgt agtaccgaca gcagagtact    360
ggcggacgcg ggttcaactc ccgccagctc cacca                               395
```

<210> SEQ ID NO 58
<211> LENGTH: 362
<212> TYPE: DNA
<213> ORGANISM: Borrelia afzelii

<400> SEQUENCE: 58

```
ggggctgatt ctggattcga ctgaaaatgc taatattgta agttgcaagc agagggaatc     60
tcttaaaact tctaaaataa atgcaaaaaa taataacttt acaagttcaa accttgtaat    120
ggctgcttaa gttagcagag agttttgttg aatttggctt tgagattcac ttatactctt    180
ttagacatcg aagcttgctt aaaaatgttt tcaagttgat ttttagggac ttttatactt    240
gagagcaatt tggcggtttg ctagtatttc caaaccatat tgcttagtaa aatactagat    300
aagcttgtag aagcttatag tattgttttt aggacgcggg ttcaactccc gccagtccac    360
ca                                                                   362
```

<210> SEQ ID NO 59
<211> LENGTH: 363
<212> TYPE: DNA
<213> ORGANISM: Borrelia crocidurae

<400> SEQUENCE: 59

```
ggggctgatt ctggattcga ctaagaactt tagtagcata aatggcaagc agagtgaatc     60
tcttaaaact tctttaataa atgcaaaaaa taataacttt acaagttcag atcttgtaat    120
ggctgcttaa tttagcagag agttttgttg gattttgctt tgaggttcaa cttatactct    180
ttaagacatc aaagtatgcc taaaaatgtt tcaagttgat ttttagggac ctttaaactt    240
gagagtaatt tggtggtttg cttgttttcc aagccttatt gctttttcta aaaattagct    300
aagcttgtag atatttatga tattattttt aggacgcggg ttcaactccc gccagttcca    360
cca                                                                  363
```

<210> SEQ ID NO 60
<211> LENGTH: 365
<212> TYPE: DNA
<213> ORGANISM: Borrelia hermsii

<400> SEQUENCE: 60

| | | |
|---|---|---|
| ggggctgatt ctggattcga ctaaaaactt tagtagcata aattgcaagc agagggaatc | 60 |
| tcttaaaact tctttaataa atgcaagaaa taataacttt acaagttcaa atcttgtaat | 120 |
| ggctgcttaa attagcagag agttctgctg gattttgctt tgaggttcag cttatactct | 180 |
| tttaagacat caaagcttgc ttaaaaatat ttcaagttga tttttaggga cttttaaatt | 240 |
| tgagagtaat ttggcggttt gctagttttt ccaaacctta ttacttaaag aaaacactag | 300 |
| ctaagcttgt agatatttat gatattattt ttaggacgcg ggttcaactc ccgccagctc | 360 |
| cacca | 365 |

<210> SEQ ID NO 61
<211> LENGTH: 363
<212> TYPE: DNA
<213> ORGANISM: Borrelia garinii

<400> SEQUENCE: 61

| | | |
|---|---|---|
| ggggctgatt ctggattcga ctgaaaatgc gaatattgta agttgcaggc agagggaatc | 60 |
| tcttaaaact tctaaaataa atgcaaaaaa taataacttt acaagctcaa accttgtaat | 120 |
| ggctgcttaa gttagcaggg agtttcgttg aatttggctt tgaggttcac ttatactctt | 180 |
| ttcgatatcg aagcttgctt aaaaatgttt tcaagttaat ttttagggac ttttgtactt | 240 |
| gagagcaatt tggcggtttg ctagtatttc caaaccatat tgcttaagta aaatgctaga | 300 |
| taagcttgta gaagcttata atattgtttt taggacgcgg gttcaactcc cgccagtcca | 360 |
| cca | 363 |

<210> SEQ ID NO 62
<211> LENGTH: 357
<212> TYPE: DNA
<213> ORGANISM: Thermodesulfobacterium commune

<400> SEQUENCE: 62

| | | |
|---|---|---|
| ggggggcggaa aggattcgac ggggataggt aggattaaac agcaggccgt ggtcgcaccc | 60 |
| aaccacgtta aatagggtgc aaaaacacaa ctgccaacga atacgcctac gctttggcag | 120 |
| cctaagcgtg ctgccacgca cctttagacc ttgcctgtgg gtctaaaggt gtgtgaccta | 180 |
| acaggctttg ggaggcttaa tcggtggggt taagcctccc gagattacat cccacctggt | 240 |
| agggttgctt ggtgcctgtg acaagcaccc tacgagattt tcccacaggc taagcctgta | 300 |
| gcggtttaat ctgaactatc tccggacgcg ggttcgattc ccgccgcctc cccacca | 357 |

<210> SEQ ID NO 63
<211> LENGTH: 358
<212> TYPE: DNA
<213> ORGANISM: Thermotoga neapolitana
<220> FEATURE:
<221> NAME/KEY: misc_feature
<222> LOCATION: (1)..(358)
<223> OTHER INFORMATION: n is an unknown base

<400> SEQUENCE: 63

| | | |
|---|---|---|
| ggggggcggaa aggattcgac ggggatggag tccctgggga agcgagccga ggtccccacc | 60 |
| tcctcgtaaa aaaggtggga acacgaataa gtgccaacga acctgttgct gttgccgcct | 120 |

```
aatagatagg cggccgtcct ctccggagtt ggctgggctc cggaagaggg cgtgagggat    180
ccagcctacc gatctgggct ccgccttccg gcccggatcg ggaaggttca ggaaggctgt    240
gggaagcgac accctgcccg tgggggtcc ttcccgagac acgaaacacg ggctgcgctc    300
ggagaagccc aggggcctcc atcttcngac gcgggttcga ttcccgccac ctccacca     358
```

<210> SEQ ID NO 64
<211> LENGTH: 347
<212> TYPE: DNA
<213> ORGANISM: Deinococcus proteolyticus
<400> SEQUENCE: 64

```
gggggcggaa aggattcgac gggggaacgg aaagcgctgc tgcgtgccga ggagccgttg     60
gcctcgtaaa caaacggcaa agccattaac tggcgaaaat aactacgctc tcgctgctta    120
agtgagacag tgaccacgta gccccgcctt tggcgacgtg tgaactgaga caaaagaagg    180
ctagcttagg tgaggttcca tagccaaaag tgaaaccaaa tggaaataag gcggacggca    240
gcctgtttgc tggcagccca ggcccgacaa tttaagagca gactacgcac gtagatgcac    300
gctggatgga cctttggacg cgggttcgat tcccgccagc tccacca                  347
```

<210> SEQ ID NO 65
<211> LENGTH: 352
<212> TYPE: DNA
<213> ORGANISM: Prosthecobacter fusiformis
<400> SEQUENCE: 65

```
ggggctgatt ctggattcga cggggagtac aaggatcaaa agctgcaagc cgaggtgccg     60
ttacctcgta aaacaacggc aaaaaagaag tgccaacaca aatttagcat tagctgctta    120
atttagcagc tacgctcttc taacccgggc tggcagggtt agaagggtgt cataatgagc    180
cagctgcccc ttccgactcc cctaaggaag ggaaagatgt aggggatagg tgcttacaga    240
atcctgcggg agggagtctg taagtgccga aaagttaaaa ctcccgctaa gcttgtagag    300
gcttttgatt cttgctctct ggacgcgggt tcaactcccg ccagctccac ca            352
```

<210> SEQ ID NO 66
<211> LENGTH: 329
<212> TYPE: DNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base
<400> SEQUENCE: 66

```
gggnnnnatt tggaattcgc cgaatgctag aagtggaggc tgcatgccgc ggatgattcg     60
ttggccgctt taccaattcg gatcaaacaa ctaaatgcgg actctaacga gcttgccctc    120
gccgcttaat tgacggtgac gttcctccag tgaagtctgt gaattggagg agcgactact    180
tacaggctgg ccaaaagagc gggcgaccgg ccccaaggcg agatctacag gccgctggat    240
ggacggcatc ctggcagtag gaggctggac atcgagatca aatnattgcc tgagcatgga    300
gacgctttca taaaggngtt cggacaggg                                      329
```

<210> SEQ ID NO 67
<211> LENGTH: 318
<212> TYPE: RNA
<213> ORGANISM: Thermoanaerobacterium saccharolyticum
<400> SEQUENCE: 67

```
cgggggguagu agagguaaaa guagcgagcc gagguuccau cugcucguaa aacgguggac    60
uuaaauauaa acgcaaacga uaauuuagcu acgcugcuu aauuacaagc agccguucaa    120
ccuuugauuc ccacaucaaa ggauggggcg ucgauuuagu ggggaacuga uuuaucaaag   180
cuuugagaua aaucggauuu uaugaagcua ccaaagcagu uaccugucu cugggagaac    240 ugcagaggga augucaaaac agugacgcg cucggagaag cuuuuacugu gacaccuucg    300 gaccggggu caacuccc                                                  318
```

<210> SEQ ID NO 68
<211> LENGTH: 187
<212> TYPE: RNA
<213> ORGANISM: Clostridium acetobutylicum

<400> SEQUENCE: 68

```
aaucuggcgu cgagagcggg gaaacgagcc uuacaaagcu uugaguaagg aacggaauuu    60
augaagcuac ugaagugaaa agcuuguuug uaggcguuuc auggagggaa uguuaaaaua   120
caaacugcac ucggagaugc uuaaaugaaa ccauuucgg acaggggguuc gauuccccuc   180 gccucca                                                             187
```

<210> SEQ ID NO 69
<211> LENGTH: 335
<212> TYPE: RNA
<213> ORGANISM: Clostridium stercorarium

<400> SEQUENCE: 69

```
cggggguuau gaagcaagag uagcggguag aggauucucg uuggccucuu uaaaaaacga    60
gagcuaaaaa uaaacgcaaa caacgauaac uacgcuuuag cugcugcgua aguaacacgc   120
agcccgucgg ccccggggu ccugcgccuc gggauaccgg cgucaucaag gcagggaacc   180
agccggauca ggcuucaggu ccgguggau uuaaugaagc uaccgacuua uaagccugu    240 cucugggcgu uauaagaagg gaaugucaaa acagagacac caaugcaccc ggagaagcuc   300
uuguggauau gguuccggac acgaguucga uuccc                              335
```

<210> SEQ ID NO 70
<211> LENGTH: 336
<212> TYPE: RNA
<213> ORGANISM: Clostridium perfringens

<400> SEQUENCE: 70

```
cgggggguaag augggguuga uaagcgaguc gagggaagca ugugccucg auaauaaagu    60 augcauuaaa gauaaacgca gaagauaauu uugcauuagc agcuuaauuu agcgcugcuc   120
auccuuccuc aauugcccac gguugagagu aagggguguca uuuaaaagug gggaaccgag   180
ccuagcaaag cuuugagcua ggaacggaau uuaugaagcu agaggaagu uugucugug    240 acguucucug agggaauuuu aaaacacaag acacuaaaau cuaguacacu cguagaaagu   300
cuuacugguc ugcuuucgga cacggguuca acuccc                             336
```

<210> SEQ ID NO 71
<211> LENGTH: 305
<212> TYPE: RNA
<213> ORGANISM: Clostridium lentocellum

<400> SEQUENCE: 71

```
cgggggucac aucuacuggg gcagccauuc guagaacgcc ggagucuacg uuaaaagcug    60
```

```
gcacuuaaag uaaacgcuga agauaauuua gcaaucgcug ccuaauuaag gcgcaguccu    120
ccuaggucuu ccgcagccua gaucagggcu ucgacucgcg gauccuucac cuggcaaagc    180
uuugagccaa cgugaacacu augaagcuag ccugucuuug ggcgcuagau ggagggaaug    240
ucaaaacaaa gaauaugaug guagagacca cgcuauaugg gcuucggac  aggggguucga   300 uuccc                                                                305

<210> SEQ ID NO 72
<211> LENGTH: 319
<212> TYPE: RNA
<213> ORGANISM: Heliobacillus mobilis

<400> SEQUENCE: 72
cggggaacgu guuugcuugg gaugcgagcc ggguugccgc caggaccgua aaagggcgg      60 aaggcuuuaa uugccgaaga uaacuacgcu uuagcugcuu uauugcaguc uaaccucuuc    120
uccucugugc ucucggugag gauguaaggg gucauuaaag agagcuggcu ucgaccaauu    180
cucggagguc caagcgagau uuaucgagau agccugacca acgcucuguc ugccgugcgg    240
aaggaaggcg aaaucuaaaa cgacagauac gcucguagug uccuuugugg gcauucuuc    300 ggacgcgggu ucaacuccc                                                 319

<210> SEQ ID NO 73
<211> LENGTH: 321
<212> TYPE: RNA
<213> ORGANISM: Heliospirillum gestii

<400> SEQUENCE: 73
cggggaacgu guuugcuuag gacgcgagcc ggguugccgc caggaccgua aaagggcgg      60 aaggcuuuaa uugccgaaga uaacuacgcu uuagcugcuu aauugcaguc uaaccucuuc    120
uccucugugc ucucggugag gauguaaggg gucauuaaag agagcuggcu cgaaccaauu    180
cucggagguu cggguaagac uuaucgagau cagccugacc aacgcucugu cugccgugcg    240
gaaggauggc gaaaucuaaa acgacagaau acgcucguag uguccuuugu gggcauuucu    300
ucggacgcgg guucaacucc c                                              321

<210> SEQ ID NO 74
<211> LENGTH: 325
<212> TYPE: RNA
<213> ORGANISM: Brevibacillus brevis

<400> SEQUENCE: 74
cggggauggu agagcaugag aagcgagccg ggggguugcg gaccucguca ccaacgcaaa     60
cgccauuaac uggcaacaaa caacuuucuc ucgcugcuua auaaccagug aggcucuccc    120
acugcaucgg cccgugugcc guggauaggg cucaacuuua acgggcuacg ccggaggcuu    180
ccgccuggag ccaaaggaag aagaccaauc aggcuaggu  ccaggucagc gcgucaccuc    240
gcgaaucugu caccgaaacu cuaaacgagu gacugcgcuc ggagaugcuc auguaucgcu    300
guuuucggac gggggguucga uuccc                                         325

<210> SEQ ID NO 75
<211> LENGTH: 360
<212> TYPE: RNA
<213> ORGANISM: Bacillus subtilis

<400> SEQUENCE: 75
ggggacguua cggauucgac agggauggau cgagcuugag cugcgagccg agaggcgauc     60
```

```
ucguaaacac gcacuuaaau auaacuggca aaacuaacag uuuuaaccaa aacguagcau    120
uagcugccua auaagcgcag cgagcucuuc cugacauugc cuaugugucu gugaagagca    180
cauccaagua ggcuacgcuu gcguucccgu cugagaacgu aagaagagau gaacagacua    240
gcucucggaa ggcccgcccg caggcaagaa gaugagugaa accauaaaua ugcaggcuac    300
gcucguagac gcuuaaguaa ucgauguuuc uggacguggg uucgacuccc accgucucca    360

<210> SEQ ID NO 76
<211> LENGTH: 325
<212> TYPE: RNA
<213> ORGANISM: Bacillus badius

<400> SEQUENCE: 76
cagggauagu ucgagcuugg gcugcgagcc ggagggccgu cuucguacca acgcaaacgc     60
cuaaauauaa cuggcaaaaa agauuuagcu uuagcugccu aauauagguu cagcugcucc    120
ucccgcuauc guccauguag ucggguaagg gguccaaacu aguggacua cgccggaguu    180 cuccgccugg ggacaaagga agagaucaau caggcuagcu gcccgacgc ccgucgauag    240 gcaaaaggaa cagugaaccc caaauauauc gacuacgcuc uagacguuc aaguggcguu    300 aucuuuggac gugggucaa cuccc                                          325

<210> SEQ ID NO 77
<211> LENGTH: 341
<212> TYPE: RNA
<213> ORGANISM: Bacillus megaterium

<400> SEQUENCE: 77
ggggacguua cggauucgac aggguaguuc gagcuuaggu ugcgagucga ggagauggcc     60
ucguuaaaac aucaacgcca auaauacug gcaaaucuaa caauaacuuc gcuuuagcug    120
cauaauagua gcuuagcguu ccucccucca ucgcccaugu gguaggguaa gggacucacu    180
uuaagugggc uacgccggag uucgccgucu gaggacgaag gaagagaaua aucagacuag    240
cgacugggac gccuguuggu aagcagaaca gcucgcgaau gaucaauaug ccaacagccg    300
uacacucgua gacgcuuaag uggccauauu ucuggacgug g                       341

<210> SEQ ID NO 78
<211> LENGTH: 315
<212> TYPE: RNA
<213> ORGANISM: Bacillus thermoleovorans

<400> SEQUENCE: 78 cgggggguagg ucgagcuuaa gcggcgagcc gaggggacg uccucguaaa aacgucaccu     60
aaagauaacu ggcaaacaaa acuacgcuuu agcugccuaa uugcugcagc uagcuccucc    120
cgccaucgcc cgcguggcgu ucgaggggcu cauauggagc gggcuacgcc caaauccgcc    180
gccugaggau gagggaagag acgaaucagg cuccgggagg ccugucggua ggcggaacgg    240
acggcgaagc gaaauauacc gacuacgcuc uagaugcuu aaguggcgau gccucuggac    300 gugggguucga uuccc                                                   315

<210> SEQ ID NO 79
<211> LENGTH: 335
<212> TYPE: RNA
<213> ORGANISM: Enterococcus faecium

<400> SEQUENCE: 79
```

-continued

| caggcacagu uugagcuuga auugcguuuc guagguuacg ucuacguuaa aacguuacag | 60 |
| uuaaauauaa cugcuaaaaa cgaaaacaac ucuuacgcuu uagcugccua aaaacaguua | 120 |
| gcguagaucc ucucggcauc gcccaugugc ucgaguaagg gucucaaauu uaguggggaua | 180 |
| cgugacaacu uuccgucugu aaguuguuaa agagaucauc agacuagcga uacagaaugc | 240 |
| cugucacucg gcaagcugua aagcgaaacc acaaaugagu ugauaugaac guagauuuuu | 300 |
| aaguggcgau uguuuggac gcgguucaa cuccc | 335 |

<210> SEQ ID NO 80
<211> LENGTH: 364
<212> TYPE: RNA
<213> ORGANISM: Enterococcus faecalis

<400> SEQUENCE: 80

| gggggcguua cggauucgac aggcauaguu gagcuugaau ugcguuucgu agguuacggc | 60 |
| uacguuaaaa cguuacaguu aaauauaacu gcuaaaaacg aaaacaauuc uuucgcuuua | 120 |
| gcugccuaaa aaccagcuag cgaagauccu cccggcaucg cccaugugcu cgggucaggg | 180 |
| uccuaaucga aguggauac gcuaaauuuu ccgucuguaa aaauuuagag gagcuuacca | 240 |
| gacucagcaa uacagaaugc cugucacucg gcacgcugua aagcgaaccu uuaaaugagu | 300 |
| guuaugaacg uagagauuua aguggcaaua uguuuggacg cgguucgac ucccgccguc | 360 |
| ucca | 364 |

<210> SEQ ID NO 81
<211> LENGTH: 346
<212> TYPE: RNA
<213> ORGANISM: Streptococcus pyogenes

<400> SEQUENCE: 81

| ggggnuuguua cggauucgac aggcauuaug aggcauguuu ugcgucccau cggcagaugu | 60 |
| aaauugccag uuaaauauaa cugcaaaaaaa uacaaacucu uacgcuuuag cugccuaaaa | 120 |
| accagcuagc gugacuucua caagauugcu ugugccugu uagaagucuc aaaauagcaa | 180 |
| gcuacgguua cgaaauugc uaguuucgug acaagagauu gauagacucc gcaaacuaau | 240 |
| ggcuugaguu augugucuuu aguuuguuaa augaagacau aaccauugga cguagacaaa | 300 |
| uauguuggca ggguguuugga cguggguucg acucccacca gcucca | 346 |

<210> SEQ ID NO 82
<211> LENGTH: 344
<212> TYPE: RNA
<213> ORGANISM: Streptococcus pneumoniae

<400> SEQUENCE: 82

| gggucguua cggauucgac aggcauuaug aggcauauuu ugcgacucgu guggcgacgu | 60 |
| aaacgcucag uuaaauauaa cugcaaaaaaa uaacacuucu uacgcucuag cugccuaaaa | 120 |
| accagcaggc gugacccgau uuggauugcu cguguucaau gacaggucuu auuauuagcg | 180 |
| agauacgauu aagccuuguc uagcgguuug auaagagauu gauagacucg caguuucuag | 240 |
| acuugaguua ugugucgagg ggcuguuaaa auaauacaua acuaugguug uagacaaaua | 300 |
| uguuggcagg uguuuggacg uggguucgac ucccaccggc ucca | 344 |

<210> SEQ ID NO 83
<211> LENGTH: 364
<212> TYPE: RNA
<213> ORGANISM: Streptococcus gordonii

<400> SEQUENCE: 83

| gggguucguua cggauucgac aggcauuaug aggcauauuu ugcgacucau cuagcggaug | 60 |
| uaaaacgcca guuaaauaua acugcaaaaa auaauacuuc uuacgcuuua gcugccuaaa | 120 |
| aaccagcggg cgugacccga uucggauugc uugugucuga ugacaggucu uauuauuagc | 180 |
| aagcuacggu agaaucuugu cuagugauuu acaagagau ugauagacua cguuagaacu | 240 |
| gagucagccg cuugauuugg gcuugaguua ugugucaaaa ucaaguuaaa acaauacaua | 300 |
| gcuaugguug uagacaaaua uguuggcaga uguuggacg ugggucgac ucccaccggc | 360 |
| ucca | 364 |

<210> SEQ ID NO 84
<211> LENGTH: 329
<212> TYPE: RNA
<213> ORGANISM: Streptococcus mutans

<400> SEQUENCE: 84

| ggggucguua cggauucgac aggcauuaug agaccuauuu ugcgacucau cuagcggaug | 60 |
| uaaaacgcca guuaaauaua acugcaaaaa auacaaauuc uuacgcagua gcugccuaaa | 120 |
| aaccagccug ugugaucaau aacaaauugc uuguguuugu ugauuggucu uauuguuaac | 180 |
| aagcugcugu ucuaaaagag uucuacugac uccgcaucgu uagaguuuga guuauguauu | 240 |
| guaacggugu uaaauaaaca cauaaccuau aguugagac aaaugggüua gcagauguuu | 300 |
| ggacgugggu ucgacucca ccggcucca | 329 |

<210> SEQ ID NO 85
<211> LENGTH: 328
<212> TYPE: RNA
<213> ORGANISM: Staphylococcus epidermidis

<400> SEQUENCE: 85

| cagggguccc cgagcuuauu aagcgugucg gaggguuggc uccgucauca acacauuucg | 60 |
| guuaaauaua acugcaaaau caaacaauaa uuucgcagua gcugcguaau agccacugca | 120 |
| ucgccuaaca gcaucuccua cgugcuguua acgcgauuca acccuaguag gauaugcuaa | 180 |
| acacugccgc uugaagucug uuuagaugaa auauaaucaa gcuaguauca guuggugu | 240 |
| uuauugcuua gcaugaugcg aaaauuauca auaaacuaca cacguagaaa gauuuguauc | 300 |
| aggaccucug gacgcgggüu caacucccc | 328 |

<210> SEQ ID NO 86
<211> LENGTH: 359
<212> TYPE: RNA
<213> ORGANISM: Staphylococcus aureus

<400> SEQUENCE: 86

| ggggacguuc auggauucga cagggguccc ccgagcucau uaagcgüguc ggaggguügu | 60 |
| cuucgucauc aacacacaca guuuauaaua acuggcaaau caaacaauaa uuucgcagua | 120 |
| gcugccuaau cgcacucugc aucgccuaac agcauuuccu augugcuguu aacgcgauuc | 180 |
| aaccuuaaua ggauaugcua aacacugccg uugaagucu guuuagaaga aacuuaauca | 240 |
| aacuagcauc auguugguüg uuuauacauu uucaugaugc gaaaccuauc gauaaacuac | 300 |
| acacguagaa agauguguau caggaccüuu ggacgcgggu ucaaaucccg ccgucucca | 359 |

<210> SEQ ID NO 87

<211> LENGTH: 334
<212> TYPE: RNA
<213> ORGANISM: Lactobacillus acidophilus

<400> SEQUENCE: 87

| caggcguaga | cccgcauuga | cugcgguucg | uagguuacgu | cuacguaaaa | acguuacagu | 60 |
| uaaauauaac | ugcaaauaac | aaaaauucuu | acgcauuagc | ugcuuaauuu | agcgcaugcg | 120 |
| uugcucuuug | ucgguuuacu | cguggcugac | acugaguauc | aacuuagcga | guuacguuua | 180 |
| acuaccucac | cugaauaguu | gaaaagaguc | uuagcagguu | agcuagucca | uacuagcccu | 240 |
| guuauauggc | guuuuggacu | agugaaguuc | aaguaauaua | acuaugaucg | uagaggucag | 300 |
| ugacgagaug | cguuuggaca | gggguucaac | uccc | | | 334 |

<210> SEQ ID NO 88
<211> LENGTH: 347
<212> TYPE: RNA
<213> ORGANISM: Aquifex aeolicus

<400> SEQUENCE: 88

| gggggcggaa | aggauucgac | ggggacaggc | gguccccgag | gagcaggccg | gguggcuccc | 60 |
| guaacagccg | cuaaaacagc | ucccgaagcu | gaacucgcuc | ucgcugccua | auuaaacggc | 120 |
| agcgcgucccc | cgguagguuu | gcggguggcc | uaccggaggg | cgucagagac | acccgcucgg | 180 |
| gcuacucggu | cgcacggggc | ugaguagcug | acaccuaacc | cgugcuaccc | ucggggagcu | 240 |
| ugcccgugggg | cgacccgagg | ggaaauccug | aacacgggcu | aagccuguag | agccucggau | 300 |
| guggccgccg | uccucggacg | cggguucgau | ucccgccgcc | uccacca | | 347 |

<210> SEQ ID NO 89
<211> LENGTH: 355
<212> TYPE: RNA
<213> ORGANISM: Thermotoga maritima

<400> SEQUENCE: 89

| gggggcgaac | gguuucgacg | gggaugagu | ccccugggaa | gcgagccgag | gucccaccu | 60 |
| ccucguaaaa | aaggugggac | aaagaauaag | ugccaacgaa | ccuguugcug | uugccgcuua | 120 |
| auagauaagc | ggccguccuc | uccgaaguug | gcugggcuuc | ggaagagggc | gugagagauc | 180 |
| cagccuaccg | auucaguucg | ccuuccggcc | ugaaucggga | aaacucagga | aggcugugggg | 240 |
| agaggacacc | cugcccgugg | gagguccccuc | ccgagagcga | aaaacgggc | ugcgcucgga | 300 |
| gaagcccagg | ggccuccauc | uucggacggg | gguucgaauc | ccccgccuc | cacca | 355 |

<210> SEQ ID NO 90
<211> LENGTH: 355
<212> TYPE: RNA
<213> ORGANISM: Thermotoga neapolitana

<400> SEQUENCE: 90

| ggggggcggaa | aggauucgac | ggggauggag | uccccuggga | agcgagccga | ggucccacc | 60 |
| uccucguaaa | aaggguggga | acacgaauaa | gugccaacga | accuguugcu | guugccgccu | 120 |
| aauagauagg | cggccguccu | cuccggaguu | ggcugggcuc | cggaagaggg | cgugagggau | 180 |
| ccagccuacc | gaucgggcu | ccgccuuccg | gcccggaucg | ggaagguuca | ggaaggcugu | 240 |
| gggaagcgac | acccugcccg | uggggggucc | uucccgagac | acgaaacacg | ggcugcgcuc | 300 |
| ggagaagccc | aggggccucc | aucuucggac | gggggguucga | uucccgccgc | cucca | 355 |

<210> SEQ ID NO 91
<211> LENGTH: 350
<212> TYPE: RNA
<213> ORGANISM: Thermus thermophilus

<400> SEQUENCE: 91

| | | | | | |
|---|---|---|---|---|---|
| gggggugaaa | cggucucgac | gggggucgcc | gagggcgugg | cugcgcgccg | aggugcgggu | 60 |
| ggccucguaa | aaacccgcaa | cggcauaacu | gccaacacca | acuacgcucu | cgcggcuuaa | 120 |
| ugaccgcgac | cucgcccggu | agcccugccg | ggggcucacc | ggaagcgggg | acacaaaccc | 180 |
| ggcuagcccg | gggccacgcc | cucuaaccc | ggcgaagcu | ugaaggggc | ucgcuccugg | 240 |
| ccgcccgucc | gcgggccaag | ccaggaggac | acgcgaaacg | cggacuacgc | gcguagaggc | 300 |
| cacgccccgg | cgaccuucgg | acggggguuc | gauucccccc | accuccacca | | 350 |

<210> SEQ ID NO 92
<211> LENGTH: 349
<212> TYPE: RNA
<213> ORGANISM: Deinococcus radiodurans

<400> SEQUENCE: 92

| | | | | | |
|---|---|---|---|---|---|
| gggggugacc | cgguuucgac | aggggaacug | aaggugaugu | ugcgugucga | ggugccguug | 60 |
| gccucguaaa | caaacggcaa | agccauuuaa | cuggcaacca | gaacuacgcu | cucgcugcuu | 120 |
| aagugagaug | acgaccgugc | agcccggccu | uuggcgucgc | ggaagucacu | aaaaaagaag | 180 |
| gcuagcccag | gcgauuccc | auagccgacg | gcgaaacuuu | auggagcuac | ggccugcgag | 240 |
| aaccugccca | cuggugagcg | ccggcccgac | aaucaaacag | ugggauacac | acguagacgc | 300 |
| acgcuggacg | gaccuuugga | cggcgguucg | acuccgccca | ccuccacca | | 349 |

<210> SEQ ID NO 93
<211> LENGTH: 347
<212> TYPE: RNA
<213> ORGANISM: Deinococcus proteolyticus

<400> SEQUENCE: 93

| | | | | | |
|---|---|---|---|---|---|
| gggggcggaa | aggauucgac | gggggaacgg | aaagcgcugc | ugcgugccga | ggagccguug | 60 |
| gccucguaaa | caaacggcaa | agccauuaac | uggcgaaaau | aacuacgcuc | ucgcugcuua | 120 |
| agugagagca | gugaccacgu | agcccgccu | uuggcgacgu | ugaacugag | acaaaagaag | 180 |
| gcuagcuuag | gugagguucc | auagccaaaa | gugaaaccaa | auggaaauaa | ggcggacggc | 240 |
| agccuguuug | cuggcagccc | aggcccgaca | auuuaagagc | agacuacgca | cguagaugca | 300 |
| cgcuggaugg | accuuuggac | ggcgguucga | uucccgccgc | cucacca | | 347 |

<210> SEQ ID NO 94
<211> LENGTH: 334
<212> TYPE: RNA
<213> ORGANISM: Thermomicrobium roseum

<400> SEQUENCE: 94

| | | | | | |
|---|---|---|---|---|---|
| cagggccgua | ggugcgagga | uugcaggucg | aggucgccca | cgaacucgua | aaaggggca | 60 |
| ccaaguaacu | ggcgagcgcg | aacucgcucu | ggcugcguaa | uucacgcagc | cacgucugcc | 120 |
| cggacccuuc | ccugguggu | ucggagcggg | gccgcaaga | ccgggguggcc | ccuggcccaa | 180 |
| gcgccggugc | gggccaagguc | aagcgugauc | cggcucggcu | gaccgggauc | cugucggugg | 240 |
| gagccuggca | gcgacaguag | aacaccgacu | aagccguag | cauauccucg | gcugaacgcu | 300 |
| cuggacgggg | guucaacucc | cgccagcucc | acca | | | 334 |

<210> SEQ ID NO 95
<211> LENGTH: 353
<212> TYPE: RNA
<213> ORGANISM: Coprothermobacter proteolyticus

<400> SEQUENCE: 95

```
gggggcggaa aggauucgac ggggagucgg agccuugagc ugcaggcagg guuggcugcc      60
acaccuuaaa aagguagca aggcaaaaau aaaugccgaa ccagaauuug cacuagcugc     120
uuaauguaag cagccgcucu ccaaacugag gcugcauaag uuuggaagag cgucaaccca     180
ugcagcggcu cuuaagcagu ggcaccagcu guuuaagggu gaaaagagug gugcggggca     240
gugcgguugg gcuuccuggg cugcacuguc gagacuucac aggagggcua agccuguaga     300
cgcgaaaggu ggcggcucgu cggacgcggg uucgauuccc gccgccucca cca            353
```

<210> SEQ ID NO 96
<211> LENGTH: 360
<212> TYPE: RNA
<213> ORGANISM: Herpetosiphon aurantiacus

<400> SEQUENCE: 96

```
gggggcggaa aggauucgac ggggagggcc aaucguaagu ggcaagccga gacgcugagc      60
cucguuaaau cggcaacgcc auuaacuggc aaaaacacuu ccgcgcucc uguagcgcuu      120
gcugccuaau uaaggcaaca cgucucuacu agccucagcc cgaugggcuu guagcggcga     180
cacuuagucg ggucgcuccc cuaguuaugu cuguggggcua ggggcuaaga uuaacaggcu    240
ggucguggcc cgcuuugucu aucgguuggu gcaccgauaa gauuuaauca auagacuacg     300
cuuguagaug cuugcgguuu aacuuuuugg acgcggguuc gauucccgcc gccuccacca     360
```

<210> SEQ ID NO 97
<211> LENGTH: 355
<212> TYPE: RNA
<213> ORGANISM: Thermodesulfobacterium commune

<400> SEQUENCE: 97

```
gggggcggaa aggauucgac ggggauaggu aggauuaaac agcaggccgu ggucgcaccc      60
aaccacguua aauagggugc aaaaacacaa cugccaacga auacgccuac gcuuuggcag     120
ccuaagcgug cugccacgca ccuuuagacc uugccugugg gucuaaaggu gugugaccua     180
acaggcuuug ggaggcuuaa ucgguggggu uaagccuccc gagauuacau cccaccuggu     240
aggguugcuu ggugccugug acaagcaccc uacgagauuu ucccacaggc uaagccugua     300
gcgguuuaau cugaacuauc uccggacgcg gguucgauuc ccgccgccuc cacca           355
```

<210> SEQ ID NO 98
<211> LENGTH: 329
<212> TYPE: RNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 98

```
gggnnnnauu uggaauucgc cgaaugcuag aaguggaggc ugcaugccgc ggaugauucg      60
uuggccgcuu uaccaauucg gaucaaacaa cuaaaugcgg acucuaacga gcuugcccuc     120
gccgcuuaau ugacggugac guuccuccag ugaagucugu gaauuggagg agcgacuacu     180
uacaggcugg ccaaaagagc gggcgaccgg ccccaaggcg agaucuacag gccgcuggau     240
```

```
ggacggcauc cuggcaguag gaggcuggac aucgagauca aaunauugcc ugagcaugga    300
gacgcuuuca uaaaggnguu cggacaggg                                     329
```

<210> SEQ ID NO 99
<211> LENGTH: 351
<212> TYPE: RNA
<213> ORGANISM: Dictyoglomus thermophilum

<400> SEQUENCE: 99

```
gggggcggaa aggauucgac ggggaguaca aggaucaaaa gcugcaagcc gaggugccgu    60
uaccucguaa acaacggca aaaagaagu gccaacacaa auuuagcauu agcugcuuaa     120
uuuagcagcu acgcucuucu aacccgggcu ggcaggguua aagggugguc auaaugagcc   180 agcugcccu uccgacuccc cuaaggaagg gaaagaugua ggggauaggu gcuuacagaa    240
uccugcggga gggagucugu aagugccgaa aaguuaaaac ucccgcuaag cuuguagagg   300
cuuuugauuc uugcucucug gacgcgggu cgauucccgc cgccuccacc a             351
```

<210> SEQ ID NO 100
<211> LENGTH: 399
<212> TYPE: RNA
<213> ORGANISM: Synechocystis sp. PCC 6803

<400> SEQUENCE: 100

```
ggggccgcaa ugguuucgac agguuggcga aagcuugccc gugauacagg ucgagaguga    60
gucuccucuc gcaaaucaaa ggcucaaaaa aaaguaacug cgaauaacau cgucagcuuc   120
aaacggguag ccauagcagc cuagucugua aaagcuacau uuucuuguca aagaccguuu   180
acuucuuuuc ugcuccguu aaggauuaga gguuaaccccc aacggaugcu uguuuggcu    240 cuucucuagu uagcuaaaca aucaagacuc agacuagagc aucccaccau cagggauaau   300
cgauggcccc cguccuaggg cuagaaggac uaaaccugug aaugagcgga aaguuaauac    360
ccaguuugga cagcaguuca auucugcucg gcuccacca                           399
```

<210> SEQ ID NO 101
<211> LENGTH: 385
<212> TYPE: RNA
<213> ORGANISM: Nostoc muscorum

<400> SEQUENCE: 101

```
ggguccgucg guuucgacag guuggcgaac gcuacucugu gauucagguc gagagugagu    60
cuccucugca aaucaaggcu caaaacaaaa guaaaugcga auaacaucgu uaaauuugcu   120
cguaaggacg cucuaguagc ugccuaaaua gccucuuuca gguucgagcg cuuucgguuu   180
gacuccguua aggacugaag accaaccccc aacggaugcu cuagcaaugu ucucuggüug    240 gcuugcuagc uaagauuuaa ucagagcauc cuacguucgg gauaaugaac gauucccgcc    300
uugaggguca gaaaggcuaa accgugaauu gagcgggggg ucaauaccca auuuggacag    360
caguucgacu cugcucgauc cacca                                          385
```

<210> SEQ ID NO 102
<211> LENGTH: 393
<212> TYPE: RNA
<213> ORGANISM: Synechococcus PCC 6301

<400> SEQUENCE: 102

```
ggggcuguaa ugguuucgac guguugguga auccuucacc gugauucagg ccgagaggga    60
```

```
guccacucuc guaaauccag cucaaccaa aaguaacugc gaacaacauc guuccuuucg      120
cucguaaggc ugcuccugua gcugcuuaaa cgccacaaac uuucggcuc gagcgucuag      180 ucguagacuc cguuaauacg ccuagacuua accccccaac ggaugcugag uggcggccuc     240 aggccgucc ucucgcuaag caaaaaccug agcaucccgc caacggggau aaucguuggc      300
ucccgcacag ugggucaacc gugcuaagcc ugugaacgag cggaaaguua cuagucaaug     360
cggacagcgg uucgauuccg cucagcucca cca                                  393

<210> SEQ ID NO 103
<211> LENGTH: 312
<212> TYPE: RNA
<213> ORGANISM: Leptolyngbya sp. (ATCC 27894)

<400> SEQUENCE: 103
ggcucaaaaa aauagaugca acaacaucg uaccuuucgc ucguaaaacu gcaccuguug       60
cagcauaaaa caccucuaau ucagguucga gcgcuuaccg ucugacaccg uuaaagauag     120
uaagcacaac cccaacgguu gcucuagaau uucgccuuug gucggcauuc uagcuaagac     180
aauaccaaag cauccuauug uccgggacaa aggacaguuc ccgcuucgag gauuagagaa     240
gcuaaaccug ugaaugauug auagagcuaa uacccaguuu ggacacgggu caacucccg      300 ccagcuccac ca                                                         312

<210> SEQ ID NO 104
<211> LENGTH: 323
<212> TYPE: RNA
<213> ORGANISM: Porphyra purpurea

<400> SEQUENCE: 104
ggggcugcaa gguucuaca uugugaaaaa acaaauauau gaaaguaaaa cgagcucauu        60
auuagagcuu uuaguuaaau aaaugcagaa aauaauauua uugcuuuuuc ucgaaaauua      120
gcuguugcau aaauagucuc aauuuuugua auucgaagug auagacucuu auacacuacg     180
aauauucugu uagaguugcu cuuaauaaaa gaaaaguaaa aaaauacaaa ucuuuauguu     240
uuuuaccuga auugauucaa uuuaaggguua guauuuuug auuuuuacaa uggacguggg    300 uucaagucccc accagcucca cca                                            323

<210> SEQ ID NO 105
<211> LENGTH: 294
<212> TYPE: RNA
<213> ORGANISM: Cyanophora paradoxa

<400> SEQUENCE: 105
ggggcuguuu agguuucgac guuuuuuucu aauuauguuu guuaagcaag ucgaggauuu       60
guucuaucuc gaaaaucaag aacucucaaa auuuaaacgc aacuaauauu guacguuuua     120
accguaaagc agcuuucgcu guuuaauaau acuuuuaau uuaaaaaccu aauuuuuuua      180
ggaauuuauu uauuuauugu uuauccugcu uaaugaauua aaaaaagcua acuugugaa      240 uaaacgcaua auuuaaaaaa acggacgugg guucaaauuc caccagcucc acca           294

<210> SEQ ID NO 106
<211> LENGTH: 371
<212> TYPE: RNA
<213> ORGANISM: Odontella sinensis

<400> SEQUENCE: 106
ggggcugacu ugguuucgac auuuuaaaaau uguuacagua ugaugcaggu cgaaguuucu      60
```

```
aaucuucgua aaaaaagaga aauuuauaau aaaugcuaau aauuuaauuu cuucugaguu    120
uaaaaguuua ucaacuaagc aaaauaguuu aaauuuaagu uuugcuguuu aaguuuuaug    180
cacauuuaau gaucaguaa auaacuuugu ucgcuauaau uuauauuuau aacuagacuu    240
uugucuuuuu uauaguuuag aauaacuuua ucauuucaaa ccucguucca ucaguugaa     300 cuaaaccugu gaacgaauac uauaauaaaa uuuuuagaug gacgugggu cgacucccau    360 cagcuccacc a                                                          371

<210> SEQ ID NO 107
<211> LENGTH: 348
<212> TYPE: RNA
<213> ORGANISM: Thalassiorsira weissflogii

<400> SEQUENCE: 107
ggggcugauu ugguuucgac auuuaaaacu ucuuucuaug ugucaggauca aaguuuguau    60 ucuuuguaaa aaauacuaa aauacuaaua aaugcuaaua auauaauacc guuuauuuuu    120
aaagcaguaa aaacaaaaaa agaagcaaug gcuuuaaauu uugcuguaua guucauuaac    180
uuagguuauu aaauauuuuu ucauuauaac uggacuuuuu cucaguuuau aguuuagaau    240
aaauuuaaau uuugcaaaac ucguucgaaa auuuucgggc uaaaccugua aacgcaaaua    300
cuaagaaauu uuagauggac augggucaa uuccacucag uuccacca                  348

<210> SEQ ID NO 108
<211> LENGTH: 330
<212> TYPE: RNA
<213> ORGANISM: Guillardia theta

<400> SEQUENCE: 108
ggggcugauu uggauucgac auauaaauuu gcguguuuca uuaugaagca agucaaguuu    60
aaugaucuug uaaaaaacau uaaagaucaa auaaaugcaa gcaauauagu ucauuuagu    120 ucaaaacguu uagcucuuuu ugcauaagca aaaugguguua auaacuuucu aguagaaau    180 uggagaaguu uacuaagauu uauauuuacu ccauaauuuu uuuaaagaug guaaaaaggu    240
gauucaucau uuguauguuu cuaaacuuug ugaaagaaua gugggcucca uuuauaauga    300
acguggguuc aaauccccacc agcuccacca                                      330

<210> SEQ ID NO 109
<211> LENGTH: 353
<212> TYPE: RNA
<213> ORGANISM: Mycoplasma hyorhinis

<400> SEQUENCE: 109
cauacauaaa aggauauaaa uugcaguggu cuuguaaacc auaagacaau uucuuuacua    60
agcggaaaag aaaacaaaaa agaagauuau ucauuauuaa ugaaugcuuc aacucaauca    120
aaucuagcuu uugcauuuua aaaaacuagu agaccaauuu gcuucacacg aauuguaauc    180
uuuauauuag agaauaguua aaaucgauu cacuuuuuaa ugaauuuaua gaucacaggc    240
uuuuuuaauc uuuuuguuau uuuagauaaa gagucuucu aaaaauaacu aaacuguagg    300
aauuuauauu uaauuaugcg uggacccggg uucaacuccc gccagcucca cca           353

<210> SEQ ID NO 110
<211> LENGTH: 411
<212> TYPE: RNA
<213> ORGANISM: Mycoplasma capricolum
```

-continued

<400> SEQUENCE: 110

```
ggggauguca uggauuugac aggauaucuu uaguacauau aagcaguagu guuguagacu     60
auaaauacua cuagguuuaa aaaaacgcaa auaaaaacga agaaacuuuu gaaaugccag    120
cauuuaugau gaauaaugca ucagcuggag caaacuuuau guuugcuuaa uaacuacuag    180
uuuaguuaua guauuucacg aauuauagau auuuuaagcu uuauuuauaa ccguauuacc    240
caagcuuaau agaauauaug auugcaauaa auauauuuga aaucuaauug caaaugauau    300
uuaaccuuua guuaauuuua guuaaauauu uuaauuagaa aauuaacuaa acuguagaaa    360
guauguauua auauaucuug gacgcgaguu cgauucucgc caucuccacc a             411
```

<210> SEQ ID NO 111
<211> LENGTH: 381
<212> TYPE: RNA
<213> ORGANISM: Mycoplasma pirum

<400> SEQUENCE: 111

```
caugaaugau ggacccauag aggcaguggg guaugccccu uauagcucaa gguuuaaauu     60
aaccgacaaa acugacgaaa acguugccgu ugauacaaau uuauuaauca accaacaagc    120
ucaauuuaac uacgcauuug cauaguauaa aaaaauaaau ugugcuacuc auuguaauua    180
gguuacuaaa uuacuuuguu uuauauaguc cuguaacuag uucuagugau gucuauaaac    240
uagaaugaga uuuauagacu uauuuguugg cgguugugcc auagccuaaa ucaacaaaga    300
caauuuauuu augguacuaa acuguagauu cuaugaugaa auuauuugug gaaacggguu    360
cgauucccgc caucuccacc a                                              381
```

<210> SEQ ID NO 112
<211> LENGTH: 387
<212> TYPE: RNA
<213> ORGANISM: Mycoplasma pneumoniae

<400> SEQUENCE: 112

```
ggggauguag agguuuugac auaauguuga aaggaaaaca guugcagugg gguaugcccc     60
uuacagcucu agguauaaua accgacaaaa auaacgacga aguuuuggua gauccaaugu    120
ugaucgcuaa ccaacaagca aguaucaacu acgcuuucgc uuagaacaua cuaaagcuac    180
acgaauugaa ucgccauagu uugguucgug ucacaguuua uggcucgggg uuaacugguu    240
caacuuaauc cuuaaauuau gaacuuaucg uuuacuuguu ugucuuauga ucuaaaguaa    300
gcgagacauu aaaacauaag acuaaacugu agaagcuguu uuaccaaucc uuuauggaaa    360
cggguucgau ucccgucauc uccacca                                        387
```

<210> SEQ ID NO 113
<211> LENGTH: 388
<212> TYPE: RNA
<213> ORGANISM: Mycoplasma genitalium

<400> SEQUENCE: 113

```
ggggauguuu uggguuugac auaaugcuga uagacaaaca guagcauugg gguaugcccc     60
uuacagcgcu agguucaaua accgacaaag aaaauaacga aguguuggua gauccaaauu    120
ugaucauuaa ccaacaagca aguguuaacu uugcuuuugc auaaguagau acuaaagcua    180
cagcugguga auagucauag uuugcuagcu gucauaguuu augacucgag guuaaaucgu    240
ucaauuuaac cuuuaaaaau agaacuuguu guuuccauga uuguuuugug aucaauugga    300
aacaagacaa aaauccacaa aacuaaaaug uagaagcugu uuguuguguc cuuuauggaa    360
```

```
acggguucga uucccgucau cuccacca                                          388

<210> SEQ ID NO 114
<211> LENGTH: 412
<212> TYPE: RNA
<213> ORGANISM: Ureaplasma urealyticum

<400> SEQUENCE: 114
ggggauguca cgguuucgac gugacacauu aauuuuuaau ugcaguggggg uuagccccuu       60 aucgcuuucg aggcauuuua aaugcagaaa auaaaaaauc uucugaagua gaauuaaacc      120
cagcguuuau ggcuucagcu acuaaugcaa acuacgcuuu ugcguacuaa uuaguuauua      180
guagaaacgu ucauuaacau aauuacuauu gguugguuu ugggcuuauu uuacaauagu       240
uuuaaauuua aaauucuuau uguuguuaa auuuaaauag auuuaacaaa uaguuaguua       300 auuuaaauu uguuuauua guauuaacu acacuauuuu uaauaaaacu aaacuguaga         360
uauuauuaau uaugguuugc ggaaaggggu ucgauucccc ucaucuccac ca              412

<210> SEQ ID NO 115
<211> LENGTH: 365
<212> TYPE: RNA
<213> ORGANISM: Mycoplasma salivarium

<400> SEQUENCE: 115
caggcauucg auucauuaug uugcaguggu uugcaaacca uaaggcacua ggcuuuuuua       60
aacgcaaaag accaaaaaac agaagaucaa gcaguugauc uagcauuuau gaauaauuca      120
caaaugcaau caaaucuagu uuucgcuuag uaaaauuagu caauuauua uggugcucaa       180 cauaauaaau gguaguauga gcuuaauauc auaugauuuu aguuaauaug auaggauuug      240
uaacuaaacu auguauaga aauuuguaaa uauauauau gacauaggaa auuuaauuua       300
cuaaacugua gaugcauaau guugaagaug uguggaccgg gguucaacuc ccgccagcuc      360
cacca                                                                  365

<210> SEQ ID NO 116
<211> LENGTH: 363
<212> TYPE: RNA
<213> ORGANISM: Clostridium innocuum

<400> SEQUENCE: 116
cggggauaug ucgguacag acugcagucg aguggguuacg uaauaaccaa uuaaauuuaa       60
acggaaaaac uaauuagcu aaccucuuug guggaaacca gagaauggcu uucgcugcuu       120
aauaaccgau auagguucgc agccgccucu gcaugcuucu uccuugacca guggaugug       180 cgcguaagac gcaagggaua aggaaucugg uuugccugag aucagauuca cgaaaauucu      240
ucaggcacau ucaucagcgg auguucauga ccugcugaug ucuuaaucuu cauggacuaa      300
acuguagagg ucuguacgug gggcuguuuc uggacaggag uucgauuccc gccgccucca      360
cca                                                                    363

<210> SEQ ID NO 117
<211> LENGTH: 359
<212> TYPE: RNA
<213> ORGANISM: Mycoplasma fermentans

<400> SEQUENCE: 117
caugcauugg gugauacuaa uaucaguagu uuggcagacu auaaugcauc uaggcuuuau       60
```

| | |
|---|---|
| aaucgcagaa gauaaaaaag cagaagaagu uaauauuucu ucacuuauga uugcacaaaa | 120 |
| aaugcaauca caaucaaacc uugcuuucgc uuaguuaaaa gugacaagug guuuaaagu | 180 |
| ugacauuuuc cuauauauuu uaaaucggc uuuuaaggag aacaggaguc ugaaagggu | 240 |
| ccaaaaaucu auauuguuug cauuucggua guauagauua auuagaaaug auaaacugua | 300 |
| aaaaguauug guauugacuu ggugugugga cucggguuca acucccgcca gcuccacca | 359 |

<210> SEQ ID NO 118
<211> LENGTH: 320
<212> TYPE: RNA
<213> ORGANISM: Acidobacterium capsulatum

<400> SEQUENCE: 118

| | |
|---|---|
| cggggttugac ugcggcaaag aggcaugccg gggggugggc acccguaauc gcucgcaaaa | 60 |
| caauacuugc caacaacaau cuggcacucg cagcuuaauu aaauaaguug ccguccucug | 120 |
| aggcuucgcc uguggccga ggcaggacgu cauacagcag gcugguuccu ucggcugggu | 180 |
| cugggccgcg gggaugagau ccacggacua gcauucugcg uaucugucg cuucuaagcg | 240 |
| cagagugcga aaccuaaagg aaugcgacug agcauggagu cucuuuucug acaccaauuu | 300 |
| cggacgcggg uucgauuccc | 320 |

<210> SEQ ID NO 119
<211> LENGTH: 319
<212> TYPE: RNA
<213> ORGANISM: Fusobacterium mortiferum

<400> SEQUENCE: 119

| | |
|---|---|
| cgggguuaug agguuauagg uagcaugcca ggaugaccgc ugugagaggu caacacaucg | 60 |
| uuuagaugga aacagaaaau acgcuuuagc ugcuuaauua gucagcucac cucugguuuc | 120 |
| ucucuucugu aggagaaucc aaccgaggug uuaccaauau acagauuacc uuuagugauu | 180 |
| ucucuaagcu caaagggaca uuuuagagaa uagcuucagu uagcccuguc ugcgggagug | 240 |
| auuguugcga aauaaaauag uagacuaagc auuguagaag ccuauggcgc ugguaguuuc | 300 |
| ggacacgggu ucaacuccc | 319 |

<210> SEQ ID NO 120
<211> LENGTH: 329
<212> TYPE: RNA
<213> ORGANISM: Fibrobacter succinogenes

<400> SEQUENCE: 120

| | |
|---|---|
| cagggttuacc gaaguguuag uugcaagucg aggucucaga cgagggcuac ucguuaaaaa | 60 |
| gucugaaaaa aaauaaguagc ugacgaaaac uacgcacucg cugccuaauu aacggcaacg | 120 |
| ccgggccuca uuccgcuccc aucggggugu acguccggac gcaauauggg auaggaagu | 180 |
| gucaugccug ggggcaucuc ccgagauuuu cuaggcuggu caaaccccgc gccgaccuuc | 240 |
| uugggcgugg auaagacgag aucuuaaauu cgaagggaac acuuguagga acguacaugg | 300 |
| acgugauuuu ggacaggggu ucaacuccc | 329 |

<210> SEQ ID NO 121
<211> LENGTH: 300
<212> TYPE: RNA
<213> ORGANISM: Artificial
<220> FEATURE:
<223> OTHER INFORMATION: isolated from rumenal fluid

<400> SEQUENCE: 121

-continued

```
acgcccuugu ucagacgag ggcacucguu aaaaagucug aaaagaauaa cugcagaacc      60
uguagcuaug gcugcuuaau uuaagggcaa cccuuggauc cgccuccauc ccgaaggggu     120
ggcauccgag ucgcaaaucg ggauaggaug gaucuuggca acgaggagua cauccgaaau    180
uugucgcugc uggcugaagc aucgccguuc ucucuuuggg cuggcaaggc aagauuaaau    240
ucagaggaua agcguguagu agcgagugag uaggcguuuu uggacgcggg uucaagucccc   300
```

<210> SEQ ID NO 122
<211> LENGTH: 330
<212> TYPE: RNA
<213> ORGANISM: Pirellula staleyi

<400> SEQUENCE: 122

```
ccggauagcc ugaagcgaau acggcgugcc guugguugauc agauggccac guaaaaagcu   60
gaucacaaac uuaacugccg agagcaaucu cgcacuugcu gccuaacuaa acggauagcuu  120 ccgacugagg gcuuuagccg agaggcccaa aaguugguc accaaauccg gaccgcccucg   180 ugccaugauc gaaacgcacg aggucaaaaa aguuucgauc uagugcaggg uguagcagc    240 agcuaggcga caaacugugc aaaaaucaaa uuuucugcua cgcacguaga uguguucgug   300
aaaaugucuc gggacggggg uucaacuccc                                    330
```

<210> SEQ ID NO 123
<211> LENGTH: 329
<212> TYPE: RNA
<213> ORGANISM: Planctomyces maris

<400> SEQUENCE: 123

```
cugguucacc guauguuaag guggcggugc cguggugau caguuggcca cguaaaaagc     60
ugaucacaau cuaauugcaa acaagcaauu ucaauggcu gcuuaauaaa agcaaccccg    120
gcuuaggaau cucugucuga ggaguccgac agcggucac aaaaucagac ugguaucaga    180
ucaauguccg cuccgucuga acgagauuc guggugacu gguuccaac aggcucuguu     240 uaucgugccc gaagaaacga gacucaaacg auaaaauaug caccguagag gcuuuagcug   300 agguucaca ggacgcgggu ucaacuccc                                      329
```

<210> SEQ ID NO 124
<211> LENGTH: 318
<212> TYPE: RNA
<213> ORGANISM: Artificial
<220> FEATURE:
<223> OTHER INFORMATION: isolated from sludge

<400> SEQUENCE: 124

```
cagggaacca ggaguguga gaugcaugcc ggagacgcug uccgcuccgu uaucaagcag     60
cacaacaaaa uaauugcaaa caacaauuac uccuuagcag cguaagcagc uaacguucaa   120
ccucuccgga ccgccgggag gggauuuggg cgucgaaaca gcgcggacgc uccggauagg   180
acgcccauaa uauccggcua agaccauggg ucuggcucuc gcgggucuga uugucuucca   240
ccgcgcgggc cgcgaucaaa gacaacuaag cauguagguu cuugcauggc cuguucuuug   300
gacgcggguu cgauuccc                                                  318
```

<210> SEQ ID NO 125
<211> LENGTH: 407
<212> TYPE: RNA
<213> ORGANISM: Porphyromonas gingivalis

<400> SEQUENCE: 125

```
ggggcugacc ggcuuugaca gcgugaugaa gcgguaugua agcauguagu gcguggguggg      60 cuugcacuau aaucucagac aucaaaaguu uaauuggcga aaauaacuac gcucucgcug      120
cguaaucgaa gaauaguaga uuagacgcuu caucgccgcc aaaguggcag cgacgagaca      180
ucgcccgagc agcuuuuccc cgaaguagcc cgauggugcg gugcugacaa aucgggaacc      240
gcuacaggau gcuuccugcc uguggucaga ucgaacggaa gauaaggauc gugcauuggg      300
ucguuucagc uccgcucgc ucacgaaaau ccaacugaa acuaaacaug uagaaagcau      360
auugauucca uguuuggacg aggguucau ucccuccagc uccacca                       407
```

<210> SEQ ID NO 126
<211> LENGTH: 379
<212> TYPE: RNA
<213> ORGANISM: Bacteroides thetaiotaomicron

<400> SEQUENCE: 126

```
cagcgggcag aaaugguagg uaagcaugca gugggucggu aauuuccacu uaaaucucag      60
uuaucaaaac uuuaucuggc gaaacuaauu acgcucuugc ugcuuaaucg aaucacagua      120
gauuagcuua auccaggcac uaggugccca ggagagacau cacucggaag cuguugcucc      180
gaagcauucc gguucagugg ugcaguaaca ucggggauag ucagaagcgg ccucgcguuu      240
uugaugaaac uuuagaggau aaggcaggaa uugauggcuu ugguucugcu ccugcacgaa      300
aauuuaggca aagauaagca uuagaaaagc uuaugauuuc cucguuugga cgaggguuca      360
acucccgcca gcuccacca                                                    379
```

<210> SEQ ID NO 127
<211> LENGTH: 404
<212> TYPE: RNA
<213> ORGANISM: Chlorobium tepidum

<400> SEQUENCE: 127

```
ggggaugaca ggcuaucgac aggauaggug ugagaugucg uugcacuccg aguuucagca      60
uggacggacu cguuaaacaa gucuauguac caauagaugc agacgauuau ucguaugcaa      120
uggcugccug auuagcacaa guuaauucag aagccaucgu ccugcgguga augcgcuuac      180
ucugaagccg ccggauggca uaacccgcgc uuagccuac ggguucgcgc aaguaagcuc      240
cguacauuca ugcccgaggg ggugugcggg uaaccaaucg ggauaagggg acgaacgcug      300
cuggcggugu aaucggacca cgaaaaacca accaccagag augaguguggg uaacugcauc      360 gagcaguguc cuggacgcgg guucaaguc cgccaucucc acca                         404
```

<210> SEQ ID NO 128
<211> LENGTH: 372
<212> TYPE: RNA
<213> ORGANISM: Chlorobium limicola

<400> SEQUENCE: 128

```
caggauacgu gugagauguc guugcacucc gaguuucagc auggacggac ucguuaaaca      60
agucuaugua ccauuagaug cagacgauua uucguaugca auggcugccu gauuagcaca      120
aguuaacuca gacgccaucg uccugcgugu aaugcgcuua cucugaagcc gccggauggc      180
auaacccgcg cuugagccua cggguucgcg caaguaagcu ccgacauuc augcccgagg      240 ggcugugcgg guaauuucuc gggauaaggg gacgaacgcu gcuggcggug uaaucggccc      300
acgaaaaccc aaucaccaga gaugagugug gugacugcau cgagcagugu uuggacgcg      360
```

```
gguucaacuc cc                                                         372

<210> SEQ ID NO 129
<211> LENGTH: 420
<212> TYPE: RNA
<213> ORGANISM: Chlamydia trachomatis

<400> SEQUENCE: 129 gggggguguaa agguuucgac uuagaaauga agcguuaauu gcaugcggag ggcguuggcu     60
ggccuccuaa aaagccgaca aaacaauaaa ugccgaaccu aaggcugaau gcgaaauuau    120
cagcuucgcu gaucucgaag aucuaagagu agcugcuuaa uuagcaaagu guuaccuaa     180 auacggguga cccgguguuc gcgagcucca ccagagguuu ucgaaacacc gucauguauc    240
ugguuagaac uuagguccuu uaauucucga ggaaaugagu uugaaauuua augagagucg    300
uuagucucua uaggguuuuc uagcugagga gacauaacgu auaguaccua ggaacuaagc    360
auguagaggu uagcggggag uuuacuaagg acgagaguuc gacucucucc accuccacca    420

<210> SEQ ID NO 130
<211> LENGTH: 421
<212> TYPE: RNA
<213> ORGANISM: Artificial
<220> FEATURE:
<223> OTHER INFORMATION: Chlamydia trachomatis mouse isolate

<400> SEQUENCE: 130 gggggguguaa agguuucgac uuagaaauga agcguuaauu gcaugcggag ggcguuggcu     60
ggccuccuaa aaagccgaca aaacaauaaa ugccgaaccu aaggcugaau gcgaaauuau    120
cagcuucgcu gaucuuaaug aucuaagagu ugcugcuuaa uuagcaaagu guuaccuaa     180 guacugguaa cccgguguuc gcgagcucca ccagagguuu ucgaaacgcc gucauuuauc    240
ugguuagaau uagggccuuu uaacucucaa gggaacuaau uugaauuuua augagagucg    300 uugguucucua uagagguuuc uagcugagga gauaaacgu aaaauauucu agaaacuaag    360
cauguagagg uuagcgggga guuuacuaag gacgagaguu cgaaucucuc caccuccacc    420
a                                                                    421

<210> SEQ ID NO 131
<211> LENGTH: 426
<212> TYPE: RNA
<213> ORGANISM: Chlamydia pneumoniae

<400> SEQUENCE: 131
ggggguguau agguuucgac uugaaaauga aguguuaauu gcaugcggag ggcguuggcu     60
ggccuccuaa aaagccaaca aaacaauaaa ugccgaaccu aaggcugaau gcgaaauuau    120
uagcuuguuu gacucaguag aggaaagacu agcugcuuaa uuagcaaaag uuguuagcua    180
gauaaucucu agguaacccg guaucugcga gcuccaccag aggcuugcaa aauaccguca    240
uuuaucuggu uggaacuuac uuucucuaau ucucaaggaa guucgucga gauuuuugag    300 agucauuggc ugcuauagag gcuucuagcu aagggagucc aauguaaaca auucuagaag    360
auaagcaugu agagguuagc agggaguuug ucaaggacga gaguucgagu cucuccaccu    420
ccacca                                                               426

<210> SEQ ID NO 132
<211> LENGTH: 328
<212> TYPE: RNA
```

<213> ORGANISM: Micrococcus luteus

<400> SEQUENCE: 132

| | | | | | |
|---|---|---|---|---|---|
| cggugugugu | cgcgucggga | gaagcgggcc | gaggaugcag | agucaucucg | ucaaacgcuc | 60 |
| ucugcaaacc | aauaagugcc | gaauccaagc | gcacugacuu | cgcucucgcu | gccugaucag | 120 |
| ugaucgaguc | cgucaccccg | aggucgcugu | cgccucggau | cguggcguca | gcuagauagc | 180 |
| cacugggcgu | cacccucgcc | ggggucgug | acgccgacau | caauccggcu | gggucccgggu | 240 |
| uggccgcccg | ucugcgggac | ggccaggacc | gagcaacacc | cacagcagac | ugcgcccgga | 300 |
| gaagaccugg | caacaccuca | ucggacgc | | | 328 |

<210> SEQ ID NO 133
<211> LENGTH: 368
<212> TYPE: RNA
<213> ORGANISM: Mycobacterium leprae

<400> SEQUENCE: 133

| | | | | | |
|---|---|---|---|---|---|
| ggggcugaaa | gguuucgacu | ucgcgcaucg | aaucaaggga | agcgugccgg | ugcaggcaag | 60 |
| agaccaccgu | aagcgucguu | gcagcaauau | aagcgccgau | ucauaugagc | gcgacuaugc | 120 |
| ucucgcugcc | uaagcgaugg | cuagucuguc | agaccgggaa | cgcccucguc | ccggagccug | 180 |
| gcaucagcua | gagggaucua | ccgaugggu | cggucgcggg | acucgucggg | acaccaaccg | 240 |
| cgacugggau | cgucauccug | gcuaguucgc | gugaucagga | gauccgagua | gaggcauagc | 300 |
| gaacuacgca | cggagaagcc | uugagggaaa | ugccguagga | cccggguucg | auucccggca | 360 |
| gcuccacc | | | | | 368 |

<210> SEQ ID NO 134
<211> LENGTH: 360
<212> TYPE: RNA
<213> ORGANISM: Mycobacterium tuberculosis

<400> SEQUENCE: 134

| | | | | | |
|---|---|---|---|---|---|
| ggggcugaac | gguuucgacu | ucgcgcaucg | aaucaaggga | agcgugccgg | ugcaggcaag | 60 |
| agaccaccgu | aagcgucguu | gcgaccaaau | aagcgccgau | ucacaucagc | gcgacuacgc | 120 |
| ucucgcugcc | uaagcgacgg | cuagucuguc | agaccgggaa | cgcccucggc | ccggacccug | 180 |
| gcaucagcua | ccaccgauga | guccggucgc | gggacuccuc | gggacaacca | cagcgacugg | 240 |
| gaucgucauc | ucggcuaguu | cgcgugaccg | ggagauccga | gcagaggcau | agcgaacugc | 300 |
| gcacggagaa | gccuugaggg | aaugccguag | gacccggguu | cgauucccgg | cagcuccacc | 360 |

<210> SEQ ID NO 135
<211> LENGTH: 373
<212> TYPE: RNA
<213> ORGANISM: Mycobacterium avium

<400> SEQUENCE: 135

| | | | | | |
|---|---|---|---|---|---|
| ggggcugaaa | gguuucgacu | ucgcgcaucg | aaucaaggga | agcgugccgg | ugcaggcaac | 60 |
| ugaccaccgu | aagcgucguu | gcagauagau | aagcgccgau | ucacaucagc | gcgacuacgc | 120 |
| ucucgcugcc | uaagcgacag | cuagucgagg | gaucgucagc | ccgggaacgc | ccucgacccg | 180 |
| gagccuggcg | ucagcuagag | ggauccaccg | augaguucgg | ucgcgggacu | caucgggaca | 240 |
| ccaacagcga | cugggaucgu | cauccuggcu | guucgcgug | accaggagau | ccgaguagag | 300 |
| gcauagcgaa | cugcgcacgg | agaagccuug | agggaaugcc | guaggacccg | gguucgauuc | 360 |
| ccggcagcuc | cac | | | | 373 |

<210> SEQ ID NO 136
<211> LENGTH: 331
<212> TYPE: RNA
<213> ORGANISM: Corynebacterium xerosis

<400> SEQUENCE: 136

| | | | | | |
|---|---|---|---|---|---|
| cuucguacau | ugagccaggg | gaagcgugcc | ggugaaggcu | ggagaccacc | gcaagcgucg | 60 |
| cagcaaccaa | uuaagcgccg | agaacucuca | gcgcgacuac | gcccucgcug | ccuaagcagc | 120 |
| gaccgcgugu | cugucagacc | ggguaggccu | cugauccgga | cccuggcauc | guuuaguggg | 180 |
| gcucgcucgc | cgacuugguc | gcaagggucg | gcggggacac | ucacuugcga | cugggcccgu | 240 |
| cauccgguca | guucgacug | aaccggaggg | ccgagcagag | accacgcgcg | aacugcgcac | 300 |
| ggagaagccc | uggcgaggug | acggaggacc | c | | | 331 |

<210> SEQ ID NO 137
<211> LENGTH: 354
<212> TYPE: RNA
<213> ORGANISM: Treponema pallidum

<400> SEQUENCE: 137

| | | | | | |
|---|---|---|---|---|---|
| ggggaugacu | agguuucgac | uagggaugug | ggguguugcg | cugcaggugg | agugucgauc | 60 |
| uccugauucg | gcgccuuuau | aacugccaau | ucugacaguu | ucgacuacgc | gcucgccgcg | 120 |
| uaaucgcggg | ccuguguuug | cgcugcucug | agcgaacaua | ucggcccgac | gccaaacgga | 180 |
| gcuugcucuu | acguugugca | cggcggacgu | aggggggacuu | uugucugugc | uaagacucug | 240 |
| gcgcgugcgg | ugcaggccua | gcagagucug | acaaacgcag | uacgcaccgc | uaaaccugua | 300 |
| ggcgcgcagc | acucgcucuu | uaggacgggg | guucgauucc | ccccaucucc | acca | 354 |

<210> SEQ ID NO 138
<211> LENGTH: 362
<212> TYPE: RNA
<213> ORGANISM: Borrelia burgdorferi

<400> SEQUENCE: 138

| | | | | | |
|---|---|---|---|---|---|
| ggggauguuu | uggauuugac | ugaaaauguu | aauauuguaa | guugcaggca | gagggaaucu | 60 |
| cuuaaaacuu | cuaaaauaaa | ugcaaaaaau | aauaacuuua | caagcucaaa | ucuuguaaug | 120 |
| gcugcuuaag | uuagcagagg | guuuuguuga | auuggcuuu | gagguucacu | uauacucuuu | 180 |
| ucgacaucaa | agcuugcuua | aaaauguuuu | caaguugauu | uuuagggacu | uuuauacuug | 240 |
| agagcaauuu | ggugguuugc | uaguauuucc | aaaccauauu | gcuuaauaaa | auacuagaua | 300 |
| agcuuguaga | agcuuauagu | auuauuuuua | ggacgcgggu | ucaauucccg | ccaucuccac | 360 |
| ca | | | | | | 362 |

<210> SEQ ID NO 139
<211> LENGTH: 364
<212> TYPE: RNA
<213> ORGANISM: Borrelia garinii

<400> SEQUENCE: 139

| | | | | | |
|---|---|---|---|---|---|
| ggggcugauu | cuggauucga | cugaaaaugc | gaauauugua | aguugcaggc | agagggaauc | 60 |
| ucuuaaaacu | ucuaaaauaa | augcaaaaaa | uaauaacuuu | acaagcucaa | accuuguaau | 120 |
| ggcugcuuaa | guuagcaggg | aguuucguug | aauuuggcuu | ugagguucac | uuauacucuu | 180 |
| uucgauaucg | aagcuugcuu | aaaaauguuu | ucaaguuaau | uuuuagggac | uuuuguacuu | 240 |

-continued

```
gagagcaauu uggcgguuug cuaguauuuc caaaccauau ugcuuaagua aaaugcuaga    300
uaagcuugua gaagcuuaua auauuguuuu uaggacgcgg guucaauucc cgccaucucc    360
acca                                                                  364
```

```

<210> SEQ ID NO 140
<211> LENGTH: 363
<212> TYPE: RNA
<213> ORGANISM: Borrelia afzelii

<400> SEQUENCE: 140
ggggcugauu cuggauucga cugaaaaugc uaauauugua aguugcaagc agagggaauc     60
ucuuaaaacu ucuaaaauaa augcaaaaaa uaauaacuuu acaaguucaa accuuguaau    120
ggcugcuuaa guuagcagag aguuuuguug aauuuggcuu ugagauucac uuauacucuu    180
uuagacaucg aagcuugcuu aaaaauguuu ucaaguugau uuuuagggac uuuuauacuu    240
gagagcaauu uggcgguuug cuaguauuuc caaaccauau ugcuuaguaa aauacuagau    300
aagcuuguag aagcuuauag uauuguuuuu aggacgcggg uucaauuccc gccaucucca    360
cca                                                                   363
```

```

<210> SEQ ID NO 141
<211> LENGTH: 363
<212> TYPE: RNA
<213> ORGANISM: Borrelia crocidurae

<400> SEQUENCE: 141
ggggcugauu cuggauucga cuaagaacuu uaguagcaua aauggcaagc agagugaauc     60
ucuuaaaacu ucuuuaauaa augcaaaaaa uaauaacuuu acaaguucag aucuuguaau    120
ggcugcuuaa uuuagcagag aguuuuguug gauuuugcuu ugagguucaa cuuauacucu    180
uuaagacauc aaaguaugcc uaaaaauguu ucaaguugau uuuuagggac cuuuaaacuu    240
gagaguaauu uggugguuug cuuguuuucc aagccuuauu gcuuuuucua aaaauuagcu    300
aagcuuguag auauuuauga uauuauuuuu uggacgcggg uucaauuccc gccaucucca    360
cca                                                                   363
```

```
<210> SEQ ID NO 142
<211> LENGTH: 365
<212> TYPE: RNA
<213> ORGANISM: Borrelia hermsii

<400> SEQUENCE: 142
ggggcugauu cuggauucga cuaaaaacuu uaguagcaua aauugcaagc agagggaauc     60
ucuuaaaacu ucuuuaauaa augcaagaaa uaauaacuuu acaaguucaa aucuuguaau    120
ggcugcuuaa auuagcagag aguucugcug gauuuugcuu ugagguucag cuuauacucu    180
uuuaagacau caaagcuugc uuaaaaauau uucaaguuga uuuuuaggga cuuuuaaauu    240
ugagaguaau uuggcgguuu gcuaguuuuu ccaaaccuua uuacuuaaag aaaacacuag    300
cuaagcuugu agauauuuau gauauuauuu uuaggacgcg gguucaauuc ccgccaucuc    360
cacca                                                                 365
```

```
<210> SEQ ID NO 143
<211> LENGTH: 330
<212> TYPE: RNA
<213> ORGANISM: Alcaligenes faecalis

<400> SEQUENCE: 143
```

```
cgggggucaa gaagcagcac agggcguguc gagcaccagu acgcucguaa auccacugga    60
aaacuauaaa cgccaacgac gagcguuucg cucuagccgc uuaaggcugg ccacugcac   120 uaauuugucu uuggguuagg uagggcaacc uacagcagug uuauuacaa agaaucgaau   180 cggucugcgc cacgaaguee gguucuaaaa cuuaguggau cgccaaggaa aggccuguca   240
auuggcauag uccaagguua aaacuuaaaa uuaauugacu acacauguag aacugucugu   300
ggacggcuug cggacggggg uucgauuccc                                    330

<210> SEQ ID NO 144
<211> LENGTH: 340
<212> TYPE: RNA
<213> ORGANISM: Alcaligenes eutrophus

<400> SEQUENCE: 144 cgugggguuac aaagcagugg agggcauacc gaggacccgu caccucguua aucaauggga   60
augcaauaac ugcuaacgac gaacguuacg cacuggccgc uuaauugcgg ccguccucgc   120
acuggcucgc ugacgggcua ggucgcaag accacgcgag gucauuuacg ucagauaagc   180
uccggaaggg ucacgaagcc ggggacgaaa accuagugac ucgccgucgu agagcguguu   240
cguccgcgau gcgccgguua aaucaaauga cagaacuaag uauguagaac ucucugugga   300
gggcuuacgg acgcggguuc gauucccgcc ggcuccacca                         340

<210> SEQ ID NO 145
<211> LENGTH: 326
<212> TYPE: RNA
<213> ORGANISM: Ralstonia pickettii

<400> SEQUENCE: 145 cgggggugc gaagcagcgg agggcauacc gaggacccgu caccucguua aucaauggga    60
augcaauaac ugcuaacgac gaacguuacg cacuggcagc uuaagggccg ccguccucgc   120
acuggcucgc ugacgggcua ggucgcaag accagcgagg ucauuuacgu cagauaagcu   180
uuaggugagu cacgggccua gagacgaaaa cuuaguugaau cgccgucgua gagcguguuc   240
guccgcgaug cggcgguuaa aucaaaugac agaacuaagu auguagaacu cucuggga   g 300 ggcuugcgga cgcgggguucg auuccc                                       326

<210> SEQ ID NO 146
<211> LENGTH: 363
<212> TYPE: RNA
<213> ORGANISM: Neisseria gonorrhoeae

<400> SEQUENCE: 146
gggggcgacc uugguuucga cggggguugc gaagcagaug cgggcauacc ggggucucag    60
auucccguaa aacacugaau ucaaauaguc gcaaacgacg aaacuuacgc uuugccgcu   120 uaaggcuagc cguugcagca gucggucaau gggcugugug gugaaagcca ccgcaacguc   180
aucuuacauu gacugguuuc cagccggguu acuggcagg aaauaagacu uaagguaacu   240
gguuuccaaa aggccuguug gucggcauga uggaaauaag auuuucaaau agacacaacu   300
aaguauguag aacgcuuugu agaggacuuu cggacggggg uucgauuccc cccgccucca   360
cca                                                                 363

<210> SEQ ID NO 147
<211> LENGTH: 363
<212> TYPE: RNA
```

<213> ORGANISM: Neisseria meningitidis

<400> SEQUENCE: 147

```
gggggcgacc uugguuucga cgggggguugc gaagcagaug cgggcauacc ggggucucag    60
auccccguaa aacacugaau ucaaauaguc gcaaacgacg aaacuuacgc uuuagccgcu   120
uaaggcuagc cguugcagca gucggucaau gggcugugug gcgaaagcca ccgcaacguc   180
aucuuacauu gacugguuuc cugccggguu auuuggcagg aaaugagauu uaagguaacu   240
gguuuccaaa aggccuguug gucggcauga uggaaauaag auuuucaaau agacacaacu   300
aaguauguag aacgcuuugu agaggacuuu cggacggggg uucgauuccc cccgccucca   360
cca                                                                 363
```

<210> SEQ ID NO 148
<211> LENGTH: 333
<212> TYPE: RNA
<213> ORGANISM: Chromobacterium violaceum

<400> SEQUENCE: 148

```
cgggggguugc gaagcagaug agggcauacc gggauuucag ucaccccgua aaacgcugaa    60
uuuauauagu cgcaaacgac gaaacuuacg cucuggcagc cuaacggccg gccagacacu   120
acaacgguuc gcagauggc cggggcguc aaaacccugu agugcacuc uacaucugcu     180
agugcuguuc cggguuacuu gguucagugc gaaauaauag guaacucgcc aaaguccagc   240
cuguccgucg gcguggcaga gguuaaauuc aaaugacacg acuaaguaug uagaacucac   300
uguagaggac uuucggacgc ggguucaacu ccc                                333
```

<210> SEQ ID NO 149
<211> LENGTH: 330
<212> TYPE: RNA
<213> ORGANISM: Nitrosomonas cryotolerans

<400> SEQUENCE: 149

```
cgugggguugc aaagcagcgc agggcauacc gaggaccaga auaccucgua aauacaucug    60
gaaaaaaaua gucgcaaacg acgaaaacua cgcuuuagcc gcuuaauacg gcuagccucu   120
gcaccgaugg gccuuaacgu cgggucuggc aacagacagc agagucauua gcaaggaucg   180
cguucuguag ggucacuuua cagaacguua aacaauaggu gacucgccug ccaucagccc   240
gccagcuggc gguugucagg uuaaauuaaa gagcauggcu aaguauguag aacugucugu   300
agaggacuug cggacgcggg uucaacuccc                                    330
```

<210> SEQ ID NO 150
<211> LENGTH: 331
<212> TYPE: RNA
<213> ORGANISM: Methylobacillus glycogenes

<400> SEQUENCE: 150

```
cgggggguugc aaagcagcgc agggcauacc gaggccuagu caccucguaa auaaacuaga    60
acaaguauag ucgcaaacga cgaaacuuac gcucuagccg cuuaauccccg gcuggacgcu   120
gcaccgaagg gccucucggu cgggugggu aacccacagc agcgucauua agagaggauc    180
gugcgauauu ggguuacuua auacgauauu aaauccaagg uaacucgccu gcuguuugcu   240
ugcucguugg ugagcaucag guuaaaucaa acaacacagc uaaguaugua gaacugucug   300
uggagggcuu gcggacgggg guucgauucc c                                  331
```

-continued

<210> SEQ ID NO 151
<211> LENGTH: 375
<212> TYPE: RNA
<213> ORGANISM: Pseudomonas testosteroni

<400> SEQUENCE: 151
ggggccgauu cuggauucga cgugggguucg ggaccggugc ggugcauguc gagcuugagu 60
gacgcucgua aaucuccauu caaaaaacua acugcaaacg acgaacguuu cgcacucgcc 120
gcuuaauccg gugagccuug caacagcacg cuagugggcu gggcaagggg guagcaauac 180
cucccggcug caagggaauu uucauuagcu ggcuggauac cgggcuucuu gguauuuggc 240
gagauuuuag gaagcuggcu acccaagcag cgugugccug cgggguuugg guggcgagau 300
uuaaaacaga gcacuaaaca uguagaucug uccggcgaag gcuuacggac gcggguucaa 360
uucccgccgg cucca 375

<210> SEQ ID NO 152
<211> LENGTH: 353
<212> TYPE: RNA
<213> ORGANISM: Variovorax paradoxus

<400> SEQUENCE: 152 cgugggguucg gagucgcagc ggggcauguc gagcugaaug cgcucguaaa acagauucaa 60
acaaacuaac ugcaaacgac gaacguuucg cacucgcugc uuaauugcca gugagccuug 120
caacaguugg ccgaugggcu gggcaagggg gucuggagca auccugaccu cccggcugca 180
aggauaacua caugggcugg cuccgauccg gguaccuugg gucggggcga gaaaauaggg 240
uacuggcguc cgguuuagcg ugugacugcg cgacuccgga agcgagacuc aaaacagauc 300
acuaaacaug uagaacugcg cgaugaaggc uugcggacgg ggguucaacu ccc 353

<210> SEQ ID NO 153
<211> LENGTH: 345
<212> TYPE: RNA
<213> ORGANISM: Hydrogenophaga palleroni

<400> SEQUENCE: 153 cgugggguucg gacgcgcagc agggcauguc gagguucugu caccucguaa aucagcagaa 60
aaaaaccaac ugcaaacgac gaacguuucg cacucgccgc uuaaacaccg gugagccuug 120
caacagcagg ccgaugggcu gggcaagggg gucgcaagac cucccggcug caagguaauu 180
uacaucggcu gguucugcgu cgggcaccuu ggcgcaggau gagauucaag gaugcuggcu 240
ucccguuuag cgugccacug cgcgacucgg gcggcgagac ccaaaucaga cggcuacaca 300
uguagaacug cucgaaaaag gcuugcggac gggggguucaa cuccc 345

<210> SEQ ID NO 154
<211> LENGTH: 387
<212> TYPE: RNA
<213> ORGANISM: Bordetella pertussis

<400> SEQUENCE: 154
ggggccgauc cggauucgac gugggucaug aaacagcuca gggcaugccg agcaccagua 60
agcucguuaa uccacuggaa cacuacaaac gccaacgacg agcgucucgc ucucgccgcu 120
uaagcgguga gccgcugcac ugaucugucc uugggucagg cgggggaagg caacuuccca 180
gggggcaacc ccgaaccgca gcagcgacau ucacaaggaa ucggccaccg cuggggucac 240
acggcguugg uuuaaauuac gugaaucgcc cugguccggc ccgucgaucg gcuaagucca 300

```
gggutuaaauc caaauagauc gacuaagcau guagaacugg uugcggaggg cuugcggacg    360 ggggutucaau ucccccccggc uccacca                                      387

<210> SEQ ID NO 155
<211> LENGTH: 323
<212> TYPE: RNA
<213> ORGANISM: Legionella pneumophila

<400> SEQUENCE: 155 cgugggutugc aaaaccggaa gugcaugccg agaaggagau cucucguaaa uaagacucaa    60
uuaaauauaa augcaaacga ugaaaacuuu gcuggugggg aagcuaucgc ugccuaauaa   120
gcacuuuagu uaaaccauca cuguguacug gccaauaaac ccaguauccc guucgaccga   180
gcccgcuuau cgguaucgaa ucaacgguca uaagagauaa gcuagcgucc uaaucuaucc   240
cggguuaugg cgcgaaacuc agggaaucgc uguguaucau ccugcccguc ggaggagcca   300
caguuaaauu caaaagacaa ggc                                          323

<210> SEQ ID NO 156
<211> LENGTH: 315
<212> TYPE: RNA
<213> ORGANISM: Chromatium vinosum

<400> SEQUENCE: 156 cguggguucgc gaaaccuaag gugcaugccg aggugcgguu gaccucguaa aaccuccgc    60 aaacuuauag uugccaacga cgacaacuac gcucucgcug cuuaauccca gcgggccucu   120
gaccgucacu ugccuguggg cggcggauuc caggguaac cucacacagg aucggguga    180 cgggagucccg gaccugaucc acuaaaaccu aacggaaucg ccgacugauc gcccugcccu   240
ucgggcggca gaaggcuaaa aacaauagag ugggcuaagc auguaggacc gagggcagag   300
ggcuugcgga cgcgg                                                   315

<210> SEQ ID NO 157
<211> LENGTH: 318
<212> TYPE: RNA
<213> ORGANISM: Dichelobacter nodosus

<400> SEQUENCE: 157
cucgaggugc augucgagaa ugagagaauc ucguuaaaua cuuucaaaac uuauaguugc    60
aaacgacgac aacuacgcuu uagcggcuua auucccgcuu ucgcuuaccu agauuugucu   120
guggguuuac cguaagcgac auuaacacag aaucgcuggu uaacgcgucc gcuguuaauc   180
gguuaaauua agcggaaucg cuuguaaaau gccugagcgu uggcuguuua ugaguuaaac   240
cuaauuaacu gcucuaaaca uguaguacca aaaguuaagg auucgcggac gggguucaa   300 aucccccgc cuccacca                                                 318

<210> SEQ ID NO 158
<211> LENGTH: 354
<212> TYPE: RNA
<213> ORGANISM: Pseudomonas aeruginosa

<400> SEQUENCE: 158
ggggccgauu aggauucgac gccguaaca aaacuugagg ggcaugccga gcugguagca    60
gaacucguaa auucgcugcu gcaaacuuau aguugccaac gacgacaacu acgcucuagc   120
ugcuuaaugc ggcuagacag ucgcuagggg augccguaa acccgaaacg acugucagau   180
agaacaggau cgccgccaag uucgcuguag acguaacggc uaaaacucau acagcucgcu   240
```

-continued

| ccaagcaccc ugccacucgg gcggcgcgga guuaacucag uagagcuggc uaagcaugua | 300 |
| gaaccgauag cggagagcug gcggacgggg guucaaaucc ccccggcucc acca | 354 |

<210> SEQ ID NO 159
<211> LENGTH: 350
<212> TYPE: RNA
<213> ORGANISM: Pseudomonas fluorescens

<400> SEQUENCE: 159

| cgccgguugc gaaccuuuag gugcaugccg aguugguaac agaacucgua aauccacugu | 60 |
| ugcaacuuuc uuaguugcca augacgaaac cuacggggaa uacgcucucg cugcguaagc | 120 |
| agccuuagcc cuucccuccu gguaccuucg gguccagcaa ucaucagggg augucuguaa | 180 |
| acccaaagug auugucauau agaacagaau cgccgugcag uacguugugg acgaagcggc | 240 |
| uaaaacuuac acaacucgcc caaagcaccc ugcccgucgg gucgcugagg guuaacuuaa | 300 |
| uagacacggc uacgcaugua guaccgacag cagaguacug gcggacgggg | 350 |

<210> SEQ ID NO 160
<211> LENGTH: 323
<212> TYPE: RNA
<213> ORGANISM: Marinobacter hydrocarbonoclasticus

<400> SEQUENCE: 160

| cgccggugac gaacccuugg gugcaugccg agauggcagc gaaucucgua aauccaaagc | 60 |
| ugcaacguaa uagucgcaaa cgacgaaaac uacgcacugg cggcguaagc cguuccaguc | 120 |
| guccuggcug aggcgccuau aacucaguag caacauccca ggacgucauc gcuuauaggc | 180 |
| ugcuccguuc accagagcuc acuggucuuc ggcuaagauu aaaagagccg ccucuugcac | 240 |
| ccugaccuuc gggucgcuug agguuaaauc aauagaagga cacuaagcau guagaccuca | 300 |
| aggccuagug cuggcggacg cgg | 323 |

<210> SEQ ID NO 161
<211> LENGTH: 355
<212> TYPE: RNA
<213> ORGANISM: Shewanella putrefaciens

<400> SEQUENCE: 161

| gggggcgauu cuggauucga caggauucac gaaacccugg gagcaugccg aggggcgguu | 60 |
| ggccucguaa aaagccgcaa aguuauaguu gcaaacgacg auaacuacgc ucuagccgcu | 120 |
| uaaugccgcu agccaucuac cacacgcuuu gcacaugggc aguggauuug auggucaucu | 180 |
| cacaucgugc uagcgaggga acccugucug ggggugaacc gcgaaacagu accgacucu | 240 |
| ccguguggga uccugucuuu cggaguucaa acgguuaaac aauagaaaga cuaagcaugu | 300 |
| agcgccuugg auguagguuu ucuggacgcg gguucaaguc ccgccgccuc cacca | 355 |

<210> SEQ ID NO 162
<211> LENGTH: 314
<212> TYPE: RNA
<213> ORGANISM: Pseudoalteromonas haloplanktis

<400> SEQUENCE: 162

| cggaauucaa gaagcccgag gugcaugucg aggugcgguu ugccucguaa aaagccgca | 60 |
| auuuaaagua aucgcaaacg acgauaacua cucucuagca gcuuaggcug gcuagcgcuc | 120 |
| cuuccaugua uucuugugga cuggauuuug gagugucacc cuaacaccug aucgcgacgg | 180 |

| aaacccuggc cgggguugaa gcguuaaaac uaagcggccu cgccuuuauc uaccguguuu | 240 |
|---|---|
| guccgggauu uaaagguuaa uuaaaugaca auacuaaaca uguaguaccg acggucgagg | 300 |
| cuuuucggac gggg | 314 |

<210> SEQ ID NO 163
<211> LENGTH: 316
<212> TYPE: RNA
<213> ORGANISM: Aeromonas salmonicida

<400> SEQUENCE: 163

| caagauucac gaaacccaag gugcaugccg aggugcggua ggccucguua acaaaccgca | 60 |
|---|---|
| aaaaaauagu cgcaaacgac gaaaacuacg cacuagcagc uuaauaaccu gcauagagcc | 120 |
| cuucuacccu agcuugccug guccuaggg aaucggaagg ucauccuuca caggaucgug | 180 |
| uggaagucccu gcucggggcg gaagcauuaa aaccaaucga gcuagucaau cguggcgug | 240 |
| ucucuccgca gcggguuggc gaauguaaag agugacuaag cauguaguac cgaggaugua | 300 |
| guaauuuugg acgggg | 316 |

<210> SEQ ID NO 164
<211> LENGTH: 363
<212> TYPE: RNA
<213> ORGANISM: Salmonella typhimurium

<400> SEQUENCE: 164

| ggggcugauu cuggauucga cgggauuugc gaaacccaag gugcaugccg aggggcgguu | 60 |
|---|---|
| ggccucguaa aaagccgcaa aaaauaguc gcaaacgacg aaaccuacgc uuuagcagcu | 120 |
| uaauaaccug cuuagagccc ucucucccua gccuccgcuc uuaggacggg gaucaagaga | 180 |
| ggucaaaccc aaaagagauc gcgcggaugc ccugccuggg guugaagcgu aaaacgaau | 240 |
| caggcuaguc ugguagugcc guguccgucc gcaggugcca ggcgaaugua aagacugacu | 300 |
| aagcauguag uaccgaggau guaggaauuu cggacgcggg uucaacuccc gccagcucca | 360 |
| cca | 363 |

<210> SEQ ID NO 165
<211> LENGTH: 363
<212> TYPE: RNA
<213> ORGANISM: Escherichia coli

<400> SEQUENCE: 165

| ggggcugauu cuggauucga cgggauuugc gaaacccaag gugcaugccg aggggcgguu | 60 |
|---|---|
| ggccucguaa aaagccgcaa aaaauagucg caaacgacga aaacuacgcu uuagcagcuu | 120 |
| aauaaccugc uuagagcccu cucucccuag ccuccgcucu uaggacgggg aucaagagag | 180 |
| gucaaaccca aaagagaucg cguggaagcc cugccuggg uugaagcguu aaaacuuaau | 240 |
| caggcuaguu uguuagugc guguccgucc gcagcggca agcgaaugua aagacugacu | 300 |
| aagcauguag uaccgaggau guaggaauuu cggacgcggg uucaacuccc gccagcucca | 360 |
| cca | 363 |

<210> SEQ ID NO 166
<211> LENGTH: 364
<212> TYPE: RNA
<213> ORGANISM: Yersinia pestis

<400> SEQUENCE: 166

| ggggcugauu cuggauucga cgggauucgc gaaacccaag gugcaugccg aggugcggug | 60 |

```
gccucguaaa aaaccgcaaa aaaaauaguu gcaaacgacg aaaacuacgc acuagcagcu        120
uaauaaccug cuuagagccc ucucucccua gccuccgcuc uuaggacggg gaucaagaga        180
ggucaaaccu aaaagagcuc guguggaaac cuugccuggg guggaagcau aaaacuaau        240 caggauaguu ugucaguagc guguccaucc gcagcuggcc ggcgaaugua augauuggac        300
uaagcaugua gugccgacgg guaguaauu ucggacgggg guucaaaucc ccccagcucc         360
acca                                                                    364

<210> SEQ ID NO 167
<211> LENGTH: 367
<212> TYPE: RNA
<213> ORGANISM: Vibrio cholerae

<400> SEQUENCE: 167
ggggcugauu caggauucga cgggaauuuu gcagucugag gugcaugccg aggugcggua        60
ggccucguua acaaccgca aaaaauagu cgcaaacgac gaaaacuacg cacuagcagc         120
uuaauacccu gcucagagcc cuuccucccu agcuuccgcu uguaagacgg ggaaaucagg        180
aaggucaaac caaaucaagc uggcguggau uccccaccu gagggaugaa gcgcgagauc        240
uaauucaggu uagccauucg uuagcguguc ggucgcagg cggugguga auuaaagauc         300 gacuaagcau guaguaccaa agaugaaugg uuucggacg ggguucaac ucccccccagc        360 uccacca                                                                 367

<210> SEQ ID NO 168
<211> LENGTH: 366
<212> TYPE: RNA
<213> ORGANISM: Haemophilus influenzae

<400> SEQUENCE: 168
ggggcugauu cuggauucga cgggauuagc gaagcccaag gugcacgucg aggugcggua        60
ggccucguaa auaaaccgca aaaaaauacu cgcaaacgac gaacaauacg cuuuagcagc       120
uuaauaaccu gcauuuagcc uucgcgcucc agcuuccgcu cguaagacgg ggauaacgcg       180
gagucaaacc aaaacgagau cguguggaag ccaccguuug aggaucgaag cacuaaauug       240
aaucaaacua gcuuaaguuu agcgucucug uccgcaugcu uaagugaaau uaaagacgag       300
acuaaacgug uaguacugaa gguagaguaa uuucggacgg ggguucaacu ccccccagcu       360
ccacca                                                                  366

<210> SEQ ID NO 169
<211> LENGTH: 366
<212> TYPE: RNA
<213> ORGANISM: Haemophilus actinomycetemcomitans

<400> SEQUENCE: 169
ggggcugauu cuggauucga cgggauuagc gaagcccgaa gugcacgucg aggugcggua        60
ggccucguaa auaaaccgca aaaaaauagu cgcaaacgac gaacaauacg cuuuagcagc       120
uuaauaaccu gccuuuagcc uucgcuccccc agcuuccgcu cguaagacgg ggauaaagcg       180
gagucaaacc aaaacgagau cguguggaag ccaccguuug aggaucgaag cauuaaauua       240
aaucaaagua gcuuaauugu cgcguguccg ucagcaggau uagugaauu uaagaccgg         300 acuaaacgug uagugcuaac ggcagaggaa uuucggacgg ggguucaacu ccccccagcu       360
ccacca                                                                  366
```

<210> SEQ ID NO 170
<211> LENGTH: 354
<212> TYPE: RNA
<213> ORGANISM: Desulfovibrio desulfuricans

<400> SEQUENCE: 170

| | | | | | |
|---|---|---|---|---|---|
| cggggacgug | gaagccguag | cggcaggucg | aggcgccgcu | ggccucguaa | aaagcggcac | 60
| aaaaguaauu | gccaacaacg | auuacgacua | cgcuuacgcu | gccuaauaac | agcgaggcaa | 120
| ugaccguuua | acggucgcgc | cgaucagggc | caugccugau | aacccugauu | cacuuaucag | 180
| gcuggcgaaa | accggcucuc | gccggggguuu | ucgcgagga | guuaccggc | gggauuccug | 240
| cguugugccu | ggucagggc | caacagcgcg | ugaaauaca | uacuugaccu | aaaccuguag | 300
| augcuucgug | uggaauguuc | ucggacgggg | guucaaaucc | ccccggcucc | acca | 354

<210> SEQ ID NO 171
<211> LENGTH: 366
<212> TYPE: RNA
<213> ORGANISM: Myxococcus xanthus

<400> SEQUENCE: 171

| | | | | | |
|---|---|---|---|---|---|
| gggggcggaa | aggauucgac | gggggcauug | aaguucgaga | cgcgugccga | gcuugucagg | 60
| uagcucguaa | auucaacccg | gcaaagacac | aaaagccaac | gacaacguug | agcucgcgcu | 120
| ggcugccuaa | aaacagccca | uagugcgcgg | uccccccgcc | cucggccugu | gggguuggga | 180
| cagaccguca | uaaugcaggc | uggcugccga | ggguugccugg | acccgaggug | gcagaucuu | 240
| cccaggaccg | gcucugagua | ucccguccgu | gggagccuca | gggacguagc | aaaucgcgga | 300
| cuacgcacgu | agggucgaag | agcggacggc | uuucggacgc | ggguucgauu | cccgccgccu | 360
| ccacca | | | | | | 366

<210> SEQ ID NO 172
<211> LENGTH: 346
<212> TYPE: RNA
<213> ORGANISM: Bdellovibrio bacteriovirus

<400> SEQUENCE: 172

| | | | | | |
|---|---|---|---|---|---|
| gggggcggaa | aggauucgac | gggggugcug | aagcauaagg | agcauaccgg | ggcggaugag | 60
| gaccucguua | aaaacguccca | cuuuguaauu | ggcaacgauu | acgcacuugc | agcuuaauua | 120
| agcagcacga | ucaaccuugu | ggugguuccg | cacuuggauu | gaucgucauu | uaggaccuc | 180
| ggcguguugg | guuuucucca | gcagacaugc | uuaaauuuac | uggggagag | gucuuaggga | 240
| uuuugucugu | ggaagcccga | ggaccaaucu | aaaacacuga | cuaaguaugu | agcgccuuau | 300
| cguggaucau | uugcggacgg | ggguucgauu | cccgccgccu | ccacca | | 346

<210> SEQ ID NO 173
<211> LENGTH: 386
<212> TYPE: RNA
<213> ORGANISM: Helicobacter pylori

<400> SEQUENCE: 173

| | | | | | |
|---|---|---|---|---|---|
| ggggcugacu | uggauuucga | cagauuucuu | gucgcacaga | uagcaugcca | agcgcugcuu | 60
| guaaaacagc | aacaaaaaua | acuguaaaca | acacagauua | cgcuccagcu | uacgcuaaag | 120
| cugcgugagu | uaaucucccuu | uuggagcugg | acugauuaga | auuucuagcg | uuuuaaucgc | 180
| uccauaaccu | uaagcuagac | gcuuuuaaaa | gguguucgc | cuuuuaaacu | aagaaacaag | 240
| aacucuugaa | acuaucucaa | gguuuuagaa | aguuggacca | gagcuaguuu | uaaggcuaaa | 300

```
aaaccaacca auuuucuaag cauuguagaa guuuguguuu agggcaagau uuuuggacug      360
ggguucgauu ccccacagcu ccacca                                          386

<210> SEQ ID NO 174
<211> LENGTH: 359
<212> TYPE: RNA
<213> ORGANISM: Campylobacter jejuni

<400> SEQUENCE: 174
gggagcgacu uggcuucgac aggaguaagu cugcuuagau ggcaugucgc uuugggcaaa       60
gcguaaaaag cccaaauaaa auuaaacgca aacaacguua aauucgcucc ugcuuacgcu      120
aaagcugcgu aaguucaguu gagccugaaa uuuaagucau acuaucuagc uuaauuuucg      180
gucauuuuug auaguguagc cuugcguuug acaagcguug aggugaaaua aagucuuagc      240
cuugcuuuug aguuuuggaa gaugagcgaa guagggugaa guagucaucu uugcuaagca      300
uguagagguc uuuguggau uauuuuugga caggggugucg auuccccucg cuuccacca      359

<210> SEQ ID NO 175
<211> LENGTH: 355
<212> TYPE: RNA
<213> ORGANISM: Sulfurospirillum deleyianum

<400> SEQUENCE: 175
caggaguagu uuuagcuuau ggcugcaugu cgggagugag ggucuuccgu uacacaaccu       60
ucaaacaaua acugcuaaca acaguaacua ucguccugcu uacgcgcuag cugcguaagu      120
uuaacaaaua auggacugcu cuccccuuug augcuaucuu aggaggucuu ggagaguauc      180
auagauuuga uagcuauauu acaugaacgc cuuuacaugu aaugaaguua aaggcucguu      240
uucguaguuu ucugauuguu guacgaagca aaauuaaaca cuaucaacaa uaucuaagca      300
uguagacguc auagguggcu auuuuuggac uggggguucaa cucccgccag cucca          355
```